US008992986B2

(12) United States Patent
Finnie et al.

(10) Patent No.: US 8,992,986 B2
(45) Date of Patent: Mar. 31, 2015

(54) CONTROLLED RELEASE OF BIOLOGICAL ENTITIES

(75) Inventors: Kim Suzanne Finnie, New South Wales (AU); David Jacques, New South Wales (AU); Christophe Jean Alexandre Barbe, New South Wales (AU); Linggen Kong, New South Wales (AU)

(73) Assignee: Australian Nuclear Science & Technology Organisation (AU)

( * ) Notice: Subject to any disclaimer, the term of this patent is extended or adjusted under 35 U.S.C. 154(b) by 1990 days.

(21) Appl. No.: 11/721,728

(22) PCT Filed: Dec. 20, 2005

(86) PCT No.: PCT/AU2005/001915
§ 371 (c)(1),
(2), (4) Date: Sep. 10, 2007

(87) PCT Pub. No.: WO2006/066317
PCT Pub. Date: Jun. 29, 2006

(65) Prior Publication Data
US 2009/0252808 A1 Oct. 8, 2009

(30) Foreign Application Priority Data

Dec. 20, 2004 (AU) ................................ 2004907219

(51) Int. Cl.

| | |
|---|---|
| *A61K 9/16* | (2006.01) |
| *A61K 9/14* | (2006.01) |
| *A61K 9/00* | (2006.01) |
| *A61K 9/50* | (2006.01) |
| *A61K 38/00* | (2006.01) |
| *A61K 38/48* | (2006.01) |
| *B01J 2/08* | (2006.01) |
| *B01J 13/02* | (2006.01) |
| *A61K 38/17* | (2006.01) |
| *A61K 38/46* | (2006.01) |
| *A61K 38/50* | (2006.01) |

(52) U.S. Cl.
CPC ........... *A61K 38/4826* (2013.01); *A61K 9/1611* (2013.01); *A61K 9/1694* (2013.01); *B01J 2/08* (2013.01); *B01J 13/02* (2013.01); *A61K 38/1709* (2013.01); *A61K 38/465* (2013.01); *A61K 38/482* (2013.01); *A61K 38/50* (2013.01); *A61K 9/501* (2013.01)
USPC ........... 424/491; 424/501; 424/400; 424/489; 514/1.1

(58) Field of Classification Search
None
See application file for complete search history.

(56) References Cited

U.S. PATENT DOCUMENTS

| | | | |
|---|---|---|---|
| 4,224,179 | A | 9/1980 | Schneider |
| 4,826,789 | A | 5/1989 | Jones et al. |
| 5,811,302 | A | 9/1998 | Ducheyne et al. |
| 5,849,331 | A | 12/1998 | Ducheyne et al. |
| 5,972,384 | A | 10/1999 | Thut et al. |
| 6,153,221 | A | 11/2000 | Thut et al. |
| 6,197,342 | B1 | 3/2001 | Thut et al. |
| 6,303,290 | B1 | 10/2001 | Liu et al. |
| 6,596,262 | B2 | 7/2003 | Zhu et al. |
| 6,764,690 | B2 | 7/2004 | Ahola et al. |
| 2002/0110527 | A1 | 8/2002 | Zhu et al. |
| 2002/0110528 | A1 | 8/2002 | Zhu et al. |
| 2002/0119117 | A1 | 8/2002 | Zhu et al. |
| 2003/0082238 | A1 | 5/2003 | Babich et al. |
| 2003/0166509 | A1 | 9/2003 | Edwards et al. |
| 2004/0043127 | A1 | 3/2004 | Monagle et al. |

FOREIGN PATENT DOCUMENTS

| | | |
|---|---|---|
| JP | 5-261274 | 3/1992 |
| WO | WO 00/09652 | 2/2000 |
| WO | WO 01/01139 A2 | 1/2001 |
| WO | WO 01/01139 A3 | 1/2001 |
| WO | WO 01/12221 A1 | 2/2001 |
| WO | WO 01/62232 | 8/2001 |

OTHER PUBLICATIONS

Handbook of Pharmaceutical Excipients (1986), p. 253; colloidal silica.*
C.C. Ribeiro et al., "Calcium phosphate-alginate microspheres as enzyme delivery matrices", Biomaterials 25 (2004) 4363-4373.
Sylvie Falaize et al., "In Vitro Behavior of Silica-Based Xerogels Intended as Controlled Release Carriers", J. Am. Ceram. Soc. 82 [4] 969-976 (1999).
Nik Kossovsky et al., "Surface-modified nanocrystalline ceramics for drug delivery applications", Biomaterials 1994, vol. 15, No. 15, pp. 1201-1211.
Alexander Kulak et al., "Single-step fabrication of drug-encapsulated inorganic microspheres with complex form by sonication-induced nanoparticle assembly", Chem. Commun. 2004, 576-577.
J.E. Barralet et al., "In vitro behavior of albumin-loaded carbonate hydroxyapatite gel", Journal of Biomedical Materials Research (2002) 60(3), 360-367.
W. Paul et al., "Development of porous spherical hydroxyapatite granules: application towards protein delivery", Journal of Materials Science: Materials in Medicine 10 (1999) 383-388.
D.-M. Liu et al., "Encapsulation of Protein Molecules in Transparent Porous Silica Matrices Via an Aqueous Colloidal Sol-Gel Process", Acta mater, vol. 47, No. 18, pp. 4535-4544, 1999.

(Continued)

*Primary Examiner* — Jeffrey T Palenik
(74) *Attorney, Agent, or Firm* — Baker & Hostetler LLP

(57) ABSTRACT

A process is provided for releasably encapsulating a biological entity. The process comprise combining a solution of a surfactant in a non-polar solvent with a precursor material and the biological entity to form an emulsion. The emulsion comprises a polar phase dispersed in a non-polar phase, wherein the polar phase comprises the biological entity. The particles comprising the biological entity are then formed from the polar phase.

21 Claims, 35 Drawing Sheets

(56) References Cited

OTHER PUBLICATIONS

Nadine Nassif et al., "Living bacteria in silica gels", Nature Materials, vol. 1, Sep. 2002, pp. 42-44.
K.S. Finnie et al., "Encapsulation of Biological Species in Sol-Gel Matrices", J. Aust. Ceram. Soc. vol. 36, No. 2, (2000) pp. 109-113.
Shula Radin et al., "In vitro bioactivity and degradation in behavior of silica xerogels intended as controlled release materials", Biomaterials 23, (2002) 3113-3122.
Yajun Wang et al., "Enzyme encapsulation in nanoporous silica spheres", Chem. Commun. 2004, pp. 1528-1529.
Translation Office Action Mexican Patent Application No. MX/a/2007/007373 dated Jul. 5, 2011.
Annex to the European Search Report European Application No. EP 05 81 8407 dated Nov. 14, 2011.
Ph. Colomban, "Gel Technology in Ceramics, Glass-Ceramics and Ceramic-Ceramic Composites", Ceramics International 15 (1989) 23-50.
C.J. Brinker et al., "SOL—GEL—Glass: 1. Gelation and Gel Structure", Journal of Non-Crystalline Solids 70 (1985) 301-322.
J. Sanchez et al., "Kinetic and Thermodynamic Study of the Hydrolysis of Silicon Alkoxides in Acidic Alcohol Solution", J. Phys. Chem., 1992, 96(22), 8973-8979.

* cited by examiner $C_9H_{19}$-$C_6H_4$-$(OCH_2CH_2)_5OH$    NP-5

AOT

Span 20

Span 40

Span 60

Span 80

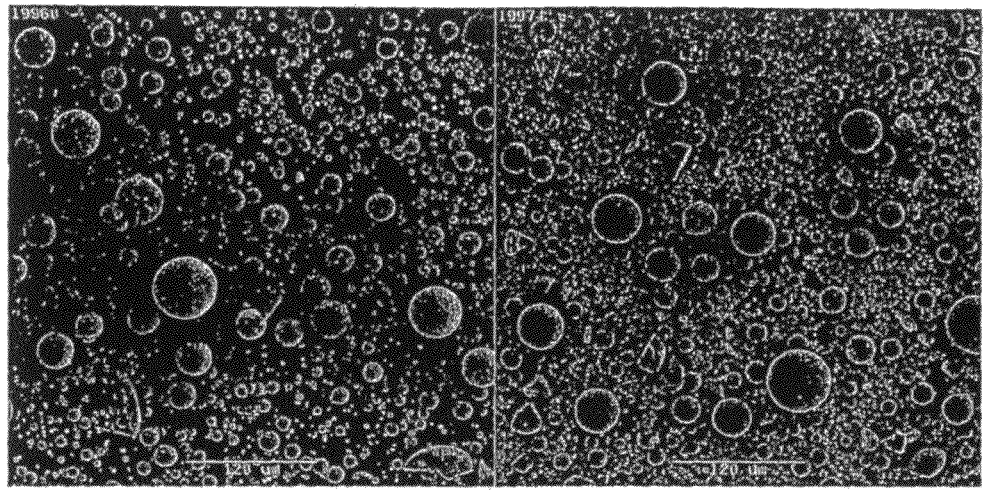
a: N-57 (bar = 120 μm)  b: AOT (bar = 120 μm)
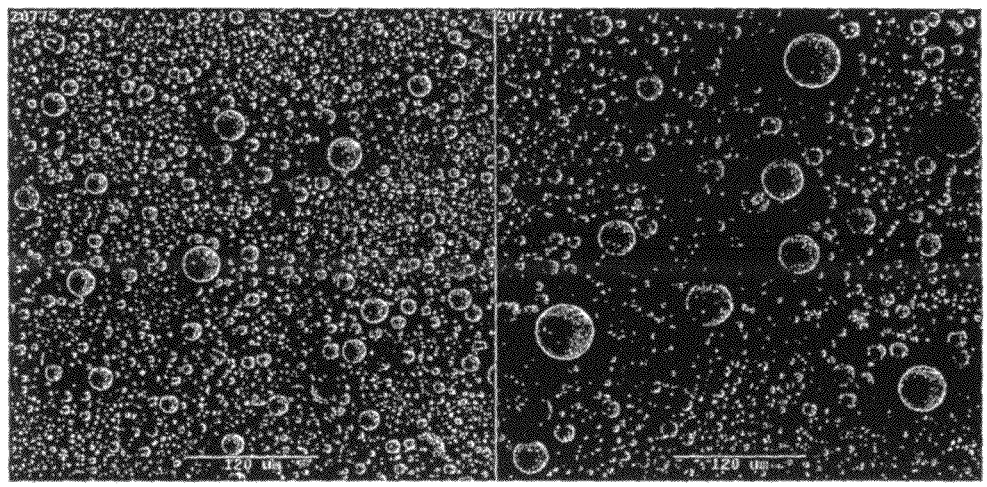
c: Span 20 (bar = 120 μm)  d: Span 40 (bar = 120 μm)

e: Span 60 (bar = 120 μm)   f: Span 80 (bar = 120 μm)

g: Brij 30 (bar = 4 μm)   h: NP-6 (bar = 3 μm)

i: Triton X-114 (bar = 7 μm)    j: NP-9 (bar = 30 μm)

k: Triton X-100 (bar = 30 μm)   l: Tween 21 (bar = 50 μm)

a: 0.05 mol/L (bar = 23 μm)      b: 0.1 mol/L (bar = 23 μm)

c: 0.2 mol/L (bar = 23 μm)       d: 0.3 mol/L (bar = 23 μm)

e: 0.4 mol/L (bar = 23 μm)  f: 0.5 mol/L (bar = 23 μm)

a: Petroleum Ether (bar = 120 μm)  b: Hexane (bar = 120 μm)

c: Octane (bar = 120 μm)     d: Decane (bar = 120 μm)

e: Docecane (bar = 120 μm)    f: Kerosene (bar = 120 μm)

a: 1.08 mL (bar = 120 μm)　　　b: 1.62 mL (bar = 120 μm)

c: 2.16 mL (bar = 120 μm)　　　d: 3.24 mL (bar = 120 μm)

e: 4.32 mL (bar = 120 μm)    f: 5.40 mL (bar = 120 μm)

a: pH 10.230 (bar = 23 μm)

b: pH 9.300 (bar = 23 μm)   c: pH 8.916 (bar = 23 μm)

d: pH 8.301 (bar = 50 nm)   e: pH 7.000 (bar = 50 nm)

a: pH 9.722 (bar = 120 μm)    b: pH 9.149 (bar = 120 μm)

c: pH 8.570 (bar = 120 μm)

a: Ludox SM-30 (bar = 120 μm)   b: Ludox HS-40 (bar = 120 μm)

c: Ludox TM-50 (bar = 2.3 μm)   d: Bindzil 30/360 (bar = 120 μm)

e: Bindzil 15/500 (bar = 120 μm)　　f: Snowtex 40 (bar = 120 μm)

g: Snowtex 50 (bar = 2.3 μm)　　h: Snowtex N (bar = 50 nm)

i: Snowtex UP (bar = 120 μm)     j: Snowtex 20L (bar = 2.3 μm)

k: Snowtex ZL (bar = 1.9 μm)     l: Snowtex ZL (bar = 0.2 μm)

US 8,992,986 B2

CONTROLLED RELEASE OF BIOLOGICAL ENTITIES

TECHNICAL FIELD

The present invention relates to ceramic particles for encapsulation and controlled release of biological entities.

BACKGROUND OF THE INVENTION

Required features of a biomolecule delivery system are to maintain the biomolecule structural integrity during encapsulation, storage and release, and to have a mechanism for enabling suitable release kinetics.

One common application is that of protein drug delivery. The present technology in protein drug delivery applications is largely polymer-based. There are several disadvantages with polymer-based systems as encapsulants for biological entities such as proteins:

Polymer production can involve use of chemicals and/or elevated temperatures, which can denature proteins;
Typically the release mechanism of protein from a polymer matrix is erosion (i.e. dissolution) of polymer matrix. Erosion (and thus release) rates are usually dependent on the chemical environment of the polymer particle (e.g. pH dependent). Erosion can also give rise to degradation by-products which will denature the proteins;
Polymer typically have hydrophobic surfaces, which require surface treatment to introduce hydrophilicity and thus enhanced stability in the blood;
Proteins may be damaged/denatured on storage due to for example dehydration;
Polymeric gels can undergo severe shrinkage during drying which can result in squeezing of the encapsulated protein and resulting in a change in their conformation.

WO 01/62232 (Barbé and Bartlett) refers to the incorporation of biological active materials into ceramic encapsulants, however, the chemistry described in the patent is not ideal for encapsulation and release of larger biomolecules. The short-chain alcohols released on hydrolysis of the silicon alkoxide precursors used to form the silica spheres are known to denature protein molecules, leading to significant loss of biological activity. In addition, the sol-gel reactions are usually conducted in presence of an acid or base catalyst, resulting in pHs incompatible with most biological molecules. Also, proteins range in size up to about 3000 kDa, and may exceed 10 nm diameter. The micropores formed in acidic conditions are commonly too small to allow release of molecules of this size, although the mesopores formed under basic conditions are larger and may enable release of small proteins. Ideally a system is required in which the pH can be maintained within the typical physiological range of ~5-8, conditions which are not suitable for catalysing the hydrolysis of silicon alkoxides.

JP5 261274 (Lion Corp.) describes a process for encapsulating biomolecules in a ceramic matrix. However the particles made by the patented process are not designed for controlled release of the biomolecules. In addition, the process exposes the biomolecules to harsh conditions such as extremes of pH and high shear which may denature or otherwise harm sensitive biomolecules, in particular proteins. Further, the rapid flocculation used in the process is likely to lead to very broad and uncontrolled particle size distributions.

There is therefore a need for a delivery system for biological entities which displays desirable release kinetics and is capable of maintaining the structural integrity of the biological entity during encapsulation, storage and release.

OBJECT OF THE INVENTION

It is the object of the present invention to overcome or substantially ameliorate at least one of the above disadvantages. It is another object to at least partially meet the above need.

SUMMARY OF THE INVENTION

In a first aspect of the invention there is provided a process for releasably encapsulating a biological entity comprising:
    forming an emulsion comprising emulsion droplets dispersed in a non-polar solvent, wherein the emulsion droplets comprise a precursor material and a biological entity; and
    forming particles from the emulsion droplets, said particles having the biological entity therein and/or thereon.

In the step of forming an emulsion, a first emulsion may be formed from the non-polar solvent, a surfactant and the precursor material, and the biological entity combined with the first emulsion, or a first emulsion may be formed from the non-polar solvent, a surfactant and the biological entity, and the precursor material combined with that emulsion, or the biological entity may be combined with the precursor material and the resulting mixture combined with the non-polar solvent and surfactant to form the emulsion, or some other order of addition may be employed. Alternatively the step of forming an emulsion may comprise combining the surfactant and the non-polar solvent with an aqueous solution, optionally an acidic, aqueous solution, to form a first emulsion, and combining the first emulsion with the precursor material and the biological entity to form the emulsion. The first emulsion may be for example a microemulsion, or a small droplet size emulsion.

Thus the present invention provides a process for releasably encapsulating a biological entity comprising:
    a) combining a solution of a surfactant in a non-polar solvent with a precursor material and the biological entity to form an emulsion comprising a polar phase dispersed in a non-polar phase, said polar phase comprising the biological entity; and
    b) forming particles comprising the biological entity from the polar phase.

The polar phase may also comprise the precursor material. Step a) of the process may comprise:
    c) combining the solution of the surfactant in the non-polar solvent with the precursor material to form a first emulsion, said first emulsion having a polar phase dispersed in a non-polar phase and said precursor material being located in the polar phase; and
    d) combining the biological entity with the first emulsion such that the polar phase comprises the biological entity.

The process may additionally comprise the step of adjusting the pH of the first emulsion to a pH appropriate for the biological entity in question, i.e. to a pH that will not degrade or denature the biological entity or to a pH that will not cause it to deteriorate. The pH may be adjusted to a pH at which the biological entity remains active, e.g. biologically active. That pH may be between about 1 and about 11, or between about 2 and 11, 3 and 11, 4 and 11, 5 and 11, 6 and 11, 7 and 11, 1 and 9, 1 and 7, 1 and 5, 2 and 10, 2 and 8, 2 and 7, 3 and 9, 3 and 7, 3 and 5, 5 and 6, 6 and 7, 7 and 8, 8 and 9, 9 and 10, 5 and 8, 5 and 7, 5 and 8.5, 10 and 11, 5 and 7, 8 and 10, 8.5 and 10, 9 and 11 or 8.5 and 11, for example about 1, 1.5, 2, 2.5, 3, 3.5, 4, 4.5, 5, 5.5, 6, 6.5, 7, 7.6, 8, 8.5, 9, 9.5, 10, 10.5 or 11. Adjusting the pH may be performed before step d).

Step a) of the process may comprise.

e) combining the solution of the surfactant in the non-polar solvent with an aqueous acid to form a second emulsion (which may optionally be a microemulsion or a small droplet size emulsion), said second emulsion having a polar phase dispersed in a non-polar phase;

f) adding the precursor material to the second emulsion such that the precursor material is located in the polar phase; and g) adding the biological entity such that the polar phase comprises the biological entity.

Alternatively step a) may comprise:

h) combining the precursor material and the biological entity to form a polar mixture; and i) combining the polar mixture with the solution of the surfactant to form the emulsion, said emulsion having a polar phase dispersed in a non-polar phase, such that the polar phase comprises the precursor material and the biological entity.

This alternative may also comprise adjusting the pH of the precursor material to between about 1 and about 11, or between about 3 and 11, 5 and 11, 7 and 11, 7.5 and 11, 1 and 9, 1 and 7, 1 and 5, 3 and 9, 3 and 7, 5 and 9, 5 and 7, 7.5 and 9.5, 8.5 and 9, 9 and 10, 9.5 and 10, 9 and 9.5, 5 and 8, 5 and 7, 5 and 8.5, 10 and 11, 5 and 7, 8 and 10, 8.5 and 10, 9 and 11 or 8.5 and 11, for example about 1, 2, 3, 4, 5, 6, 7, 7.5, 8, 8.5, 9, 9.5, 10, 10.5 or 11. In this case it is, preferable that the biological entity be stable at the pH of the pH-adjusted precursor material.

As another alternative, step a) may comprise:

j) addition of the biological entity to the solution of the surfactant; and k) addition of a precursor material, with pH adjusted to between approximately 1 and about 11, for example about 7.5 and about 11, such that the polar phase of the emulsion comprises the precursor material and the biological entity.

The precursor may comprise a ceramic precursor. It may comprise colloidal silica or some other ceramic precursor, or may be a mixture of two or more different ceramic precursors. The biological entity may comprise a protein. It may comprise an enzyme. The process may additionally comprise adding a gelation aid before step b). The gelation aid may comprise a salt (e.g. sodium chloride) and/or a water soluble polymer. The gelation aid may be added in solution, optionally in aqueous solution. The process may comprise at least partially separating the particles from the non-polar phase. The step of at least partially separating may comprise the step of combining the emulsion comprising the particles with a precipitating solvent so as to precipitate the particles, said precipitating solvent being miscible with the non-polar solvent. A suitable precipitating solvent may be acetone, ethanol or a mixture of these. The precipitating solvent may be chosen so as to not denature or otherwise damage the biological entity. The step of at least partially separating may additionally or alternatively comprise centrifuging the emulsion comprising the particles. After the step of at least partially separating, the particles may be dried.

Thus in one embodiment, the process comprises:

addition of a biological entity to a precursor material comprising at least one alkoxide selected from a zirconium tetraalkoxide and a titanium tetraalkoxide, with pH adjusted to between approximately 2 and about 4; and addition of the biological precursor material mixture to a solution of surfactant to form an emulsion comprising a polar phase dispersed in a non polar phase wherein the polar phase comprises the biological entity and precursor materials; and forming particles comprising the biological entity from the polar phase.

In another embodiment the process comprises:

addition of the biological entity in aqueous solution to the solution of the surfactant to form an emulsion comprising a polar phase dispersed in a non-polar phase, wherein the polar phase comprises the biological entity;

addition of a precursor material comprising a silicate, with pH adjusted to between approximately 8 and about 10, such that the polar phase of the emulsion comprises the precursor material and the biological entity adjusting the pH to between about 6 and about 8; and forming particles comprising the biological entity from the polar phase.

In an embodiment the process comprises:

a) combining the solution of the surfactant in the non-polar solvent with colloidal silica to form an emulsion, said emulsion having a polar phase dispersed in the non-polar phase;

b) adjusting the pH of the emulsion to a pH between about 5 and about 11;

c) combining the emulsion with the biological entity such that the polar phase comprises the biological entity; and d) forming particles composing the biological entity from the polar phase.

In another embodiment the process comprises:

a) combining the solution of the surfactant in the non-polar solvent with an aqueous acid to form an emulsion, said emulsion having a polar phase dispersed in the non-polar phase;

b) adding colloidal silica to the emulsion such that the pH of the emulsion is between about 5 and about 11;

c) adding the biological entity to the emulsion such that the polar phase comprises the biological entity; and d) forming particles comprising the biological entity from the polar phase.

In another embodiment the process comprises:

a) combining the precursor material and the biological entity to form a polar mixture;

b) adjusting the pH of the polar mixture to between about 7.5 and about 11;

c) combining the polar mixture with the solution of the surfactant to form the emulsion having a polar phase dispersed in the non-polar phase, said polar phase comprising the polar mixture; and d) forming particles comprising the biological entity from the polar phase.

In another embodiment the process comprises:

a) combining the solution of the surfactant in the non-polar solvent with a solution or suspension comprising the biological entity;

b) adjusting the pH of a precursor material to between about 7.5 and about 11;

c) adding the pH-adjusted precursor material to the solution comprising the biological entity to form an emulsion comprising a polar phase dispersed in a non-polar phase, said polar phase comprising the biological entity and the precursor material; and d) forming particles comprising the biological entity from the polar phase.

In another embodiment of the first aspect, there is provided a process for releasably encapsulating a biological entity comprising:

combining a precursor material, a surfactant and a non-polar solvent to form an emulsion comprising emulsion droplets dispersed in the non-polar solvent, said emulsion droplets comprising the precursor material;

adding the biological entity to the emulsion; and forming particles from the emulsion droplets, said particles having the biological entity therein and/or thereon.

The step of combining the precursor material, the surfactant and the non-polar solvent may comprise combining the surfactant and the non-polar solvent (e.g. dissolving the surfactant in the non-polar solvent) and then adding the precursor.

The precursor material may be a solution, a suspension, a dispersion, a sol or an emulsion, and may be capable of forming the particles. It may be polar. It may be aqueous. The step of forming particles may comprise the steps of:

optionally, adjusting the pH of the emulsion droplets to a pH at which the biological entity is stable and/or active; and waiting for sufficient time for the emulsion droplets to form the particles.

The step of forming particles may comprise destabilizing and/or gelling and/or aggregating the precursor material. The precursor material may comprise water, and may be an aqueous solution, suspension, dispersion, emulsion or sol. It may comprise a ceramic precursor material (i.e. a precursor to a ceramic material). The ceramic precursor material may comprise a metal oxide precursor material, for example a water soluble salt of a metal oxo anion. The metal oxo anion may be for example silicate, aluminate, titanate, zirconate or some other oxo anion. The ceramic precursor may comprise a silica precursor material such as colloidal silica or silica sol or an alkoxysilane (e.g. a tetraalkoxysilane such as tetramethylsilane) or a metal silicate (e.g. sodium silicate) or a mixture of any two or more of these. It may comprise any hydrous metal oxide which is capable of forming a stable colloidal dispersion. The oxide may be an oxide of a Group 2 to 4 element, including transition elements and lanthanides. The precursor material may comprise primary particles, and the primary particles may be between about 5 and about 500 nm in diameter, or between about 5 and about 100 or about 5 and about 50 nm. It may comprise a mixture of different sized primary particles, and the different sized primary particles may be combined before the step of combining the precursor material with the solution of surfactant. The precursor material may be alkaline, and may have a pH between about 9 and about 12, or it may be acidic, and may have a pH between about 0.5 and about 3.5 or between about 3.5 and about 5.5, or it may have some other pH. The surfactant may be anionic, cationic, non-ionic or zwitterionic, and may be soluble in the non-polar solvent. The emulsion may be a water-in-oil (W/O) emulsion. It may have a droplet size between about 0.01 and about 500 microns. The sufficient time for the emulsion droplets to form the particles may be between about 1 minute and 24 hours, or between about 1 and 12 hours. During the formation of the particles from the emulsion droplets, the emulsion may to be stirred, swirled or otherwise agitated.

The step of combining may comprise stirring, shaking, mixing, swirling or agitating. It may comprise combining the precursor material with a solution of the surfactant in the non-polar solvent. The step of adding the biological entity may be conducted at low shear. The low shear may be sufficiently low to avoid harming, for example denaturing, the biological entity. The biological entity may be added in solution or in suspension. The biological entity may be a biomolecule, and may be for example a protein, a peptide, an antibody, an enzyme, a polysaccharide, a DNA or RNA strand or fragment, or some other biomolecule.

The particles may be mesoporous, and may have an average pore size between about 1 and about 50 nm diameter. They may comprise aggregates each of which comprises a plurality of primary particles. The particles may have a mean particle size between about 0.05 and about 500 microns, or between about 0.05 and about 100 microns, or between about 0.5 and about 50 microns. The particles may have a broad, intermediate or narrow particle size distribution.

The process may additionally comprise one or more of the following steps:

adding a gelation aid before, after or during the step of adding the biological entity;

at least partially separating the particles from the non-polar solvent;

washing the particles; and drying the particles.

The gelation aid may be in sufficient amount to aid formation of spherical particles. It may be added in solution, and the solution may also comprise the biological entity. The gelation aid may be a water soluble salt, for example sodium chloride. Alternatively it may be some other material, for example a water soluble polymer such as hydroxymethylcellulose or hydroxypropylcellulose. The gelation aid may be added in solution, for example aqueous solution, in a concentration of between about 0.1 and 40% w/v. If the gelation aid is a salt, the solution of the salt may be between about 0.5 and 6M. The step of at least partially separating may comprise centrifuging, filtering, microfiltering, sedimenting or some other suitable method. The step of washing may comprise washing with a washing solvent, which may be an organic solvent, for example the non-polar solvent or a solvent miscible with the non-polar solvent, or it may be a polar solvent, for example a polar organic solvent, water or an aqueous solution. The step of washing may be repeated and each repeat may use the same or a different washing solvent. Each washing step may be followed by a step of at least partially separating the particles from the washing solvent, for example by filtering or centrifuging. The step of drying may comprise exposing the particles to a stream of gas, for example air, oxygen, nitrogen, carbon dioxide or some other gas that does not damage or denature the biological entity. The step of drying may be conducted at ambient temperature or at a different temperature that does not damage or denature the biological entity, it may additionally or alternatively comprise applying a vacuum to, or freeze drying, the biological entity.

In an embodiment there is provided a process for releasably encapsulating a biomolecule comprising:

combining a precursor material and a solution of a surfactant in a non-polar solvent to form an emulsion comprising emulsion droplets dispersed in the non-polar solvent, said emulsion droplets comprising the precursor material;

optionally adjusting the pH of the emulsion droplets;

adding the biological entity and optionally a gelation aid to the emulsion;

waiting for sufficient time for the emulsion droplets to form the particles, said particles having the biological entity therein and/or thereon;

at least partially separating the particles from the non-polar solvent;

washing the particles; and drying the particles.

The step of adjusting the pH of the emulsion droplets may be performed before, at the same time as or after the step of adding the biological entity. The soluble salt, if added, may be added before, at the same time as or after adding the biological entity.

In another embodiment there is provided a process for releasably encapsulating a biomolecule comprising:
- combining colloidal silica and a solution of a surfactant in a non-polar solvent to form an emulsion comprising emulsion droplets dispersed in the non-polar solvent, said emulsion droplets comprising the colloidal silica;
- adding a pH adjusting reagent to the emulsion to adjust the pH to between about 5 and 11; and
- adding a solution or a suspension of the biomolecule;
- adding a solution of a soluble inorganic salt; and
- waiting for between about 1 and about 12 hours to allow formation of silica particles from the emulsion droplets, said silica particles having the biomolecule releasably encapsulated therein and/or thereon. The biomolecule may be for example a protein, a peptide, a DNA fragment, an antibody or a polysaccharide.

In another embodiment there is provided a process for releasably encapsulating a biomolecule comprising:
- combining colloidal silica and a solution of a surfactant in a non-polar solvent to form an emulsion comprising emulsion droplets dispersed in the non-polar solvent, said emulsion droplets comprising the colloidal silica;
- adding a pH adjusting reagent to the emulsion to adjust the pH to between about 5 and about 10;
- adding a solution or a suspension of the biomolecule;
- adding a solution of a soluble inorganic salt;
- waiting for between about 1 and 12 hours to allow formation of silica particles from the emulsion droplets, said silica particles having the biomolecule releasably encapsulated therein and/or thereon;
- at least partially separating the silica particles from the non-polar solvent;
- washing the silica particles with the non-polar solvent;
- optionally washing the silica particles with a solvent that is different from the non-polar solvent; and
- drying the silica particles.

In a second aspect of the invention there is provided a particle comprising a releasable biological entity, said particle having an average pore size between about 1 and 60 nm diameter and a mean particle size between about 0.05 and about 500 microns or between about 0.05 and about 100 microns. There is also provided a plurality of said particles. The biological entity may be distributed substantially homogeneously through the particle, or may be distributed inhomogeneously therethrough. The particle may be such that the biological entity is biologically active following release from the particle. For example, if the biological entity is an enzyme, the enzyme may retain its enzymatic activity following release from the particle. The biological entity may retain at least about 50% of its activity prior to encapsulation following release from the particle, or at least about 60, 70, 80 or 90% of its activity.

The particle may be made by a process comprising:
a) combining a solution of a surfactant in a non-polar solvent with a precursor material and the biological entity to form an emulsion, said emulsion having a polar phase dispersed in a non-polar phase, and said polar phase comprising the biological entity; and
b) forming particles comprising the biological entity from the polar phase.

It may be made by the process of the first aspect of the invention.

The particle may comprise an aggregate of primary particles between about 5 and 500 nm in diameter. The particle may have the biological entity releasably encapsulated therein and/or thereon. The particle and the primary particles may comprise a ceramic and may comprise a metal oxide, for example silica, zirconia, alumina, titania or a mixture of any two or more of these, or may comprise a mixed metal oxide of any two or more of silicon, titanium, zirconium and aluminium. The particle may be mesoporous, and may have an average pore size between about 1 and 50 nm diameter. It may comprise an aggregate which comprises a plurality of primary particles. The particle may have a mean particle size between about 0.05 and about 500 microns, or between about 0.5 and about 50 microns. The biological entity may be a biomolecule, and may be for example a protein, a peptide, an antibody, an enzyme, a polysaccharide, a DNA or RNA strand or fragment, or some other biomolecule.

In a third aspect of the invention there is provided a ceramic particle having a biological entity releasably encapsulated therein and/or thereon, said ceramic particle being made by the process of the first aspect of the invention.

In a fourth aspect of the invention there is provided a method for delivering a biological entity to a patient comprising administering to the patient one or more particles according to the second or the third aspect of the invention. The method may be for the purposes of treating a condition, such as a disease, in the patient, whereby the biological entity is indicated in treating the condition. The biological entity may be indicated for treatment of the condition. The administering may be by injection, for example intravenous, intramuscular, subdermal or some other type of injection or may be by means of pulmonary, nasal, oral or transdermal delivery or some other suitable delivery method. The method may comprise suspending the one or more particles in a clinically acceptable carrier, said carrier being suitable for injection or for pulmonary, nasal, oral or transdermal delivery.

In a fifth aspect of the invention there is provided a method for delivering a biological entity to a liquid comprising exposing the liquid to one or more particles according to the second or the third aspect of the invention. In this aspect the biological entity may be for example an enzyme. The biological entity may catalse a reaction in the liquid.

In a sixth aspect of the invention there is provided the use of a particle, or particles, according to the second or third aspect of the invention for delivering the biological entity to either a patient or a liquid. The use may be for the purpose of treating a condition in the patient, or for catalyzing a reaction in the liquid or for some other purpose. The use may comprise controlled release of the biological entity to the patient or to the liquid.

In a seventh aspect of the invention there is provided the use of a particle, or particles, according to the second or third aspect of the invention for the manufacture of a medicament for the treatment of a condition in a patient. The biological entity may be indicated for said treatment. The patient may be an animal or human patient, and the animal may be a mammal, a primate a bird or some other animal.

In an eighth aspect of the invention there is provided a medicament for treating a condition in a patient, said medicament comprising a particle according to the present invention, or a plurality of said particles, wherein the biological entity of said particle or particles, is indicated for treatment of the condition. The medicament may also comprise one or more clinically acceptable carriers and/or adjuvants. It may be suitable for injection into the patient, or for pulmonary, nasal, oral or transdermal delivery to the patient. The carriers and/or adjuvants may be suitable for injection into the patient, or for pulmonary, nasal, oral or transdermal delivery.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENTS

Figure 1:
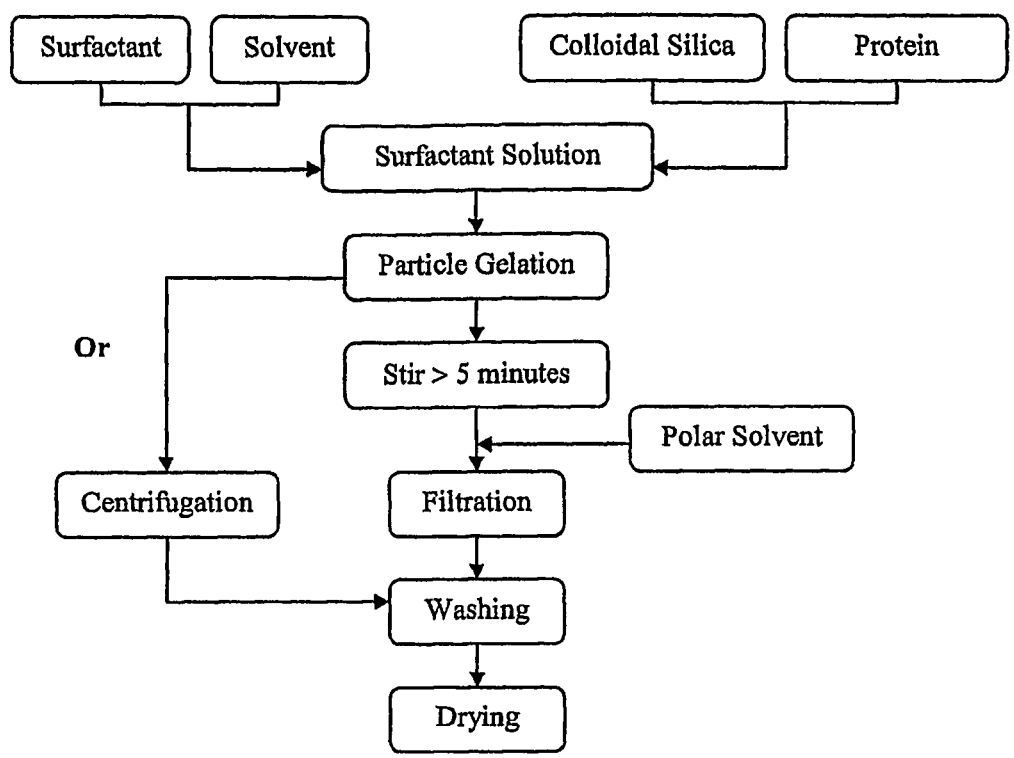
FIG. 1 shows a flowchart showing the process of particle formation at pH ~10.

The present invention relates to the encapsulation and release of biological entities (for example biomolecules and/or microorganisms) in particles. In one example, the particles comprise sol-gel silica derived from aqueous colloidal silica and/or a silicate salt solution. Near neutral pH and the absence of organic chemicals are relatively benign conditions which may assist in retaining the native structure of the biological entity. In the case where a silica sol is used as precursor, the gel may be mesoporous as a result of aggregation of silica primary particles, the size of which determines the pore dimension, thus enabling tailoring of the gel porosity. This control of porosity provides the potential for controlled release applications, if the particle size and shape can also be controlled. By aggregating protein-doped colloidal silica inside a water-in-oil emulsion, the inventors have produced controlled size spheres which may be used for controlled release of biological entities such as biomolecules (e.g. proteins). The process of the present invention may produce particles in which the biological entity is substantially homogeneously distributed through the particle. This may facilitate controlled release of the biological entity.

Important considerations for selecting suitable solvent/surfactant mixtures for use in the present invention are to minimise disruption to the biological entity and to avoid materials which could interact significantly with the colloidal nanoparticles. The non-polar solvent may have a melting point below the temperature at which the biological entity decomposes; denatures or deteriorates. That temperature will depend on the nature of the biological entity. The melting point may be below about 60° C., or below about 55, 50, 45, 40 or 35° C. Suitable solvents which may be used include alkanes, for example long chain alkanes. The alkanes may be linear, branched or cyclic. They may have between about 5 and 24 carbon atoms, or between about 10 and 24, 20 and 24, 5 and 20, 5 and 10 or 10 and 20 carbon atoms, and may have about 5, 6, 7, 8, 10, 12, 14, 16, 18, 20, 22 or 24 carbon atoms. The solvent may be a mixture of different compounds, for example a mixture of different alkanes. Solvents which may be used include dodecane, kerosene, n-hexane, cyclohexane and toluene. Other solvents that may be used include halogenated solvents. The solvent may be a low polarity solvent and commonly is a solvent for surfactant. The solvent should not denature the biological entity or otherwise cause it to deteriorate or decompose. It should not react with the biological entity under conditions pertaining during the process of the present invention. The solvent may be chosen in order to have low cost.

Surfactants containing sufficiently long polyethoxy (—O—$CH_2$—$CH_2$—) chains (such as Brij52) have been found to prevent formation of silica spheres. The inventors hypothesise that this may be due to hydrogen bonding to the primary particle surface, thereby providing a steric barrier which prevents aggregation and gelation. Suitable surfactants for use in the present invention may be anionic, cationic, non-ionic or zwitterionic, and may for example include sorbitan esters such as Span 20 and sulfosuccinates such as Aerosol OT. Non-ionic surfactants or ionic surfactants with the same charge sign (i.e. positive or negative) as the colloidal particles at the pH of gelation are preferred. Thus when the particles are formed at low pH (e.g. less than about pH 8) it is commonly advisable to avoid surfactants having long polyethoxy (—O—$CH_2$—$CH_2$—) chains. When particles are formed at higher pH (e.g. above about pH 8), certain surfactants having polyoxyethylene chains have been found to produce suitable particles. The pH of gelation may depend on the nature of the precursor material.

The precursor material may be a silica sol or colloidal silica and may additionally or alternatively comprise a water soluble salt of a metal oxo anion. The water soluble salt may be a silicate, for example an alkali silicate such as sodium silicate, or may be a zirconate or some other suitable ceramic precursor (i.e. precursor to a ceramic material). A suitable precursor material is Bindzil 30/360 (Eka Chemicals), a colloidal silica which has primary particles around 9 nm, and forms a bulk gel within several hours on lowering the pH from 10 to 6. Other brands of colloidal silica of similar size such as Snowtex ST-40 (Nissan Chemicals) are also suitable. Ludox SM-30 (Grace Davison) may also be used, however it contains a biocide and thus may be unsuitable for some applications of the invention. Precursor materials may have primary particles between about 5 and 500 nm in diameter, or between about 5 and 250, 5 and 100, 5 and 50, 5 and 40, 5 and 30, 5 and 20, 10 and 100, 20 and 100, 10 and 30, 10 and 20, 100 and 500, 100 and 250, 250 and 500 or 50 and 260 nm in diameter, and may have primary particles of about 5, 10, 15, 20, 25, 30, 35, 40, 45, 50, 55, 60, 65, 70, 75, 80, 85, 90, 95, 100, 150, 200, 250, 300, 350, 400, 450 or 500 nm in diameter. A mixture of precursor materials having different sized primary particles may be used. Other precursor materials include aluminates, zirconates, titanates, other metal oxo anions, and mixtures of these.

The process of the invention comprises the step of combining a precursor material and a solution of a surfactant in a non-polar solvent to form an emulsion. The emulsion may be a water-in-oil (W/O) emulsion. It may have a droplet size between about 0.05 and 500 microns, or between about 0.05 and 250 microns, 0.05 and 100 microns, 0.05 and 50 microns, 0.05 and 25 microns, 0.05 and 10 microns, 0.05 and 5 microns, 0.05 and 2 microns, 0.05 and 1 micron, 0.05 and 0.5 microns, 0.1 and 50 microns, 0.5 and 50 microns, 1 and 50 microns, 10 and 50 microns, 25 and 50 microns, 1 and 20 microns, 1 and 10 microns, 1 and 5 microns, 100 and 500 microns, 50 and 500 microns, 250 and 500 microns, 1 and 250 microns, 1 and 100 microns, 1 and 50 microns, 1 and 20 microns, 0.1 and 100 microns, 0.1 and 10 microns or 1 and 2 microns, and may have a droplet size about 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, 300, 350, 400, 450 or 500 microns.

The ratio of surfactant to non-polar solvent may be between about 5 and 30%, or between about 5 and 20, 5 and 15, 5 and 10, 10 and 30, 15 and 30 or 10 and 20%, and may be about 5, 10, 15, 20, 25 or 30% or a w/w or w/v basis. The amount of total water present (which determines the amount of precursor material added) may be between about 2:1 and 10:1 as a mole ratio of water:surfactant, or between about 5:1 and 10:1 or between about 2:1 and 5:1 or between about 3:1 and 7:1, and may be about 2:1, 3:1, 4:1, 5:1, 6:1, 7:1, 8:1, 9:1 or 10:1 as a mole ratio of water:surfactant. The amount of biomolecule added may be dependent on the solubility of the biomolecule in aqueous solution. It may for example be about 20 mg per g of silica. The amount of biomolecule may be between about 1 and 50 mg/g of silica, and may be between about 1 and 20, 1 and 10, 1 and 5, 5 and 50, 10 and 50, 25 and 50, 10 and 40 or 10 and 30 mg/g, and may be about 1, 2, 3, 4, 5, 6, 7, 8, 9, 10, 15, 20, 25, 30, 35, 40, 45 or 50 mg/g silica, or may be some other amount, depending at least in part on the nature of the biological entity and/or the desired release profile thereof.

In the process of the invention, the precursor material is converted into particles having the biological material therein and/or thereon. The particles may be porous and may have pores of average diameter between about 1 and 50 nm, or between about 1 and 2, 1 and 10, 1 and 20, 2 and 50, 2 and 20, 2 and 10, 2 and 5, 5 and 20, 10 and 20, 20 and 50, 10 and 40, 5 and 30 or 5 and 10 nm, and may have pore diameters about 1, 1.5, 2, 3, 4, 5, 6, 7, 8, 9, 10, 11, 12, 13, 14, 15, 16, 17, 18, 19, 20, 25, 30, 35, 40, 45 or 50 nm. The particles may have a diameter (e.g. mean diameter) between about 0.05 and 500 microns, or between about 0.05 and 250 microns, 0.05 and 100 microns, 0.05 and 50 microns, 0.05 and 25 microns, 0.05 and 10 microns, 0.05 and 5 microns, 0.05 and 2 microns, 0.05 and 1 micron, 0.05 and 0.5 microns, 0.1 and 50 microns, 0.5 and 50 microns, 1 and 50 microns, 10 and 50 microns, 25 and 50 microns, 1 and 20 microns, 1 and 10 microns, 1 and 5 microns, 100 and 500 microns, 50 and 500 microns, 250 and 500 microns, 1 and 250 microns, 1 and 100 microns, 1 and 50 microns, 1 and 20 microns, 0.1 and 100 microns, 0.1 and 10 microns or 1 and 2 microns, and may have a diameter about 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, 300, 350, 400, 450 or 500 microns.

Two factors governing the choice of target particle size are:
the primary particles comprising the aggregate may be of comparable size to the biological entity (for example a protein) to be encapsulated. For example the primary particles are about 9 nm for Bindzil 30/360. Consequently a minimum number of primary particles are required to sufficiently encapsulate the biological entity. proteins may comprise both hydrophilic and hydrophobic regions so, although the protein molecules may be located in the water phase of a water-in-oil emulsion, they may be preferentially located near the surfactant/solvent border, forming an outer protein loaded 'shell'. Therefore to minimise excessive dead-space (i.e. space with no associated protein) in the particle, but yet retain sufficient primary particles to retain the protein, a target particle size of about 1 micron may be appropriate.

The inventors have found that addition of a gelation aid to the emulsion may promote the formation of spherical particles in the case of silica. The gelation aid may be a salt, or it may be some other material, for example a water soluble polymer such as hydroxymethylcellulose or hydroxypropylcellulose. The gelation aid may be added in solution, for example aqueous solution, in a concentration between about 0.1 and 40% w/w or w/v, or between about 0.1 and 20, 0.1 and 10, 0.1 and 5, 0.1 and 1, 0.5 and 40, 1 and 40, 5 and 40, 10 and 40, 20 and 40, 1 and 20 or 5 and 20% w/w or w/v, and may be added in a solution with concentration of about 0.1, 0.2, 0.3, 0.4, 0.5, 0.6, 0.7, 0.8, 0.9, 1, 2, 3, 4, 5, 10, 15, 20, 25, 30, 35 or 40% w/w or w/v. The gelation aid may be water-soluble, and may be added in solution, for example in aqueous solution. If the gelation aid is a salt, the solution may be between about 0.5 and 6M in the salt, and may be between about 0.5 and 3, about 0.5 and 1, about 1 and 6, about 3 and 6, about 0.5 and 2 or about 1 and 2M, and may be about 0.5, 0.6, 0.7, 0.8, 0.9, 1, 1.5, 2, 2.5, 3, 3.5, 4, 4.5, 5, 5.5 or 6M in the salt. Inclusion of potassium dihydrogen phosphate (0.0037-0.015 M). with the gelation aid serves to keep the pH in the range 5-7. The concentration of potassium dihydrogen phosphate may be in the range 0.0037-0.01M, 0.0037-0.005M, 0.005-0.015M, 0.01-0.015M or 0.005-0.01M, and may be about 0.0037, 0.004, 0.005, 0.006, 0.007, 0.008, 0.009, 0.01, 0.011, 0.012, 0.013, 0.014 or 0.015M. Other buffer solutions may also be used. The gelation aid may be added before, during, after addition of the biological entity, or together with the biological entry. The amount of gelation aid added varies depending on the nature of the precursor and the aid employed, but in the case of colloidal silica, typically ranges between about 1:10 and 1:200, or between about 1:10 and 1:20 as a mass ratio of gelation aid:silica. The amount of gelation aid may be between about 1:10 and 1:100, 1:10 and 1:50, 1:10 and 1:20, 1:20 and 1:100, 1:50 and 1:100, 1:100 and 1:200, 1:100 and 1:150, 1:150 and 1:200, 1:20 and 1:80, 1:20 and 1:50, 1:10 and 1:15, 1:15 and 120 or 1:13 and 1:17, and may be about 1:10, 1:11, 1:12, 1:13, 1:14, 1:15, 1:16, 1:17, 1:18, 1:19, 1:20, 1:25, 1:30, 1:35, 1:40, 1.45, 1:50, 1:60, 1:70, 1:80, 1:90, 1:100, 1:20, 1:140, 1:160, 1:180 or 1:200 as a mass ratio of gelation aid:silica.

It may be necessary to wait for some time for particles to both form and age so that they may be washed and dried without damage. It may be between about 1 minute and 24 hours, or between about 10 minutes and 24 hours or between about 30 minutes and 24 hours or between about 0.5 and 12 hours or 0.5 and 6 or 1 and 24 or 6 and 24 or 12 and 24 or 1 and 12 or 2 and 8 or 4 and 8 hours or between about 1 and 60 minutes or between about 1 and 30, 1 and 10, 1 and 5, 6 and 60, 5 and 30 or 15 and 30 minutes, and may be about 1, 2, 3, 4, 5, 10, 15, 20, 25, 30, 35, 40, 45, 50 or 55 minutes or about, 1, 2, 3, 4, 5, 6, 7, 8, 9, 10, 11, 12, 16, 20 or 24 hours. During the period of waiting, the emulsion may be stirred, swirled or otherwise agitated, or it may be allowed to rest unagitated.

After the particles have formed and aged, they may be washed. They may be at least partially separated from the non-polar solvent before washing. The stop of at least partially separating may comprise centrifuging, filtering, microfiltering, sedimenting or some other suitable method or a combination of any two or more of these methods. The step of washing may be repeated and may be conducted with different washing solvents in some or all of the repetitions. Washing solvents that may be used include the non-polar solvent, water, alcohols (for example methanol, ethanol, propanol, isopropanol, butanol, isobutanol, depending on the sensitivity of the biological entity), alkanes, halogenated alkanes, ketones, esters and other common solvents, or mixtures of these. The washing may comprise immersing the particles in the washing solvent, and may comprise agitating (for example swirling, shaking, stirring) the washing solvent with the particles immersed therein, and/or may comprise passing the washing solvent through the particles, for example by filtration. It may additionally comprise at least partially separating the particles from the washing solvent.

The particles may be dried, for example in a stream of gas and/or by heating and/or applying a vacuum. The temperature at which the particles are dried may depend on the nature of the biological entity, and should be below the temperature at which the biological entity may be damaged or denatured. The temperature may be for example between about 15; and 50° C., or between about 15 and 40, 15 and 30, 15 and 20, 20 and 50, 30 and 50, or 20 and 40° C., and may be about 15, 20, 25, 30, 35, 40, 45 or 50° C. Alternatively the particles may be freeze-dried. The temperature for freeze-drying may be about −60° C. It may be less than about −30° C., or less than about −40, −50, −60, −70, −90, −100, −120, −140, −160 or −180° C. It may be between about −30 and about −200, or between about −130 and −150, −30 and −100, −30 and −80, −30 and −60, −50 and −100, −50 and −80, −100 and −200, −100 and −150, −150 and −200, −150 and −50 or −70 and −90° C., and may be about −30, −40, −50, −60, −70, −80, −90, −100, −110, −120, −130, −140, −150, −160, −170, −180, −190, −196 or −200° C. The pressure for freeze-drying may for example be between about 1 and about 200 millitorr, or between about 1 and 150, 1 and 100, 1 and 50, 1 and 20 m 1 and 10, 10 and 100, 10 and 50, 50 and 200, 100 and 200, 150 and 200, 100 and 150, 50 and 100 or 120 and 170 millitorr, and may be about 1, 2, 3, 4, 5, 6, 7, 8, 9, 10, 20, 30, 40, 50, 60, 70, 80, 90, 100, 110, 120, 130, 140, 150, 160, 170, 180, 190 or 200 millitorr. The pressure during the drying may be between 0 and 1 atmosphere, or between 0.01 and 1, 0.1 and 1, 0.5 and 1, 0.01 and 0.5, 0.01 and 0.1 or 0.1 and 0.5 atmospheres, and may be about 0.01, 0.05, 0.1, 0.2, 0.3, 0.4, 0.5, 0.6, 0.7, 0.8, 0.9 or 1 atmosphere, or may be at some other suitable pressure.

The particles of the present invention may be used for delivering the biological entity which is encapsulated therein or thereon. The biological entity may be a therapeutic substance, and may be delivered to a patient by administering the particles to the patient. This may be for the purpose of treating a condition for which the biological entity is indicated. The condition may be a disease. Examples of conditions for which biological entities may be indicated include autoimmune diseases, which may be treated by monoclonal antibodies, and cancers, the treatment of which may involve the activation of a prodrug by an enzyme. The administration may be for example by injection of a suspension of the particles in a fluid, or it may be orally, pulmonarily, or by some other route. The patient may be a vertebrate, and the vertebrate may be a mammal, a marsupial or a reptile. The mammal may be a primate or non-human primate or other non-human mammal. The mammal may be selected from the group consisting of human, non-human primate, equine, murine, bovine, leporine, ovine, caprine, feline and canine. The mammal may be selected from a human, horse, cattle, cow, ox, buffalo, sheep, dog, cat, goat, llama, rabbit, ape, monkey and a camel, for example.

The particles of the present invention may also be used to deliver the biological entity to a liquid, for example a reaction mixture. The biological entity may be for example a catalytic substance such as an enzyme, and the particles may be used to deliver the biological entity to a reaction mixture to be catalysed by the catalytic substance. An example is the incorporation of particles comprising a protein-cleaving enzyme such as subtilisin, into a powdered laundry detergent, for subsequent release on dispersal of the detergent. A second example is the incorporation of enzymes commonly used for oral hygiene purposes, such as glucose oxidase, and/or lactoperoxidase, into particles which may be incorporated into toothpaste.

Encapsulation of the biological entity in the particles of the present invention may protect the biological entity from harmful environmental conditions, such as high shear, and thereby provide for easier handing or extended life of the biological entity. The encapsulation may also provide for controlled release of the biological entity, whereby the biological entity is delivered at a controlled rate to a patient or a liquid. The rate may be controlled by controlling the pore size of the particles.

Gelation Process

The inventors have found that gelation occurs spontaneously when colloidal silica is dispersed in a surfactant solution, and particles are formed and aged subsequently in a few minutes. The pH of the initial colloidal suspension is typically about pH 10. It is possible to reduce the pH of the colloidal suspension before addition to the surfactant solution, but there is a limiting pH range (about 7.5-10, depending on the colloidal solution/surfactant/acid employed) over which spherical particles may be formed.

The surfactant used in this process may be for example: NP-5, AOT, Span20, Span40, Span60, Span80, etc. Colloids which may be used include: Ludox SM-30, Ludox HS-40, Bindzil 30/360, Bindzil 15/500, Snowtex 40, Snowtex UP, etc. Preferably, the colloidal particles should be less than about 30 nm in diameter although somewhat larger particles may be used. Colloidal silica and surfactant concentration may be broad, and the solvent may be selected from a range of non-polar solvents.

Properties of Colloidal Silica

Colloidal silica suspensions are made by dispersing negatively charged, amorphous silica particles in water. The particles are generally spherical in shape. $OH^-$ ions exist at the surface of the particles with an electric double layer formed by alkali ions. Stabilization is achieved by the repulsion between the negatively charged particles. Perturbation of the charge balance causes aggregation, resulting in high viscosity and/or gelation of the suspension. Colloidal silica may be destabilised by pH change or addition of salts, electrolytes, organic solvents, or surfactants.

The influence of each of those factors on the gelation time depends on both the characteristic of the sol and the parameter inducing destabilization. For example, the higher the concentration or the smaller the particle size, the greater the effect of pH on the gelation time, i.e. the shorter the gelation time. However, the gelation time differs with the kind of acid used for pH adjustment. Organic acids commonly provide better stability in terms of gelation time, depending on the $SiO_2$ concentration and particle size. For example, under the same $SiO_2$ and acid concentrations, acetic acid leads to slower gelation than a strong acid such as HCl. This may be due to the fact that less $H^+$ is released from a weak acid, thus diminishing the reaction between $H^+$ and $-O^-$ on particle surface.

Synthetic Procedure

An example of a generalised synthesis procedure for forming particles at pH about 10 is outlined in FIG. 1.

0.2 mol/L surfactant solution in 50 mL nopolar organic solvent was prepared. 2.16 mL colloidal silica (pH=9 or above), containing a biological entity, e.g. a protein, was then added at ambient temperature. After stirring for about 10 minutes, 40 mL polar solvent was added to destabilise and dilute the emulsion. The resulting particles were then filtered off, and then rinsed with solvent. The particles were then dried at room temperature.

In a particular example, NP-5 and cyclohexane were used to prepare the surfactant solution, and the colloidal silica was Ludox SM-30. Acetone was used as the polar solvent acetone to destabilize and dilute the emulsion, and to wash particles.

Alternatively, particles containing the biological entity may be centrifuged at 2000 rpm for 3 minutes to remove them from the emulsion, and the particles may then be washed by benign solvents such as kerosene and/or n-hexane. Particles may be dried at room temperature under flowing nitrogen.

Possible Mechanism for Gelation:

In colloidal solution, there are two main forces: the van der Waals force (FVDW) and the electrostatic force (FEL). Total force (FTOT) is the sum of FVDW and FEL (according to DLVO theory). In a colloidal solution containing large polymers, one more force exists, the depletion force, FOS. Under this circumstance, the total force FTOT=FVDW+FEL+FOS. The stability of the colloid may be destroyed by rearranging these forces by changing pH, adding salts or introducing surface active agents, etc.

In a thermodynamically stable microemulsion (W/O) (which typically occurs when the surfactant has an HLB between about 10 and about 13), the interfacial tension is very low. When a colloidal solution is mixed with a microemulsion, the local interfacial force may drive the colloidal silica to aggregate in the water droplets to form large particles. One important factor in this aggregation is the colloid concentration. It is thought that the mechanism for aggregation is as follows. As the colloid suspension is added into surfactant solvent mixture, a hydrophilic domain containing water and colloid is formed. Some of the water molecules will interact with the hydrophilic heads of surfactant molecules forming a hydration layer at the liquid-liquid interface. This results in a number of water molecules being adsorbed and trapped, decreasing the amount of free water in the pool, and thus the concentration of colloid in the water pool is artificially increased, leading to gelation of the colloid. Many parameters can influence the formation of the spherical microparticles; silica concentration in the colloid, surfactant concentration, and water to surfactant molar ratio, amongst others.

To form particles according to this process, the surfactant may need to have a medium strength molecular interaction between its polar head and the water pool. This molecular interaction may be characterised by the surfactant footprint (A), which may be calculated by dividing the surface area of the water droplet surface ($\pi \cdot d^2$, where d is the water pool diameter) by the surfactant aggregation number (N).

$$A = (\pi \cdot d^2)/N$$

Using values from the literature, the footprint was calculated for the range of surfactants used. The results are listed below.

Semi-quantitative Structure Estimation of Liquid-liquid Interface.

Figure 2:
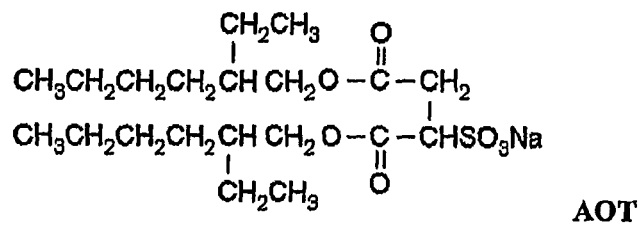
FIG. 2 shows the structures of some surfactants that allow formation of spherical particles at pH ~10.
Figure 2:
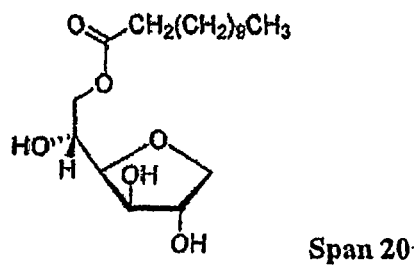
Figure 2:
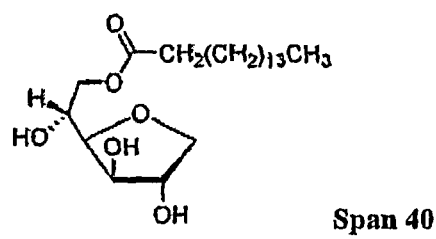
Figure 2:
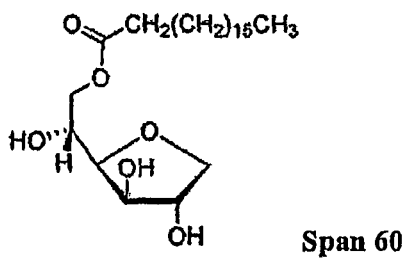
Figure 2:
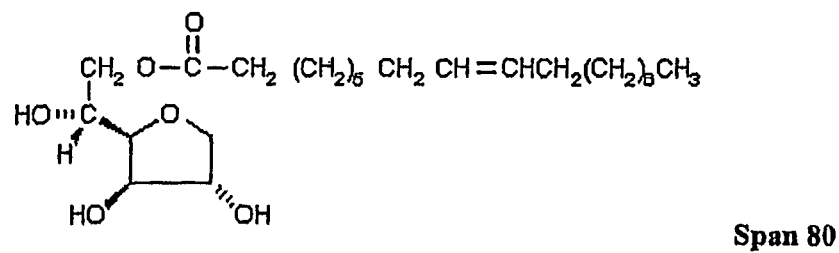

|  | Brij 30 | NP-5 | Triton X-100 | AOT |
| --- | --- | --- | --- | --- |
| Surfactant structure | $C_{12}H_{25}$—$(OCH_2CH_2)_4OH$ | $C_9H_{19}$—$C_8H_4$—$(OCH_2CH_2)_5OH$ | $C_8H_{17}$—$C_8H_4$—$(OCH_2CH_2)_{9.5}OH$ | See FIG. 2 |
| Aggregation Number: N | 150 (R = 6.4)<br>45 (R = 1.61)<br>362 (R = 12.86) | 210 (R = 6) | 140 | 60 (R = 5)<br>130 (R = 10) |
| Reverse micelle diameter | 3 nm (R = 1.34)<br>6 nm (R = 13.4) | 10 nm (R = 6)<br>13 nm | 46.5 nm (R = 5.5) | 4.8 nm (R = 5)<br>6.6 nm (R = 10) |
| Foot print: A ($nm^2$/molecular) | 0.628 (R = 1.61)<br>0.312 (R = 12.86) | 1.50 (10 nm size)<br>2.55 (13 nm size) | 48.5 | 1.20 (R = 5)<br>1.05 (R = 10) |
| Number of surfactant/$nm^2$ | 1.6 (R = 1.61)<br>3.2 (R = 12.86) | 0.67 (10 nm size)<br>0.39 (13 nm size) | 0.021 | 0.83 (R = 5)<br>0.98 (R = 10) |

R: [water]/[surfactant] mol ratio

A medium interaction corresponds to a footprint between about 1 and about 5 $nm^2$ per molecule, which corresponds to about $10^{-2}$ surfactant molecules per 10 $nm^2$. Any surfactant with footprint value less than about 1 $nm^2$ per molecule (e.g. Brij 30) could form an extremely stable microemulsion with small size water pools. Hence, only submicron spherical particles may be produced. An emulsion system with bigger footprint (>about 5 $nm^2$ per molecule) may not be suitable for forming spherical particles by this process.

Another hypothesis is that the oxyethylene units in the surfactant molecule may play a role in the gelation of primary particles to form submicron particles. The oxyethylene units, which form the polar head of the surfactant molecule, may interact with the particle surface by hydrogen bonding, thus influencing the interaction between the silica particle surface and water, which may control the coalescence process. This may explain why at low pH, where the number ratio between (—OH) an (—O$^-$) is higher and hence the hydrogen bonding is stronger, the coalescence of primary colloid is not favoured, and no microparticles are produced.

The above assumption may only be satisfied for microemulsions, i.e. when the surfactant has an HLB from about 10 to about 13. For surfactants with HLB less than about. 9, it is necessary to understand the mechanism of particle formation in a different way, it is widely acknowledged that materials with an HLB value in the range of 3-9 are suitable as emulsifiers for water-in-oil type emulsions or as a wetting agent. All the Span surfactants used have the same hydrophilic head but different lipophilic tails, and their HLB value is between 4.3 for Span 80 and 8.6 for Span 20. Hence a W/O type emulsion is produced by these surfactants. A proposed mechanism is as follows. When colloidal silica aqueous suspension is introduced, it is likely to penetrate through the liquid-liquid interface and form a hydrophilic domain (water droplets), in which the interfacial force disturbs the forces stabilising the colloid. As a result, the colloidal solution gels to form large spheres. A possible explanation for the observation that particles formed by Span 20 are much smoother than those formed by Span 80 is that the HLB of Span 80 is so small that interfacial force is very strong. Once the colloidal suspension encounters the surfactant solution, the gelation rate of colloidal silica is fast, consequently, smaller particles are initially produced. Consequently rough surfaced microparticles are formed via fusion and fission processes of water droplets.

Figure 3:
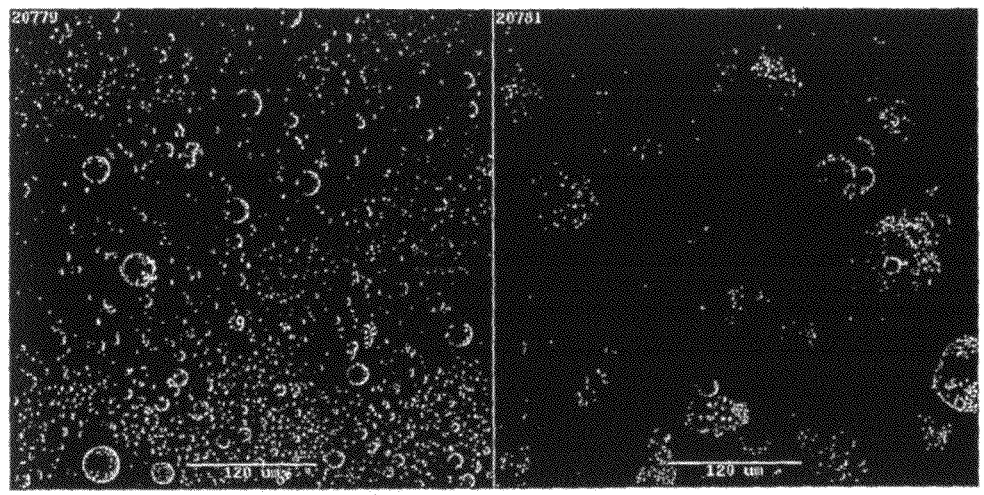
FIG. 3 shows scanning electron micrograph images of silica products produced using various surfactants.
Figure 3:
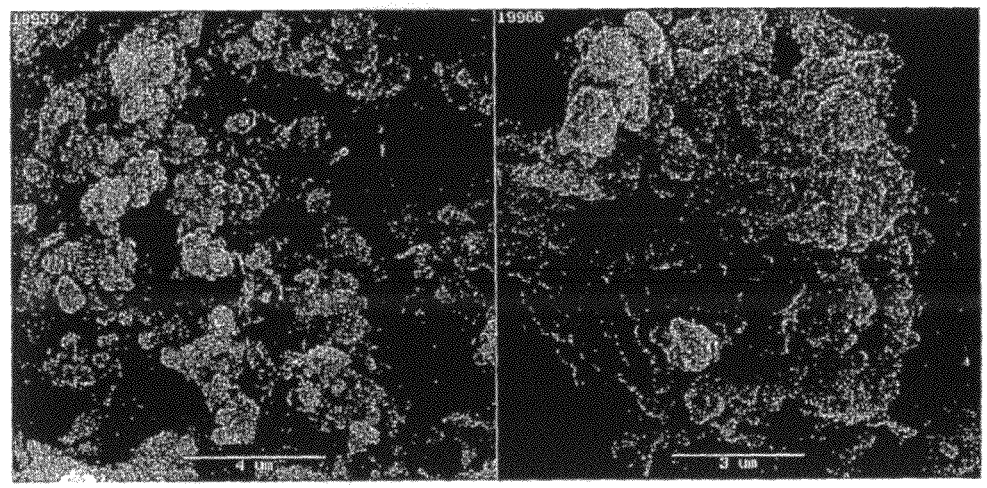
Figure 3:
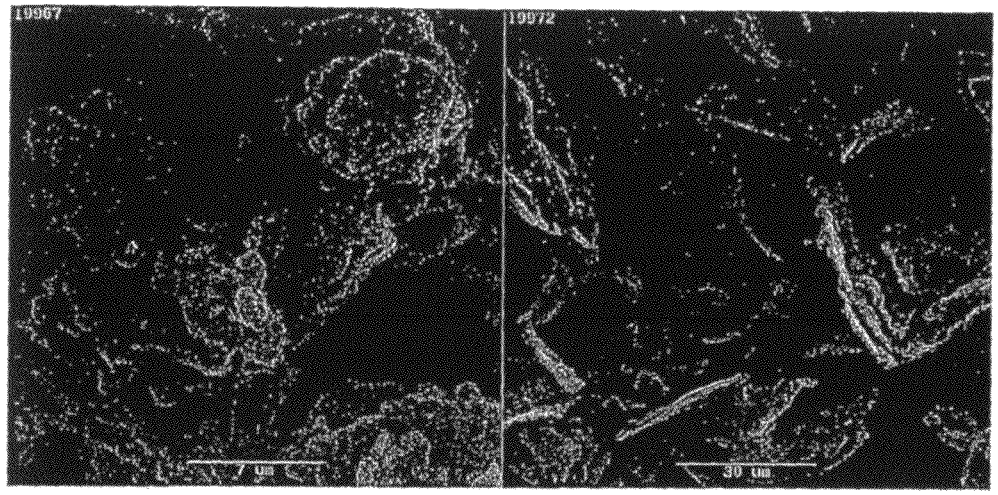
Figure 3:
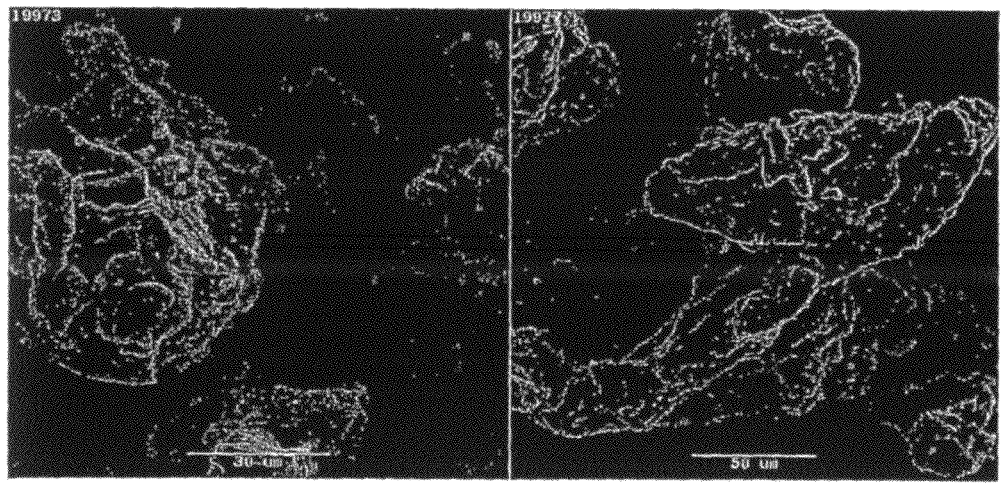

Effect of Surfactant Type:

Surfactants which been tested are listed in the table below. Solutions of 0.2 mol/L surfactant in cyclohexane solution were prepared. For the Triton X-114, NP-9, and Triton X-100 systems, 0.2 mol/L cosurfactant (1-pentanol) was added to promote emulsion stability. Tween and Span surfactants produced unstable emulsions. The procedure was according to typical synthesis process described in FIG. 1, except that 1.08 mL Ludox SM-30 was added as the colloidal silica. The corresponding SEM images are shown in FIG. 3.

Surfactant Properties and Corresponding Products.

| Surfactant | M.W. | HLB | Result |
| --- | --- | --- | --- |
| Brij 30 | 362 | 9.7 | Aggregated particles |
| NP-5 | 440 | 10 | Microparticles |
| NP-6 | 485 | 10.9 | Aggregated particles |
| Triton X-114 | 537 | 12.4 | gel |
| NP-9 | 630 | 13 | gel |
| Triton X-100 | 646 | 13.5 | gel |
| AOT | 445 | 10-15 | Microparticles |
| Tween 21 | 522 | 13.3 | gel |
| Tween 61 | 606 | 9.6 | gel |
| Tween 81 | 650 | 10 | gel |
| Span 20 | 346 | 8.6 | Microparticles |
| Span 40 | 403 | 6.7 | Microparticles |
| Span 60 | 431 | 4.7 | Microparticles |
| Span 80 | 429 | 4.3 | Microparticles |

Spherical microparticles were formed using NP-5, AOT, and the different Span surfactants. The particles formed by Brij 30 and NP-6 appeared to be aggregated. All other systems produced irregular shaped products.

The structures of the surfactants, which lead to formation of spherical microparticles, are listed in FIG. 2. The proposed selection rule will be discussed in the later section based on current experimental results.

Figure 4:
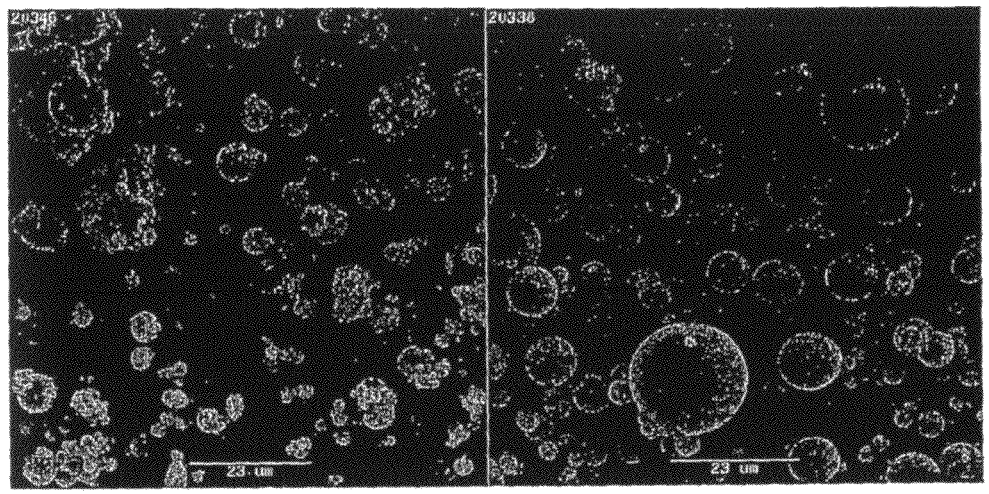
FIG. 4 shows scanning electron micrograph images of silica particles made using various surfactant concentrations.
Figure 4:
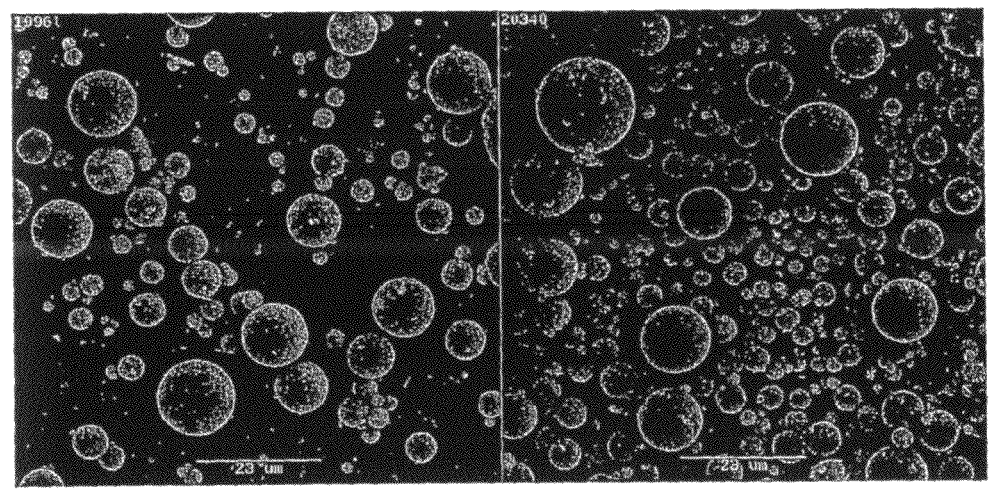
Figure 4:
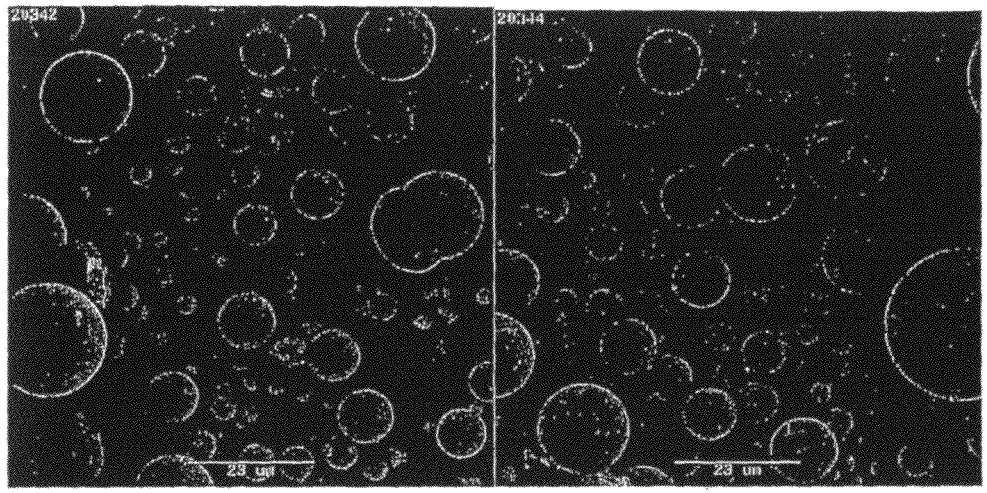

Effect of Surfactant Concentration:

NP-5 was selected as the surfactant to investigate the surfactant concentration effect on particle morphology. The surfactant concentration was varied from 0.05 mol/L to 0.5 mol/L. The corresponding SEM Images are displayed in FIG. 4. It appears to be possible to increase the NP-5 concentration above 0.5 mol/L and still produce spherical particles. However, the minimum surfactant concentration is about 0.1 mol/L: lower concentrations resulted in the production of less spherical particles, with more agglomerated gel products.

Effect of Emulsion Solvent:

Using the typical synthetic procedure outlined in FIG. 1, seven different solvents were used to produce silica particles.

Figure 5:
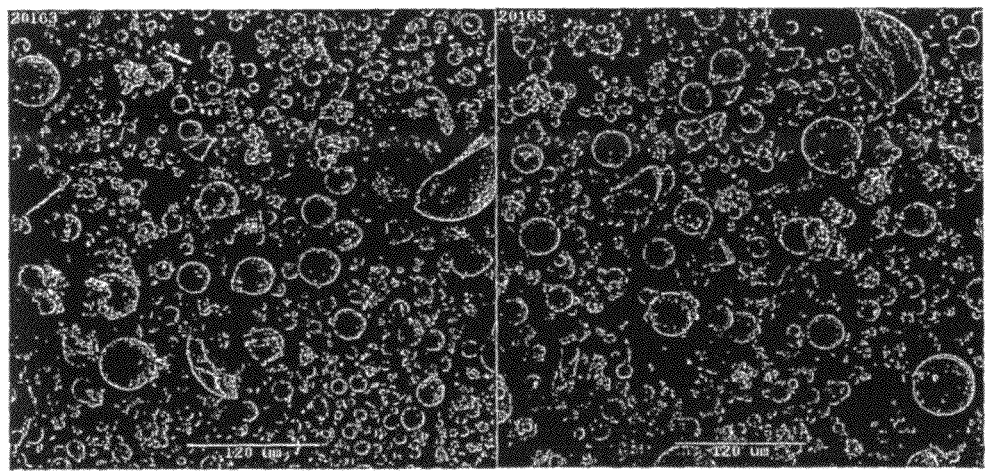
FIG. 5 shows scanning electron micrograph images of silica products made using various emulsion solvents.
Figure 5:
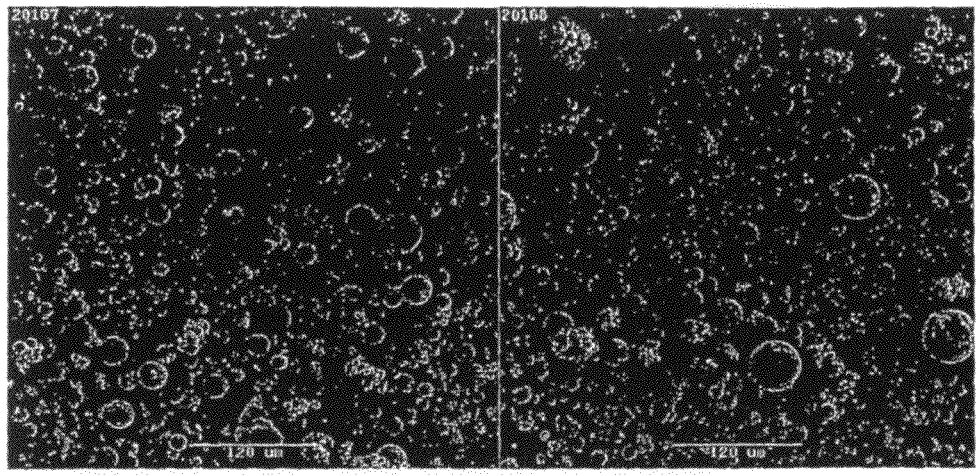
Figure 5:
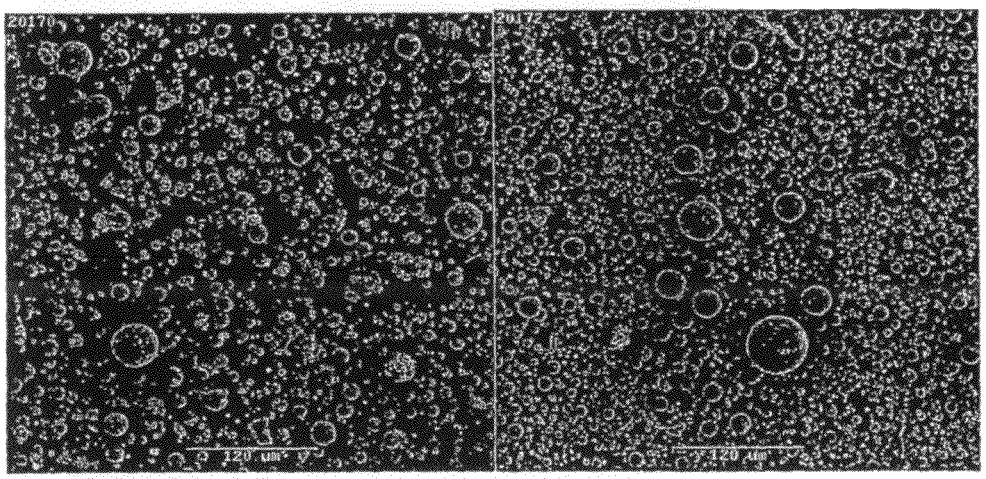

They were: Petroleum Ether (PE: a mixture of low molecular weight hydrocarbons), pentane, hexane, octane, decane, dodecane, kerosene, and cyclohexane. SEM images of the resulting particles are shown in FIG. 5. The images suggest that long chain alkanes such as kerosene (a mixture of medium weight alkanes) produce more spherical particles and it appears that the longer the alkane chain, the smaller the particles produced.

In "*Effect of reaction condition and solvent on the size and morphology of silica powder prepared by an emulsion technique*", W-Kyu Part, et al., *Korean J. Ceram.*, 6, 229-235 (2000), it was demonstrated that the droplet size in the emulsion, and hence the silica gel particulate size, could be significantly influenced by the steric effect of the organic solvent. In order to confirm this, the authors used octane isomers of various structures with the same chemical formula, and a series of $C_nH_{2n+2}$ alkanes to produce emulsions. The average size of particles in the octane isomers and alkane group series decreased with increasing chain lengths, as expected. The average size obtained from iso-octane was 64 μm and that of octane was 46 μm. The average size of the silica gel powder decreased gradually from 75 μm to 28 μm with increasing chain length. The particle sizes obtained from use of n-hexane, n-heptane, n-octane, nonane, and n-decane were 75, 51, 46, 44, and 28 μm, respectively. These figures are consistent with the present results.

In another reference: "*Solvent Effects on Copper Nanoparticle Growth Behaviour in AOT Reverse Micelle Systems*", J. P. Cason, et al., *J. Phys. Chem. B*, 105, 2297-2302, (2001), the copper particle growth was found to be significantly faster in isooctane solvent than in cyclohexane solvent. This reference stated that cyclohexane was able to support a slightly larger terminal particle size than isooctane. This dependence is due to the fact that cyclohexane is able to pack into the micelle tails and effectively solvate the surfactant tails, whereas the bulky nature of isooctane does not allow it to solvate the tails as readily.

Figure 6:
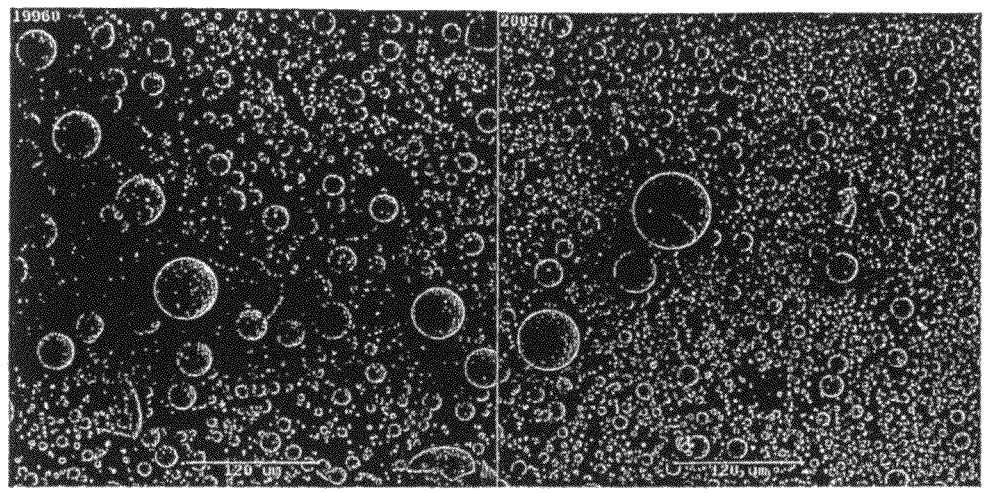
FIG. 6 shows scanning electron micrograph images of silica particles made using various concentrations of Ludox SM-30.
Figure 6:
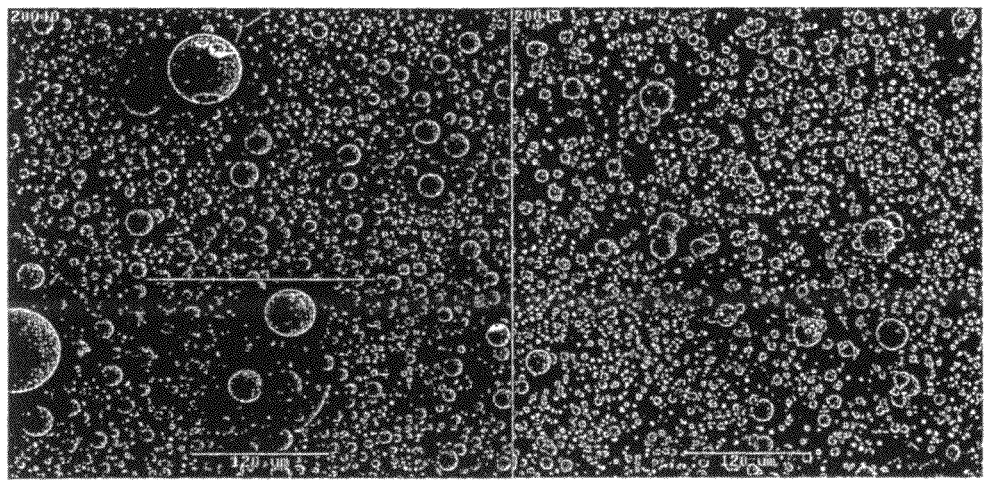
Figure 6:
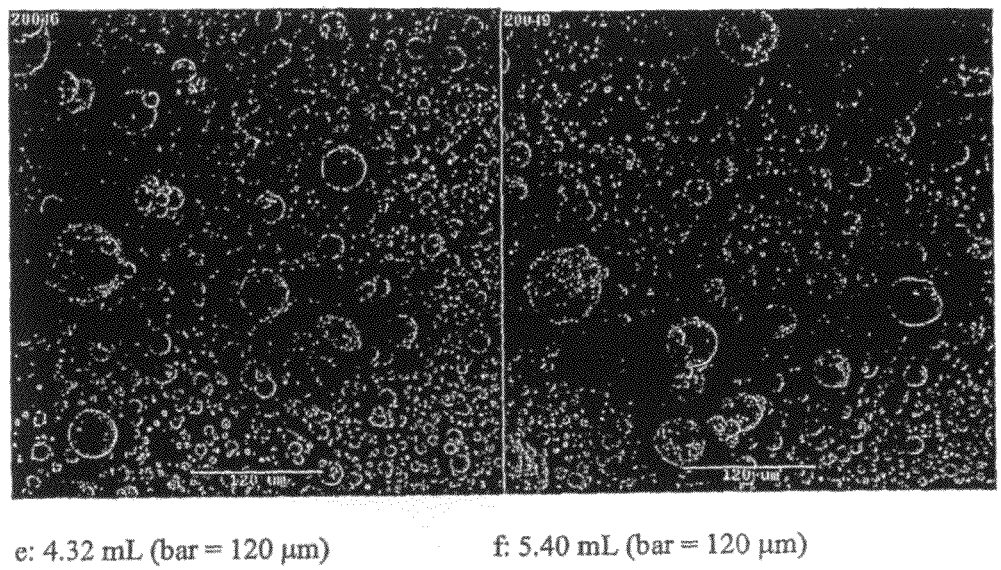

Effect of Colloid Concentration:

Varying amounts of Ludox SM-30 were added to 50 ml of emulsion containing 10 mmol NP-5 to produce silica microparticles. Results are shown in the table below, and SEM images are shown in FIG. 6. It appears from these results that a volume of colloid as high as 5.4 mL produced a predominantly spherical product. It appears that, with increased amounts of colloidal silica, the particles are more likely to aggregate. 2.16 mL colloidal silica was selected for a typical synthesis. It appears that when fewer particles are present in the emulsion, the particles are less likely to collide thus decreasing the probability of forming aggregated products. The result may be due to the fact that the number of surfactant molecules per particle is higher for a smaller number of particles, thus reducing the occurrence of agglomeration.

Figure 7:
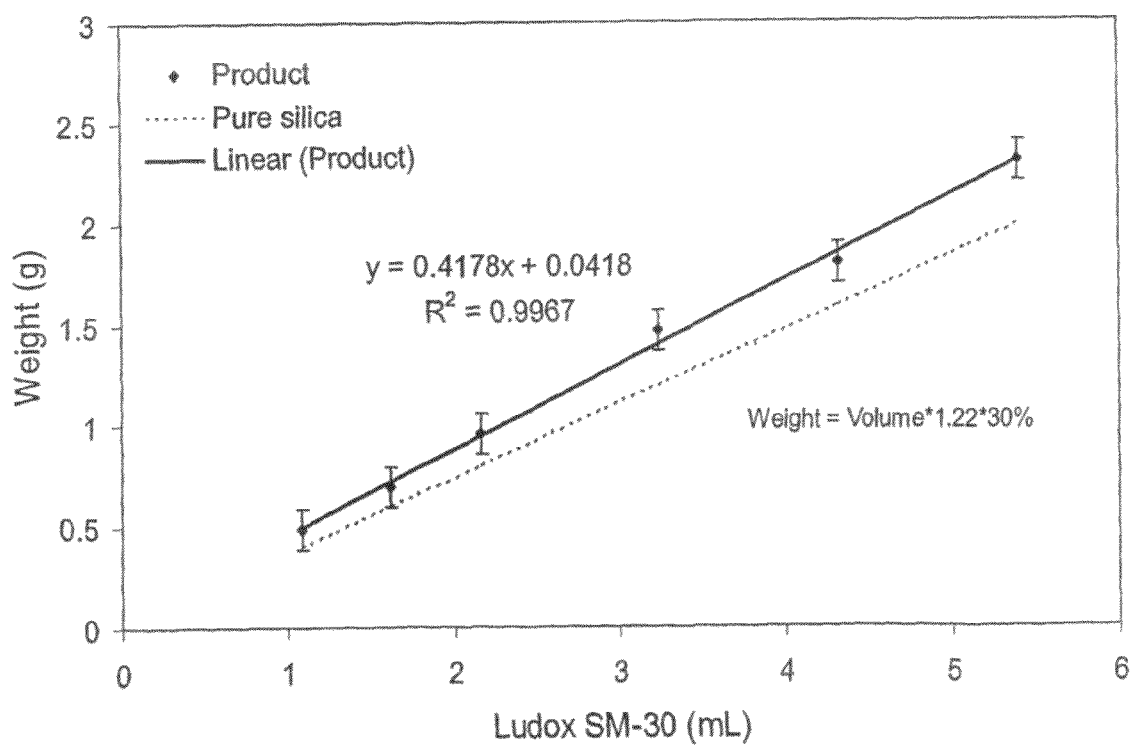
FIG. 7 is a graph showing product yield against the volume of added Ludox SM-30 using the process outlined in FIG. 1.

From FIG. 7, which plots the yield of particles from the process against the amount of silica added initially, it can be seen the product yield is slightly higher than pure silica added initially for Ludox SM-30 (silica: 30 wt. %; density: 1.22 g/cm$^3$). The additional mass may be due to adsorbed surfactant and water. High concentrations of colloidal silica appear to lead to greater weight differences, possibly due to the adsorption of more surfactant.

Figure 8:
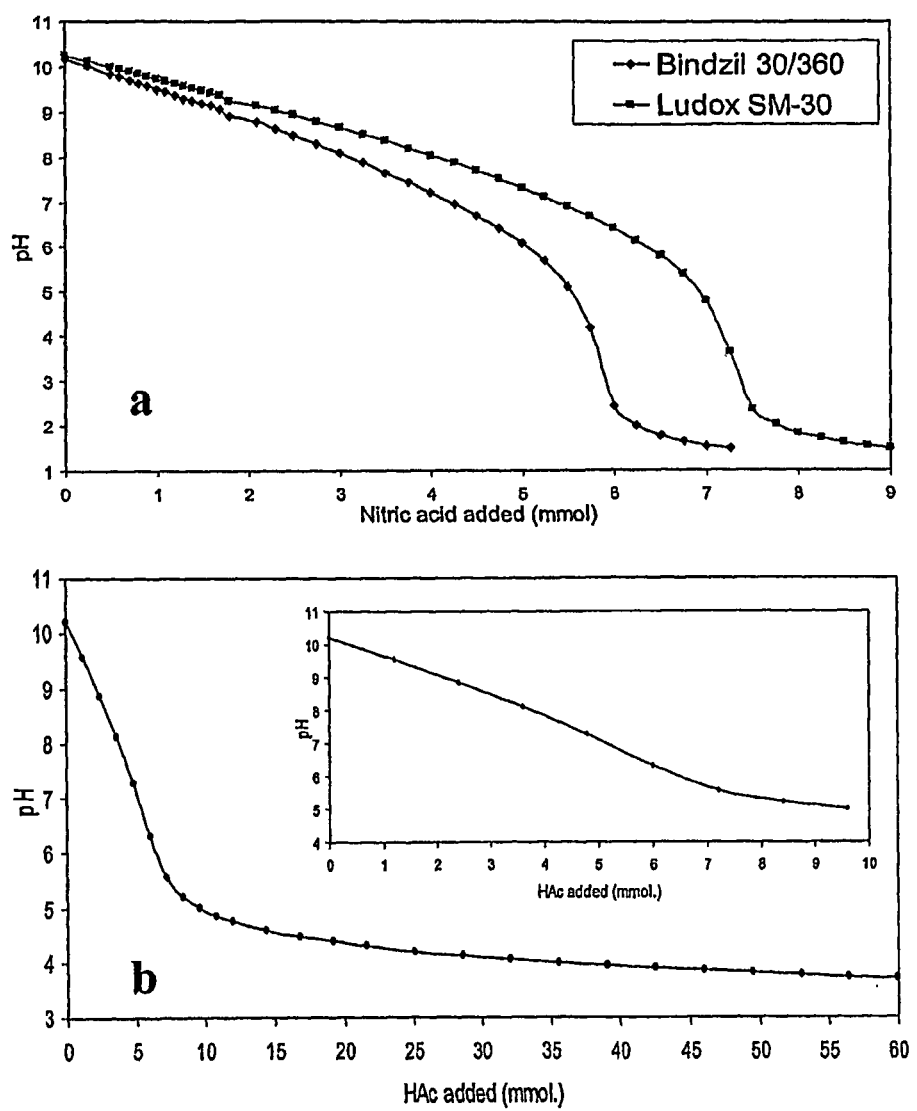
FIG. 8 shows graphs of pH of colloidal silica (30 mL) as a function of acid; (a) Ludox SM-30 and Bindzil 30/360 filtrated by 0.5 mol/L nitric acid; (b) Ludox SM-30 titrated by 12 mol/L acetic acid.

Effect of Colloid pH:

FIG. 8 shows the titration curves of Ludox and Bindzil (pH versus amount of acid added). The pH of Ludox SM-30 (30 mL) and Bindzil 30/360 (30 mL) decreased gradually to about 5.5 with addition of 0.5 mol/L nitric acid. A sharp pH drop occurs for both systems over the pH range 5.5-2.0, after which the pH decreases slowly again. By contrast, when Ludox SM-30 is titrated by 12 mol/L acetic acid, the pH change shows two decreasing rates, the transition between them occurring at around pH 5. No gelation occured for any of the above systems during the titration (about 2 hours). However, when Ludox SM-30 was titrated by 2 mol/L nitric acid, the colloid gelled when 4 mmol $HNO_3$ was added. The pH was 6.65 at that point. This may be due to the colloid concentration effect.

Figure 9:
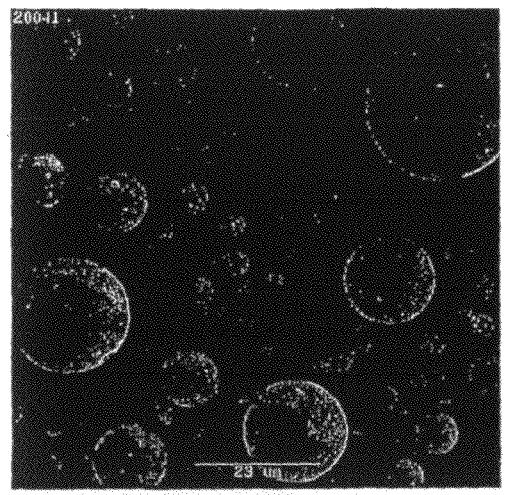
FIG. 9 shows scanning electron micrograph and transmission electron micrograph images of silica products formed using Ludox SM-30 titrated by nitric acid.
Figure 9:
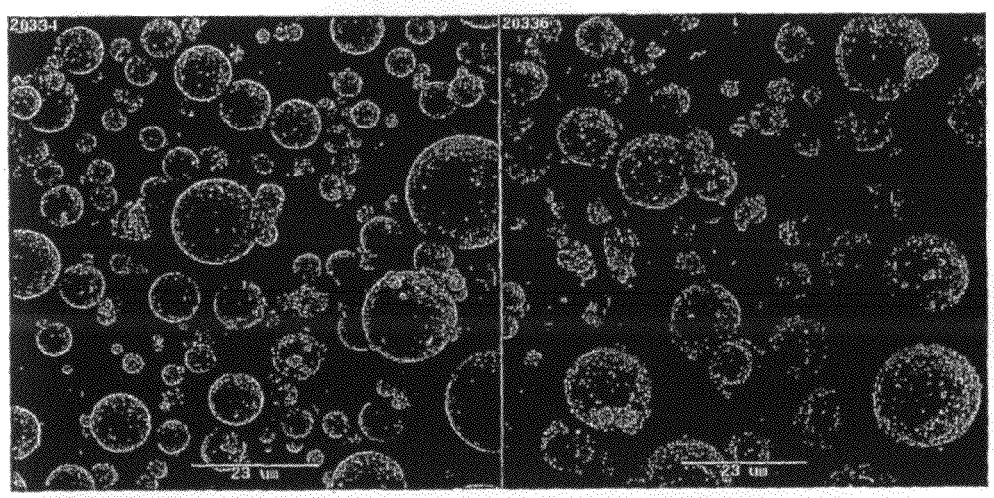
Figure 9:
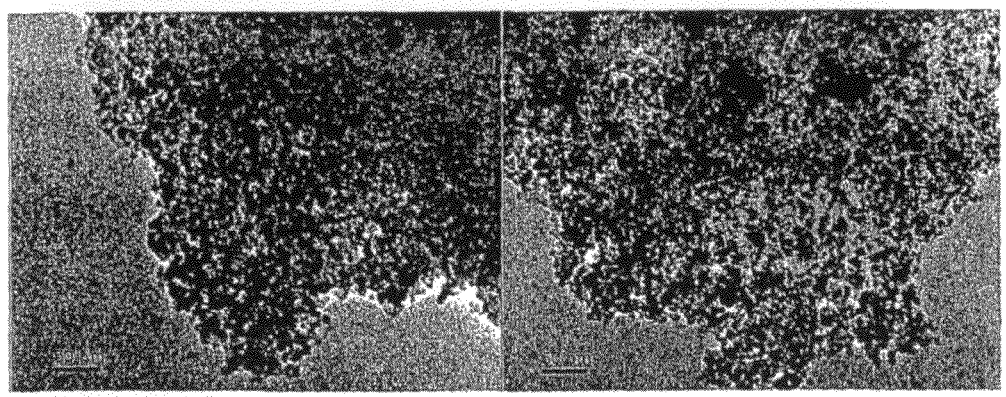

FIG. 9 shows the SEM and TEM images of silica products formed by Ludox SM-30 titrated by nitric acid. When the pH is above 9, spherical particles were produced. Below pH 9, colloidal silica gelled but did not form spherical particles, as shown in FIGS. 9*d* and *e*.

Figure 10:
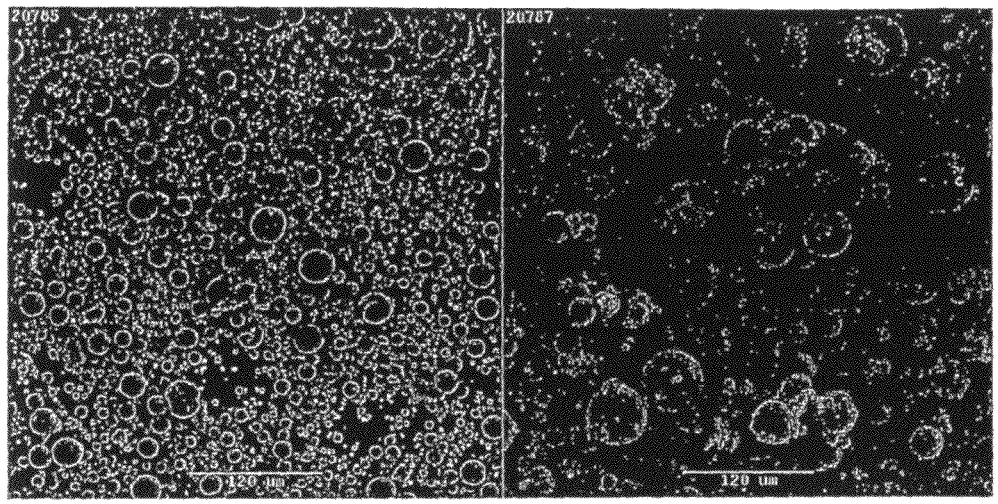
FIG. 10 shows scanning electron micrograph images of silica products formed using Ludox SM-30 titrated by acetic acid.
Figure 10:
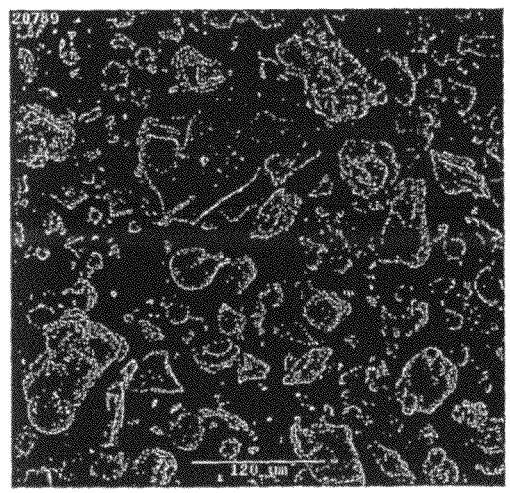

By contrast, if the pH of Ludox SM-30 was reduced using acetic acid, most particles were spherical if the pH was above 9 (FIGS. 10*a* and *b*). This is consistent with the results of titration with nitric acid. This may be because the aggregation of colloid is strongly dependent on the media pH but independent of the nature of the acid used to decrease pH. Irregular shaped products were produced at pH 8.57 (FIG. 10*c*). No solid products were produced at pH: 7.754, 6.707, 5.869 and 5.378.

Figure 11:
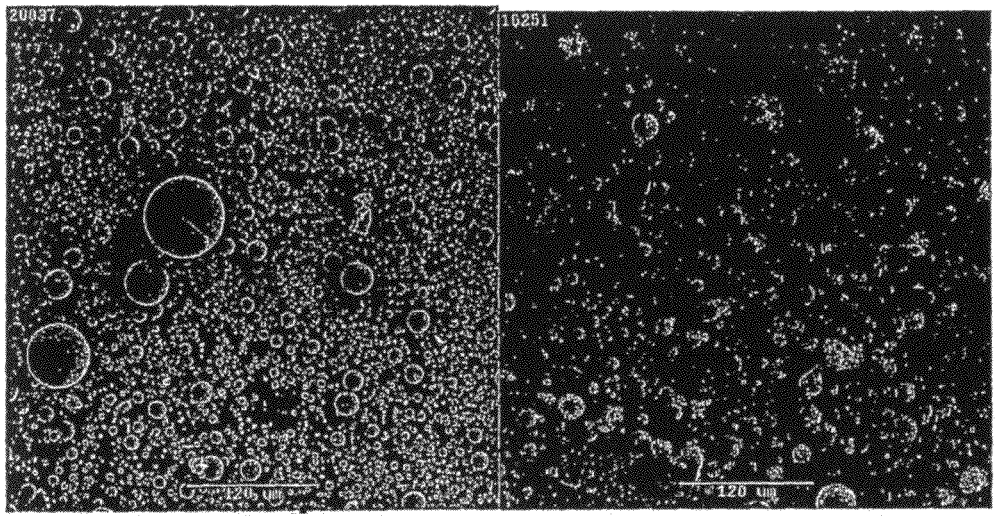
FIG. 11 shows scanning electron micrograph images of silica products formed using various type of colloidal silica.
Figure 11:
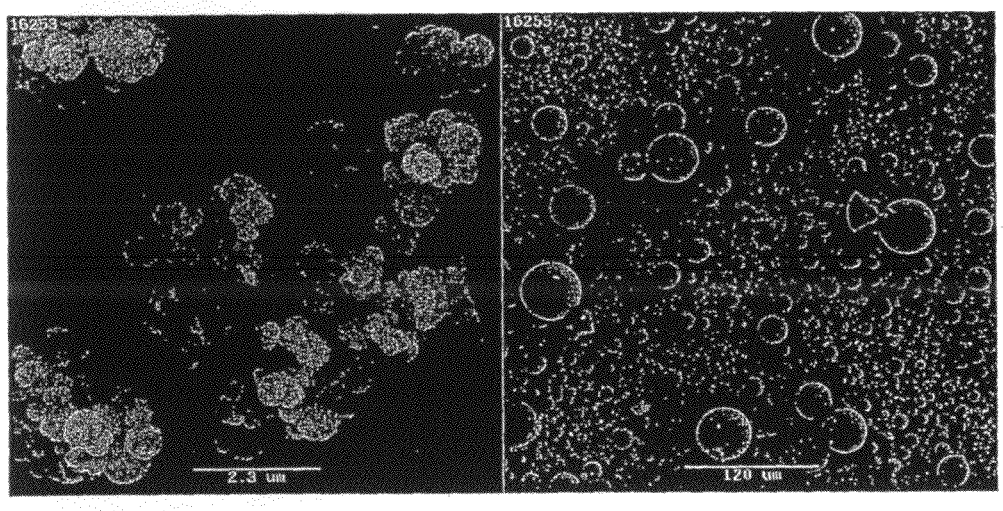
Figure 11:
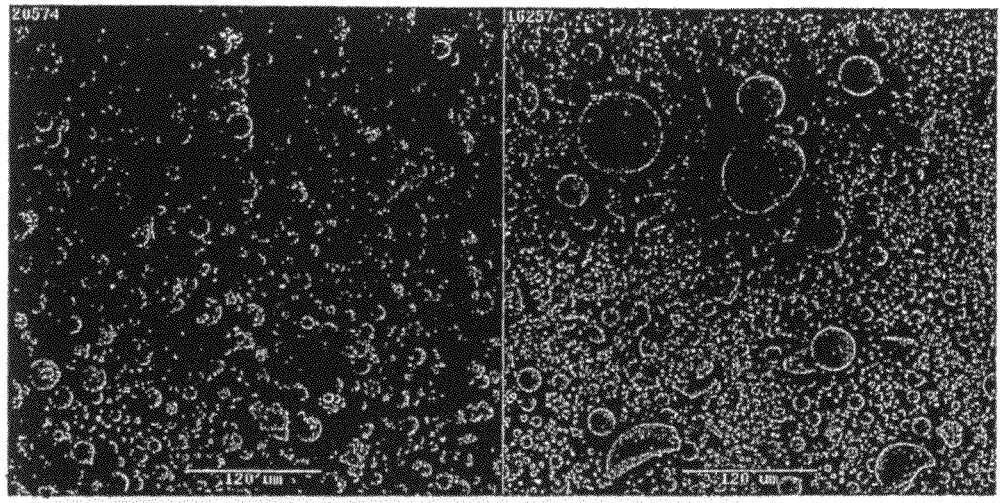
Figure 11:
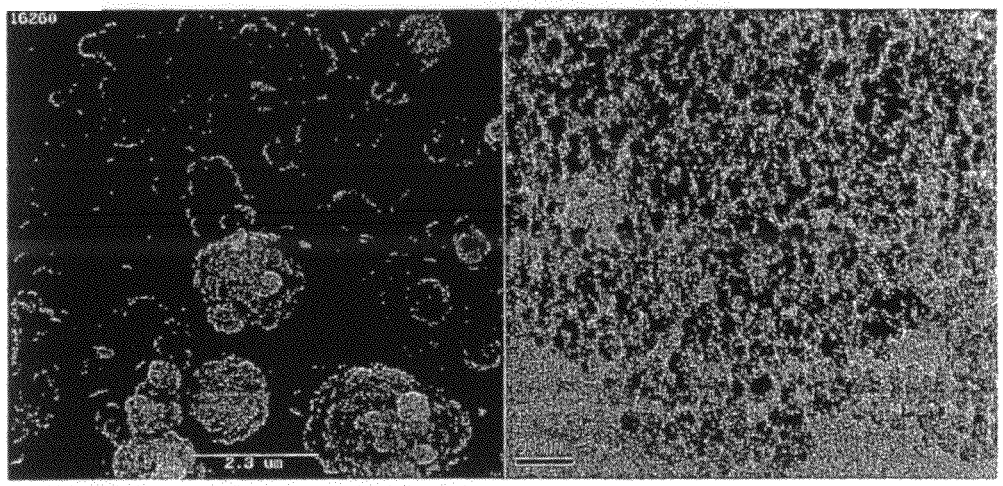
Figure 11:
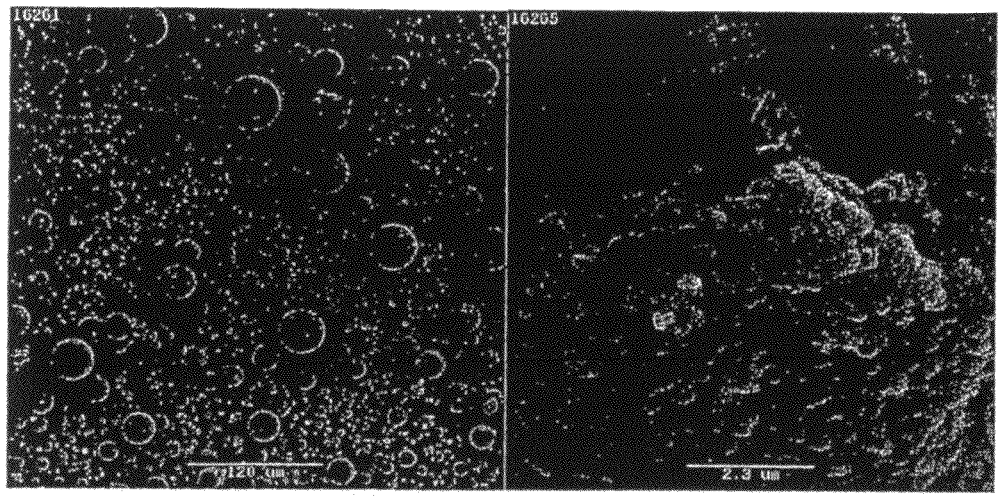
Figure 11:
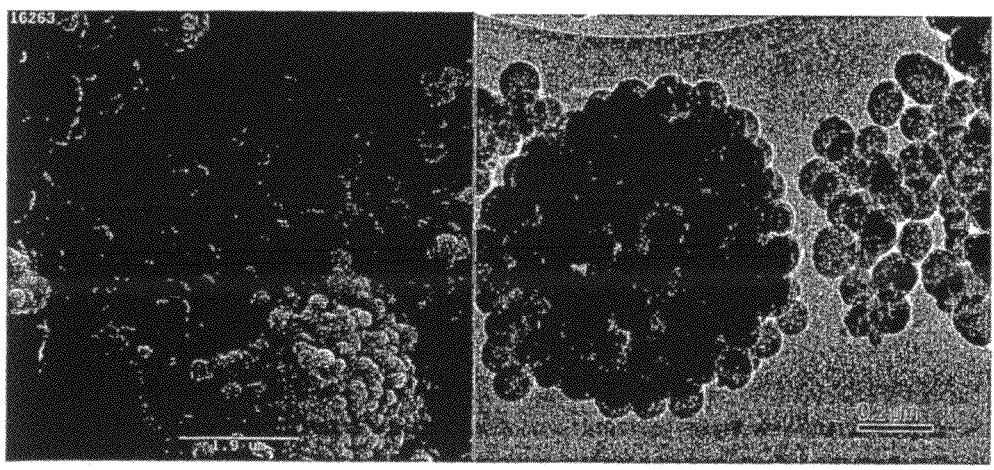

Effect of Colloid Type:

The typical synthesis procedure was followed using addition of 1.62 mL of various colloidal silicas, with results as listed in the table below. The corresponding SEM/TEM images are shown in FIG. 11. Ludox SM-30, Ludox HS-40, Bindzil 30/360, Bindzil 15/500, Snowtex 40 and Snowtex UP formed microparticles, while Ludox TM-50, Snowtex 50, and Snowtex 20L produce agglomerated products (about 500 nm spherical particles). Snowtex ZL formed an aggregated product (initial colloid about 70-100 nm). Snowtex N did not gel, which may suggest that there are some surface active agents already incorporated in the colloid suspension by supplier.

| Sample number | 1 | 2 | 3 | 4 | 5 | 6 |
| --- | --- | --- | --- | --- | --- | --- |
| Colloid volume (mL) | 1.08 | 1.62 | 2.16 | 3.24 | 4.32 | 5.40 |
| SiO$_2$ (g) in suspension | 0.395 | 0.593 | 0.791 | 1.186 | 1.581 | 1.976 |
| H$_2$O (g) in suspension | 0.922 | 1.384 | 1.845 | 2.767 | 3.689 | 4.612 |
| H$_2$O (mmol) | 51.24 | 76.86 | 102.48 | 153.72 | 204.96 | 256.20 |
| [H$_2$O]/[NP-5] mol ratio | 5.12 | 7.69 | 10.25 | 15.37 | 20.50 | 25.62 |
| Product (g) | 0.483 | 0.693 | 0.956 | 1.466 | 1.800 | 2.298 |
| Material adsorbed (g) | 0.088 | 0.100 | 0.165 | 0.280 | 0.219 | 0.322 |
| Residue/SiO$_2$ (wt. %) | 22.3 | 16.9 | 20.9 | 23.6 | 13.9 | 16.3 |

Density (Ludox SM-30) = 1.22 g/cm$^3$
SiO$_2$ in Ludox SM-30 = 30 wt. %
10 mmol NP-5 was used to prepare microemulsion.

Colloid Properties and Corresponding Products for Different Colloidal Silicas.

|  | SiO$_2$ (wt. %) | Size (nm) | pH | Product |
|---|---|---|---|---|
| Ludox SM-30 | 30 | 7 | 9.9 | Microparticles |
| Ludox HS-40 | 40 | 12 | 9.7 | Microparticles |
| Ludox TM-50 | 50 | 22 | 8.9 | Aggregated spheres |
| Bindzil 30/360 | 30 | 9 | 10 | Microparticles |
| Bindzil 15/500 | 15 | 6 | 10 | Microparticles |
| Snowtex 40 | 40 | 10-20 | 9.0-10.5 | Microparticles |
| Snowtex 50 | 50 | 20-30 | 8.5-9.5 | Aggregated spheres |
| Snowtex N | 20 | 10-20 | 9-10 | Not gelling |
| Snowtex UP | 20 | 9-15/40-300 | 9-10.5 | Microparticles |
| Snowtex ZL | 40 | 70-100 | 9-10 | Agglomerated |
| Snowtex 20L | 20 | 40-50 | 9.5-11 | Aggregated spheres |
| Sodium silicate | 27 | Na$_2$Si$_3$O$_7$ | ~14 wt. % NaOH | Fast gelation |

Figure 12:
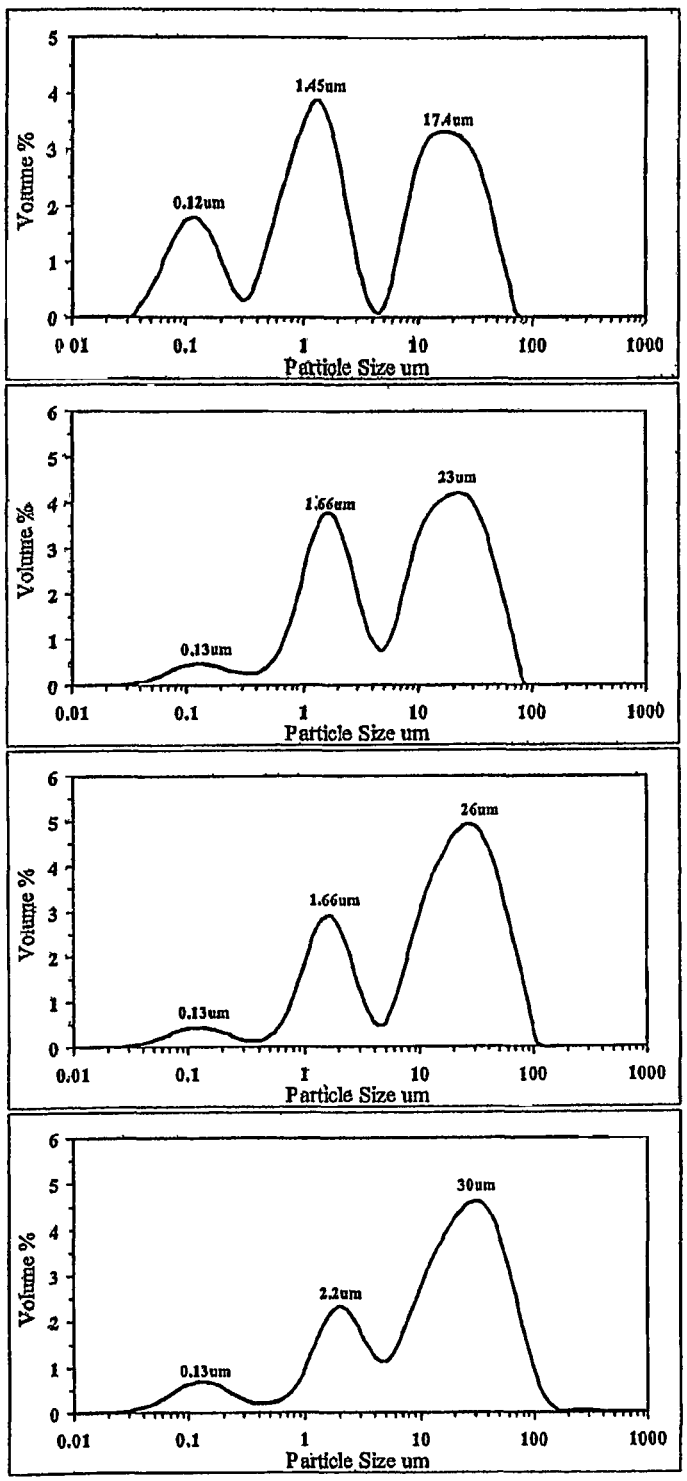
FIG. 12 shows graphs depicting particle size distribution of particles formed using the process outlined in FIG. 1, as determined by light scattering.

Particle Size Distribution:

The size distribution of the particles produced may be determined by light scattering (e.g. using a Malvern Mastersizer 2000). Size distributions of silica particles produced using the typical synthesis, with the amount of Ludox SM-30 varying from 1.62 mL to 5.40 mL, are shown in FIG. 12. Generally, three discrete peaks appear from 30 nm to 100 µm. The smallest peak, centred at around 130 nm, appears to be independent of colloid concentration. The middle peak increased slightly from 1.45 µm to 2.2 µm as the Ludox concentration increases. The largest peak (1-100 µm) changed from 17.4 µm for 1.62 mL Ludox, to 23 µm (3.24 mL Ludox), 26 µm (4.82 mL Ludox) and 30 µm for 5.40 mL Ludox. An increase in the volume of colloidal suspension used led to an increase in particle size due to an increase in the water to surfactant ratio and thus of the size of the water droplet.

Figure 13:
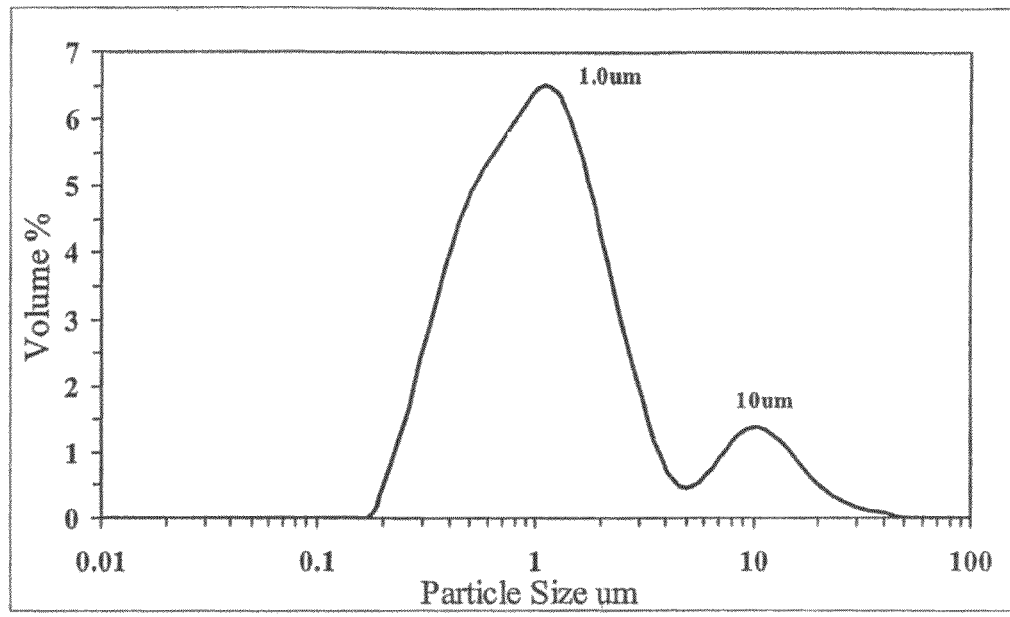
FIG. 13 is a graph showing particle size distribution for particles produced by the process of the invention wherein an ultrasonic probe was used in making the particles.

In order to reduce the particle size distribution, more energy may be supplied to the system. This may be achieved using more rapid stirring, or shear-mixing, for example. FIG. 13 shows the particle size distribution which was obtained for particles prepared from Bindzil 30/360 using the method described in Example 3 (with no added enzyme), but instead of using stirring to mix the emulsion, an ultrasonic probe was used to increase the agitation of the system in the first hour of operation. The ultrasonic probe was operated on a 1 second pulse per 2 seconds (50% duty cycle). After one hour, the probe was removed from the emulsion, and stirring commenced for the remaining five hours of the synthesis. The particle size was clearly reduced from the typical size range (shown in FIG. 12), and is centred around 1 micron. There was a small component of large particles present. Due to the increased energy input, the temperature of the system did significantly increase to 60° C. after one hour of ultrasonics. This is clearly not appropriate for most proteins, but may be modified by adjustment of the ultrasonic probe duty cycle or by using an ice bath to reduce the temperature.

Encapsulation of Proteins

Figure 14:
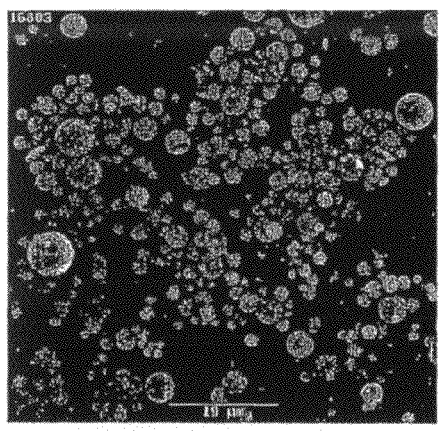
FIG. 14 is a scanning electron micrograph of silica particles formed by reduction of the pH to 6.0 inside the emulsion.

Certain proteins may be encapsulated at high pH, depending on their pKa. Alkaline phosphatase has a pKa of 9.5 and a procedure for encapsulating this enzyme while retaining full enzymatic activity is given in Example 1 (see below). However, the majority of enzymes have optimum activity around neutral pH. It is possible to reduce the pH of the colloidal precursor before addition to the surfactant solution as described above, and a method for encapsulating alpha-chymotrypsin, subtilisin and alkaline phosphatase in colloid reduced to pH=7.5 is given in Example 2 (see below). However, the inventors have found that doped particles may be formed by addition of an aqueous precursor to a surfactant solution to form an emulsion, followed by addition of acid to reduce the pH to a suitable value, and subsequent addition of the biological entity. Although particles are formed quickly after addition at pH 10, the inventors hypothesise that the particles are not fully dense immediately after formation, and consequently that proteins or other biological entities may be able to infuse into the particles as they age in the water droplets of the emulsion. Typically, the pH in the water droplet has been reduced to 6.0 before addition of the protein. Using this method, enzymes of varying sizes, alpha-chymotrypsin (~25 kDa), subtilisin (~27 kDa), alkaline phosphatase (~160 kDa), and urease (~480 kDa), have been encapsulated. The surfactant used for most of this encapsulation (ie reduction of pH to 6.0 inside the emulsion) has been Span20, although AOT has also been used, with similar particles being formed in both cases. A typical SEM image of particles formed using this method with Span 20 is shown in FIG. 14.

A mechanism for adjusting the release rates of alpha-chymotrypsin, alkaline phosphatase and urease from such particles was investigated in Example 3 (see below), involving the use of different-sized colloidal precursors to influence the average pore size of the particles. Example 4 (see below) also describes the use of different sized colloidal solutions to control the amount of subtilisin released. The distribution of ferritin in a microparticle has been examined in Example 5 (see below), using cross-sectional TEM to map the location of the ferritin molecules. The effect of the encapsulation process on the activity of subtilisin has been examined in Example 6 (see below). A study of the storage stability of subtilisin and alkaline phosphatase has been described in Example 7 (see below). The encapsulation of enzymes in alternative ceramic (i.e. other than silica) matrices has been described in Example 8 (see below).

Example 1

Encapsulation of Alkaline Phosphatase at pH=9.7

0.5 mL of 0.5 mol/L nitric acid was added to 10 mL of Bindzil 30/360 to give a pH of 9.7. Alkaline phosphatase (8 mg dissolved in 400 µl of buffer at pH=9.5) was mixed with 2.5 mL of the above colloidal silica suspension, then added with stirring to a Span 20 solution (02 mol/L) in 50 mL kerosene. After stirring for about 10 minutes, particles were separated by centrifugation at 2000 rpm for 3 minutes. The resulting particles were washed once with kerosene, followed by three washes with hexane (using the centrifuge to separate the supernatant from the solid after each wash) and then dried at room temperature under flowing nitrogen and then stored in a freezer.

Alkaline phosphatase was encapsulated with a loading of approximately 0.6% (by weight) protein (see method below for protein content determination). The enzyme activity was measured immediately after drying and was found to actually be higher than that of free enzyme in solution. This indicates that the encapsulation process as described did not denature the protein to any significant degree.

Figure 15:
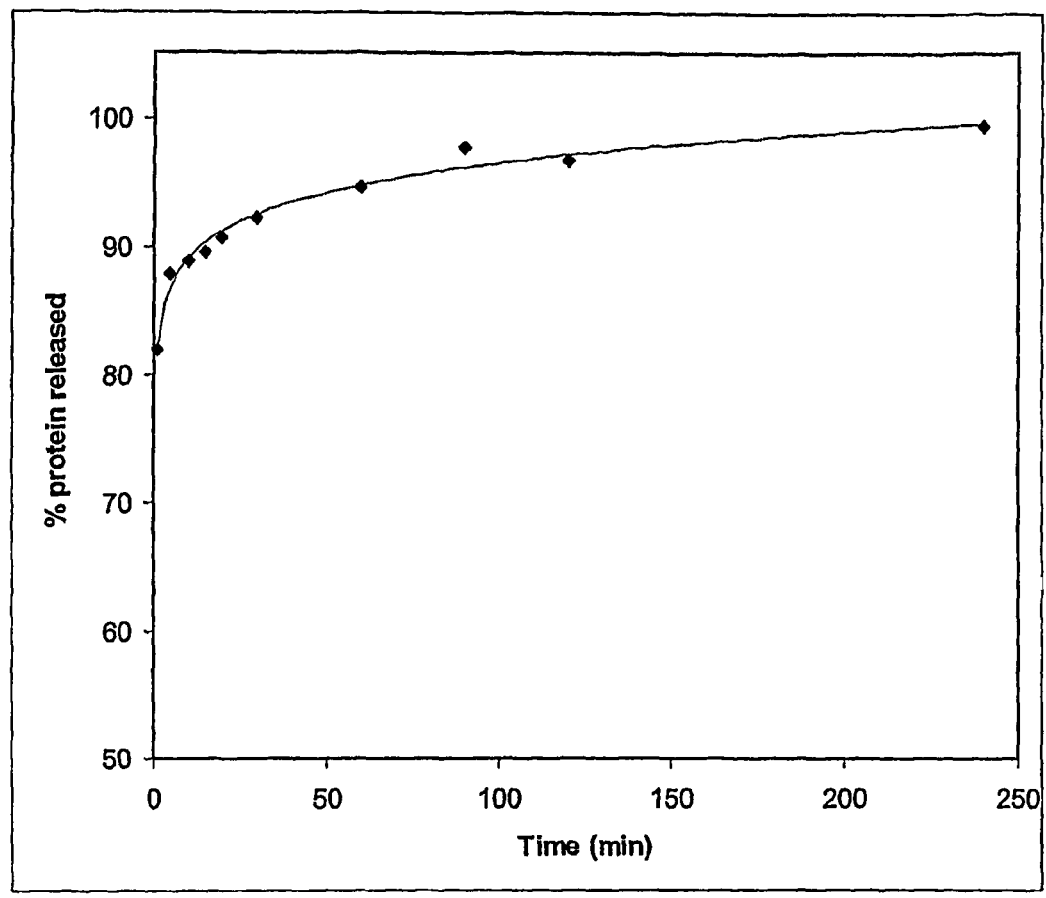
FIG. 15 is a graph showing the release of alkaline phosphatase from particles formed at pH=9.7.

FIG. 15 shows the release rate of alkaline phosphatase encapsulated at pH=9.7 as described above.

Protein Content Determination

Protein content of microparticles, and quantification of protein released from microparticles was determined using the Bicinchoninic Acid (BCA) Assay as follows:

Standard Assay:
Reagent A: Sodium Bicinchoninate (0.1 g), $Na_2CO_3.2H_2O$ (2 g), sodium tartrate (dihydrate) (0.16 g), NaOH (0.4 g), $NaHCO_3$ (0.95 g), made up to 100 mL. If necessary adjust pH to 11.25 using NaOH.
Reagent B: $CuSO_4.5H_2O$ (0.4 g), made up to 10 mL
Standard Working Reagent (SWR)=100 volumes of reagent A+2 volumes of reagent B. Method:
Quantification of Protein in Microparticles:
Protein containing microparticles (20 mg) were suspended in phosphate buffered saline (PBS solution) (400 µL), and the suspension ultrasonicated for 5 minutes. A sample of the suspension (50 µL) is taken in triplicate, and combined with SWR (1 mL) and incubated at 60° C. for 60 minutes. The sample is centrifuged at 3000 rpm for 5 seconds, and the absorbance of the solution is measured at 562 nm, and compared to that of a series of standards at 0.1, 0.2, 0.4, 0.6, 0.8 and 1.0 mg/mL.
Quantification of Protein Released from Microparticles:
Protein containing microparticles (100 mg) were suspended in PBS solution (2 mL), and agitated. At time points required the suspension was centrifuged, and a sample (50 µL) removed. The samples from each time point were combined with SWR (1 mL) and incubated at 60° C. for 60 minutes. The sample absorbance was measured at 562 nm, and compared to that of a series of standards at 0.1, 0.2, 0.4, 0.6, 0.8 and 1.0 mg/mL.

Example 2

Encapsulation of alpha-chymotrypsin, Subtilisin and Alkaline Phosphatase at pH=7.5 (Reduced to pH=6 Inside Emulsion)

alpha-chymotrypsin, subtilisin and alkaline phosphatase were encapsulated into particles formed from Bindzil 30/360 using the following method: 4.6 g of Span20 was dissolved in 30 ml of kerosene with stirring. 1.25 ml of Bindzil 30/360 was mixed with 158 ml of 1M HCl to reduce the pH from 10 to 7.5. 4 mg of protein was dissolved in 200 µl of water, and then dispersed with stirring into the Bindzil solution. The precursor solution containing the protein was then added to the emulsion. After stirring for several minutes, 72 µl of 1 M HCl was added to further reduce the pH to 6.0. Finally, 175 µl of salt solution 2 (see Example 6 for composition) was added to the emulsion. After 6 hours stirring, the emulsions were centrifuged and the solids washed once with kerosene, then twice with hexane, then dried overnight.

Figure 16:
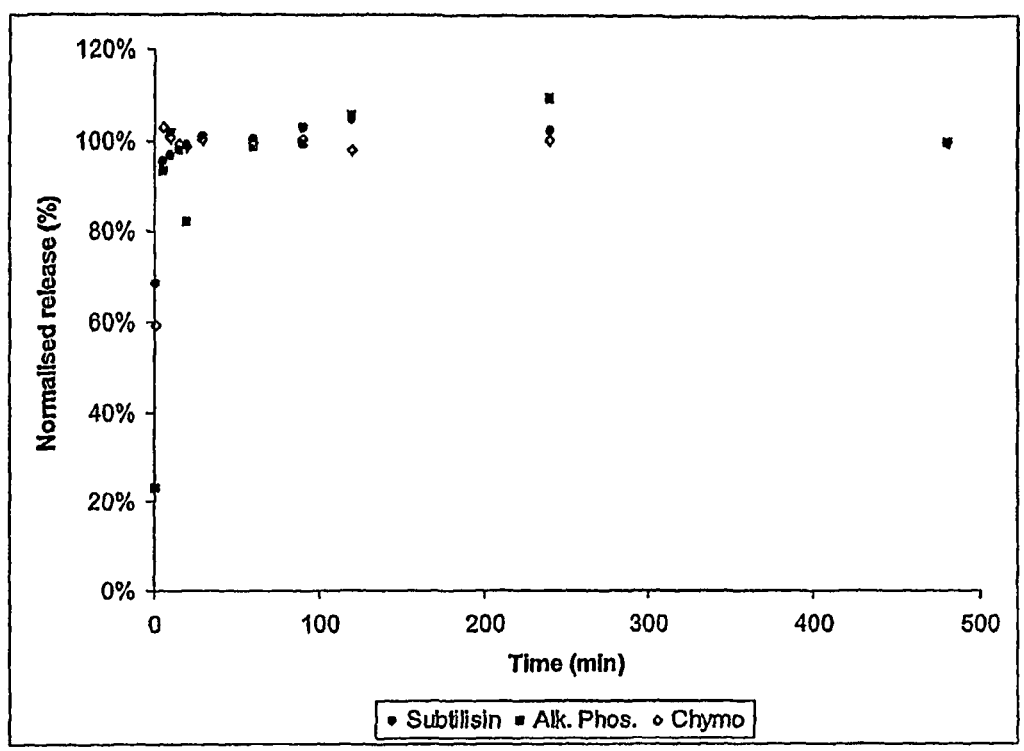
FIG. 16 is a graph showing the normalized release of alpha-chymotrypsin, subtilisin and alkaline phosphatase over a period of 8 hours.

100 mg of the sample was dispersed in 2 ml of PBS in the case of subtilisin and alpha-chymotrypsin, and in ethanolamine buffer (pH=9.5) in the case of alkaline phosphatase. At the specified time points, the sample was spun down at 10,000 rpm for 10 seconds, and 50 µl removed. The protein content was determined as described in Example 1, and the release curves calculated. FIG. 16 shows the release of alpha-chymotrypsin, subtilisin and alkaline phosphatase over a period of 8 hours. The rapid release (almost fully released after ten minutes) appears to be due to the large pore size (8.7 nm) formed using this method (see discussion in Example 4 below).

Example 3

Figure 17:
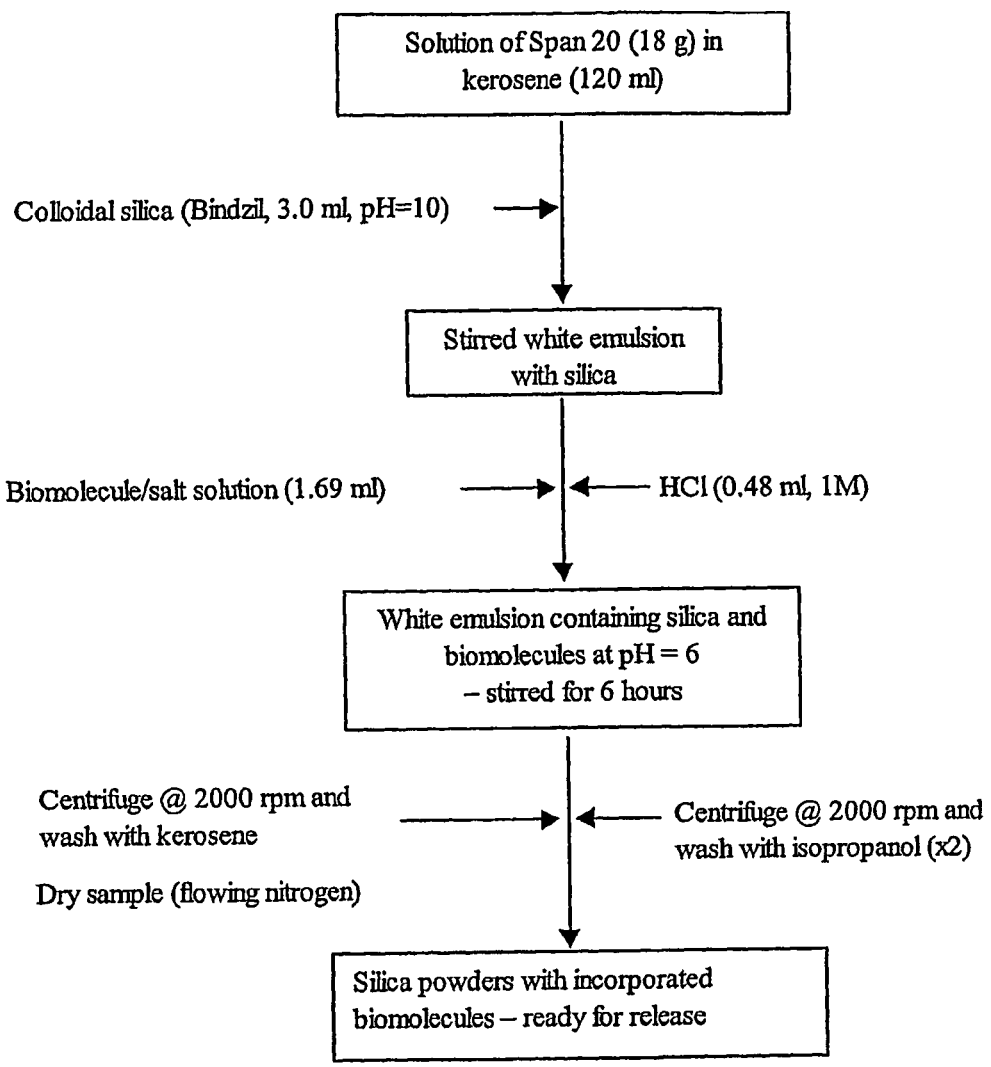
FIG. 17 is a flowchart showing particle synthesis using a Span20/kerosene emulsion, with encapsulation of the protein at pH=6.0.

Encapsulation of alpha-chymotrypsin, Alkaline Phosphatase and Urease at pH=6.0 alpha-chymotrypsin, alkaline phosphatase and urease were encapsulated into particles formed from Bindzil 30/360 by using the following method:

A flow diagram describing the particle synthesis is shown in FIG. 17. Release rates were measured as described in Example 1. Combining a solution of a Span 20 (18 g) in kerosene (120 mL) with Bindzil 30/360 colloidal silica (3.0 mL; pH 10), stirring at about 500 rpm, generated a white emulsion. In this case, the biomolecule (protein) was dissolved in the salt solution before addition to the emulsion. Addition of a solution of a biomolecule and salt (1.69 ml), and adjustment of the pH with hydrochloric acid (0.48 mL, 1M), provided a white emulsion having pH about 6. After stirring for six hours, the particles were separated by centrifugation at 2000 rpm and washed with further kerosene and then twice with isopropanol, and then dried in a stream of nitrogen. The resulting powder had the biomolecule encapsulated.

Figure 18:
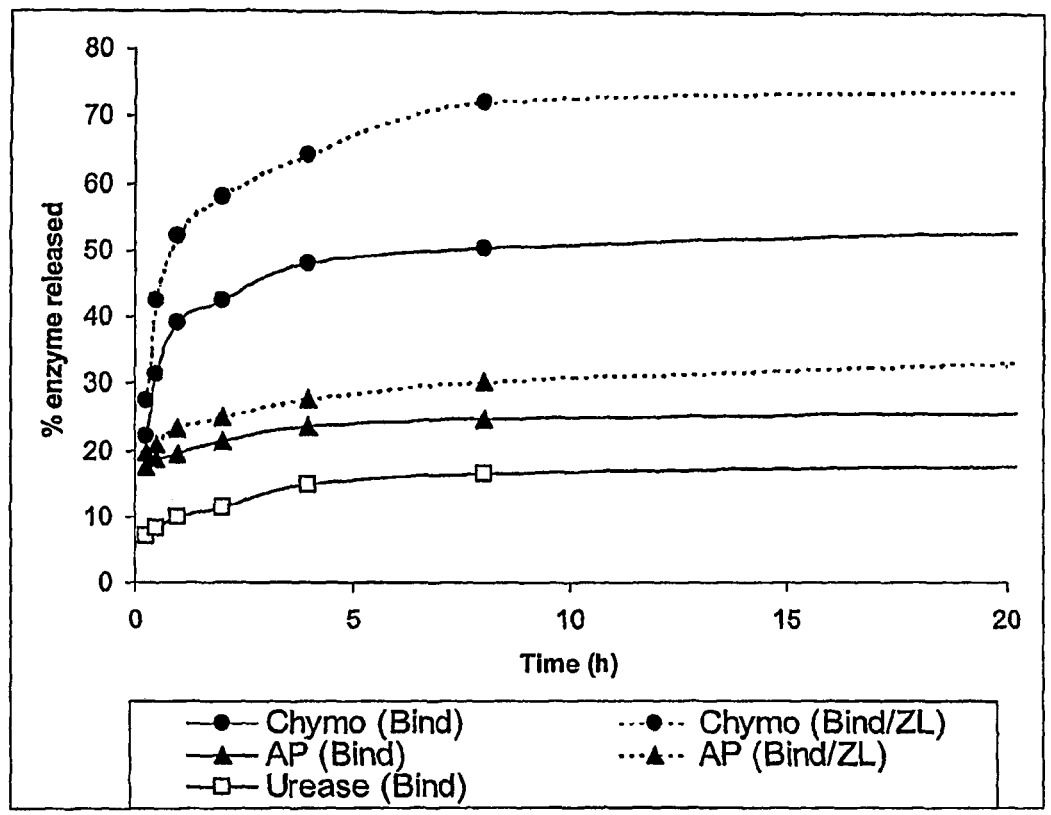
FIG. 18 is a graph showing release of chymotrypsin, alkaline phosphatase and urease from silica particles according to the invention, with average pore sizes 5.5 and 6.7 nm (note that the release of urease from particles with 6.7 nm pores is not represented here).
Figure 19:
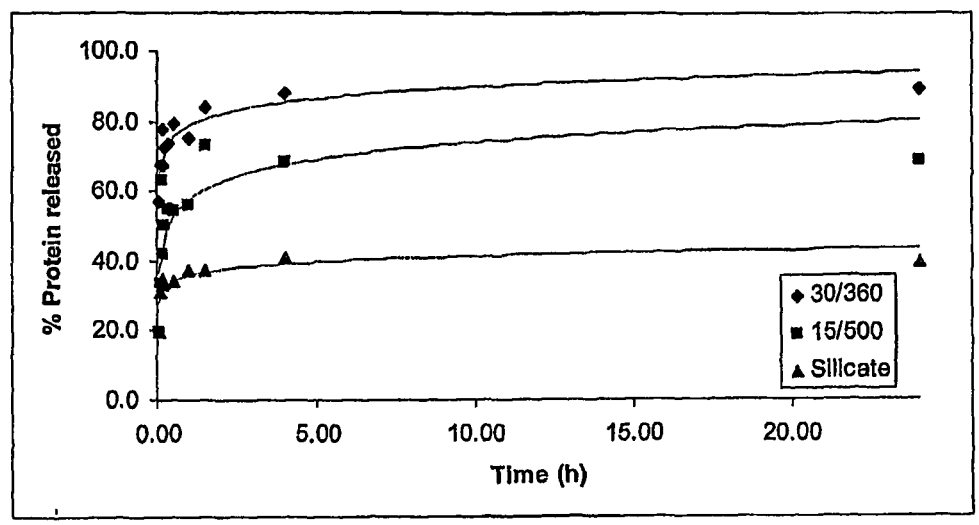
FIG. 19 is a graph showing the release of subtilisin from silica produced using (♦) Bindzil 30/360, (■) Bindzil 15/500 and (▲) silicate.
Figure 20:
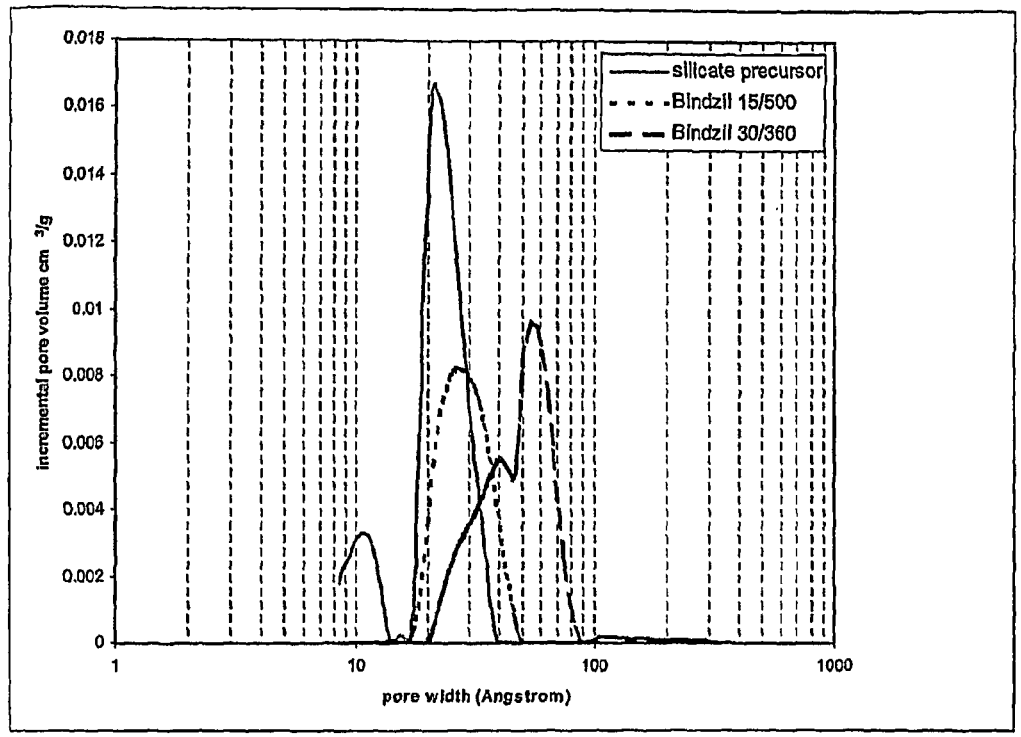
FIG. 20 is a graph showing the pore size distribution for the particles made from silicate, Bindzil 15/500 (6 nm) and Bindzil 30/360 (9 nm) precursors, as outlined in Example 4.

To increase the size of the pores in the silica, a mixture of Bindzil 30/360 and Snowtex ZL was employed, Snowtex ZL consists of 70-100 nm colloidal particles, considerably larger than the 9 ml colloidal particles in Bindzil 30/360. alpha-chymotrypsin, alkaline phosphatase and urease were encapsulated into particles formed from a mixture of Bindzil 30/360 and Snowtex ZL by the following method:

18 g of Span20 was dissolved in 120 mL kerosene with stirring. 1.5 mL of Bindzil 30/360 was mixed with 1.5 mL of Snowtex-ZL, and added to the emulsion with stirring. 30 mg of protein was dissolved in a solution of 0.31 mL 1M HCl, and 0.422 ml of concentrated salt solution (concentrated by a factor of 4), and added to the emulsion. After six hours, the solids were removed by centrifugation, washed with kerosene and iso-propanol, and dried overnight. Release rates were measured as described in Example 1, and are shown in FIG. 18. The release of urease from the Bindzil 30/360/Snowtex ZL mixture is not reproduced here because of cloudiness of the absorption solution which interfered with the protein quantification. The increased release for alpha-chymotrypsin and alkaline phosphatase from the Bindzil 30/360/Snowtex ZL particles (which have an average DFT pore size of 6.7 nm as opposed to 6.5 nm for the Bindzil 30/360 particles) indicates that the larger pores have a significant effect on the rate of enzyme released.

Preparation of particles using both Bindzil 30/360 and Bindzil 16/600 was conducted using the method outlined in Example 4, but without the addition of salt solution. The products consisted largely of spherical particles, with a small component of non-spherical material. Particle size and porosity measurements indicated that the size and internal microstructure of the particles were virtually identical to those made using salt solution. Comparison of particles made with and without salt suggested that there are two main advantages in adding salt. The first is to reduce the proportion of non-spherical material. The second is that the addition of salt results in a higher yield of encapsulated protein. In the case of alkaline phosphatase as the biological entity omitting the step of adding salt solution resulted in a 40% reduction in the protein loading (from 1.5 wt % to 1.1 wt % for the same initial amounts of aqueous colloid and enzyme solution). Salt solution may be more important when gelling colloidal solutions such as Snowtex-40, which comprises larger primary particles (10-20 nm). However, particularly in situations where the presence of salt might to cause problems, it may be omitted.

Salt solution composition in 200 mL (50 mL for concentrated salt solution):
0.1 g $KH_2PO_4$
0.2 g $NH_4Cl$
0.21 g $Na_2SO_4$
0.223 g $CaCl_2$ 1.2 g sodium lactate
0.06 g sodium citrate
4.1 g NaCl
1.973 g $MgCl_2.6H_2O$

Example 4

Encapsulation of Subtilisin at pH=6.0. Determination of Pore Size Effect

Release rate measurements of subtilisin from particles made using Bindzil 30/360 indicated that most of the protein release occurred within 1 hour of immersion of the powder: in 0.02M PBS solution. One possible method for reducing the pore size is to use a smaller colloid as a silica precursor. Bindzil 30/360 comprises 9 nm silica particles, 30 wt % in solution. Bindzil 15/500 comprises of 6 nm silica particles, 15 wt % in solution. There is a small difference in the amount of acid required to reduce the pH to 6.0 (0.115 mL 1M HCl per mL of Bindzil 15/500, compared to 0.183 mL per mL of Bindzil 30/360). The porosity of this product is discussed below.

Alternatively sodium silicate solution may be used as a precursor instead of colloidal silica. Spherical particles were produced by first preparing an emulsion containing 9 g Span20, 60 mL kerosene, and 1 mL 4M HCl. Addition of 1 ml of sodium silicate solution (27%) resulted in the formation of spherical particles in the size range about 1-100 micron. However, this preparation process is not suitable for encapsulation of protein due to the extreme pH encountered. Reduction of the pH of sodium silicate solution results in immediate precipitation. In order to reduce the pH, it is necessary to dilute the sodium silicate solution, and reduce the sodium content using an ion exchange resin.

Example Preparation of Deionised Silicate Solution:

33 mL of sodium silicate solution (27%) was diluted to 99 mL with distilled water. 34.6 g of Duolite cation exchange resin (H+ form) was added with stirring to reduce the pH to 11.45. The duolite resin was removed by filtration, and 31.16 g of fresh resin added to reduce the pH to 9.8.

20 g Span 20 was dissolved with stirring in 135 mL kerosene. 6 ml of the silicate solution at pH=9.8 was added and stirred for several minutes to disperse in the surfactant mixture. 1 mL of 1M HCl was added and the emulsion left to stir. After 6 hours, the solid was removed by contrifugation, and washed using kerosene, and ethanol (×2). The average pore size of a freeze-dried sample is compared with those of other colloidal precursors in the table below.

Encapsulation of Subtilisin:

4.5 g of Span 20 was dissolved in 30 mL kerosene, and stirred to dissolve. 1.25 mL of either Bindzil 15/500 or Bindzil 30/360 was added to the mixture to form an emulsion. The emulsion was acidified with 1M HCl (144 μL for Bindzil 15/500, and 198 μL for Bindzil 30/360), followed by addition of 10 mg subtilisin in 200 μl of water and 98 μl of salt solution 4. The reaction was stirred for 5 hours. Particles were isolated by centrifugation, washed with kerosene and twice with cyclohexane and dried under a stream of nitrogen to give a pale white powder.

Subtilisin was encapsulated in silicate particles by the following method: 18 g Span 20 was dissolved in 120 mL kerosene with stirring. A solution of 8 mg of subtilisin in 200 μL of water was added to the surfactant solution, followed by addition of 4 ml of the deionised silicate, prepared as described above. 0.67 mL of 1M HCl was added to reduce the pH to 7.2. The solution was stirred for 6 hours, then the solid removed by centrifugation. The particles were washed once with kerosene, then twice with hexane (centrifuging to remove the supernatant after each wash) and dried overnight.

FIG. 19 shows a graph of the release curves for subtilisin from Bindzil, 30/360, Bindzil 15/500 and silicate microparticles, synthesized as outlined above. The release curves are of similar form, however, the total percent released varies according to the pore size of the particles. FIG. 20 shows the pore size distribution for the three different samples used in this Example. The smaller the pore size, the lower the overall percent of protein that is released from the particles. The average pore size of the typical precursors used are tabulated below.

Particle Porosity

Nitrogen adsorption data has been modelled using Density Functional Theory (DFT), which describes the behaviour of gas adsorption on a molecular level, and is appropriate for modelling a wide range of pore sizes. Cylindrically shaped pores were assumed. Average pore sizes are tabulated for a variety of silica precursors, are tabulated below. The average pore size appears to be determined by the size of the initial colloidal particle and the pH of gelation. Unless otherwise specified, the surfactant used in the preparation was Span20.

| Silica precursor | Primary particle size (nm) | Average DFT pore size (nm) |
|---|---|---|
| Silicate soln (9%) | — | 2.1 |
| Bindzil 15/500 - reduced to pH = 6.0 in emulsion | 6 | 2.7 |
| Bindzil 30/360 - reduced to pH = 6.0 in emulsion | 9 | 5.5 |
| Bindzil 30/360 - reduced to pH = 6.0 in emulsion. Surfactant = AOT. | 9 | 5.8 |
| Bindzil 30/360 - reduced to pH = 7.5 on bench, then to 6.0 in emulsion. | 9 | 8.7 |
| Bindzil 30/360 - pH = 10 in emulsion | 9 | 5.9 |
| Ludox SM-30 - reduced to pH = 6.0 in emulsion | 7 | 6.2 |
| Snowtex-40 - reduced to pH = 6.0 in emulsion | (10-20) | 7.1 |
| Bindzil30/360/(60%) + Snowtex ST-50 (40%) - reduced to pH = 6.0 in emulsion | 9 + (20-30) | 6.2 |
| Bindzil30/360/(50%) + Snowtex -ZL (50%) - reduced to pH = 6.0 in emulsion | 9 + (70-100) | 6.7 |
| Snowtex ZL * - reduced to pH = 6.0 in emulsion | 70-100 | 45 |

* colloid gelled on addition of polyethylene imine solution

Example 5

Distribution of Ferritin in Microparticles

The inventors considered the possibility that a protein may tend to remain in the interfacial region of an emulsion rather than in the interior of a water droplet, due to the presence of hydrophobic regions in the protein molecule. It was considered that this orientational effect may have resulted in the protein being encapsulated in the outer shell of the microparticle forming inside the emulsion droplet. In order to investigate the distribution of encapsulated protein throughout the body of the particle, silica particles were doped with ferritin, which contains an iron core and thus should be easily detectable by Transmission Electron Microscopy (TEM).

Preparation details: Span 20 (1.6 g) was dissolved in kerosene (12 mL). Ferritin solution (~100 mg/mL, 126 µL) was mixed with Bindzil 30/360 (300 µL). This mixture was then added to the surfactant solution dropwise, with stirring at 500 rpm. HCl (1 M, 480 µL) and a concentrated salt solution were mixed. 91 µL of this solution was added to the emulsion. The emulsion was left stirring for 2.5 hours, at which time solid material appeared on the bottom of the reaction vessel. The mixture was centrifuged (2000 rpm, 3 minutes) and the solid was washed once with kerosene and twice with isopropanol. The solid material was dried under flowing nitrogen. The final powder was an 'ochre' colour, indicating the successful encapsulation of ferritin within the particles.

Mapping of Protein Distribution in Particle

Figure 21:
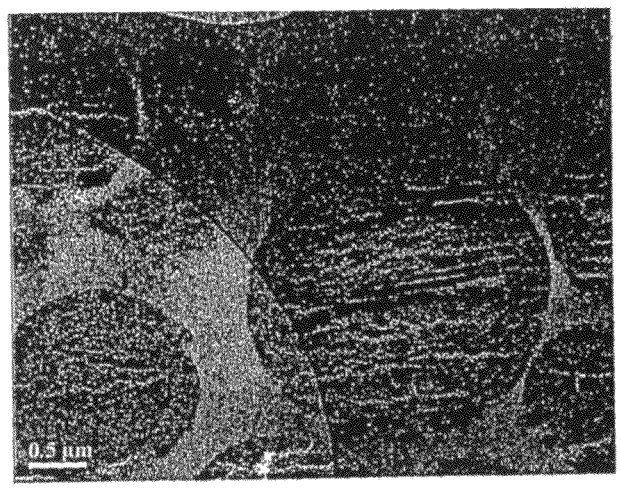
FIG. 21 is a scanning electron micrograph of silica particles according to the invention.

Particles were imbedded in resin and 80 nm thin sections were cut using a 30° Diatome diamond knife on a Leica Ultracut UCT ultramicrotome and applied to holey carbon coated copper grids. FIG. 21 shows a typical scan of the particles, with some knife damage evident on the central particle. The Fe distribution over part of the cross-section of a silica particle was mapped by Scanning TEM (STEM) energy dispersive x-ray spectroscopy (EDX) spectrum imaging. This technique involves collection of a full EDX spectrum at each pixel in a STEM image and subsequently processing each spectrum to remove background x-rays. Maps of elemental distribution are generated by plotting x-ray intensity in regions of the spectrum corresponding to each element of interest. The Fe distribution maps indicated that ferritin was uniformly distributed over the areas examined, suggesting that the protein does not orient within the droplet to remain near the surfactant/solvent interface.

Figure 22:
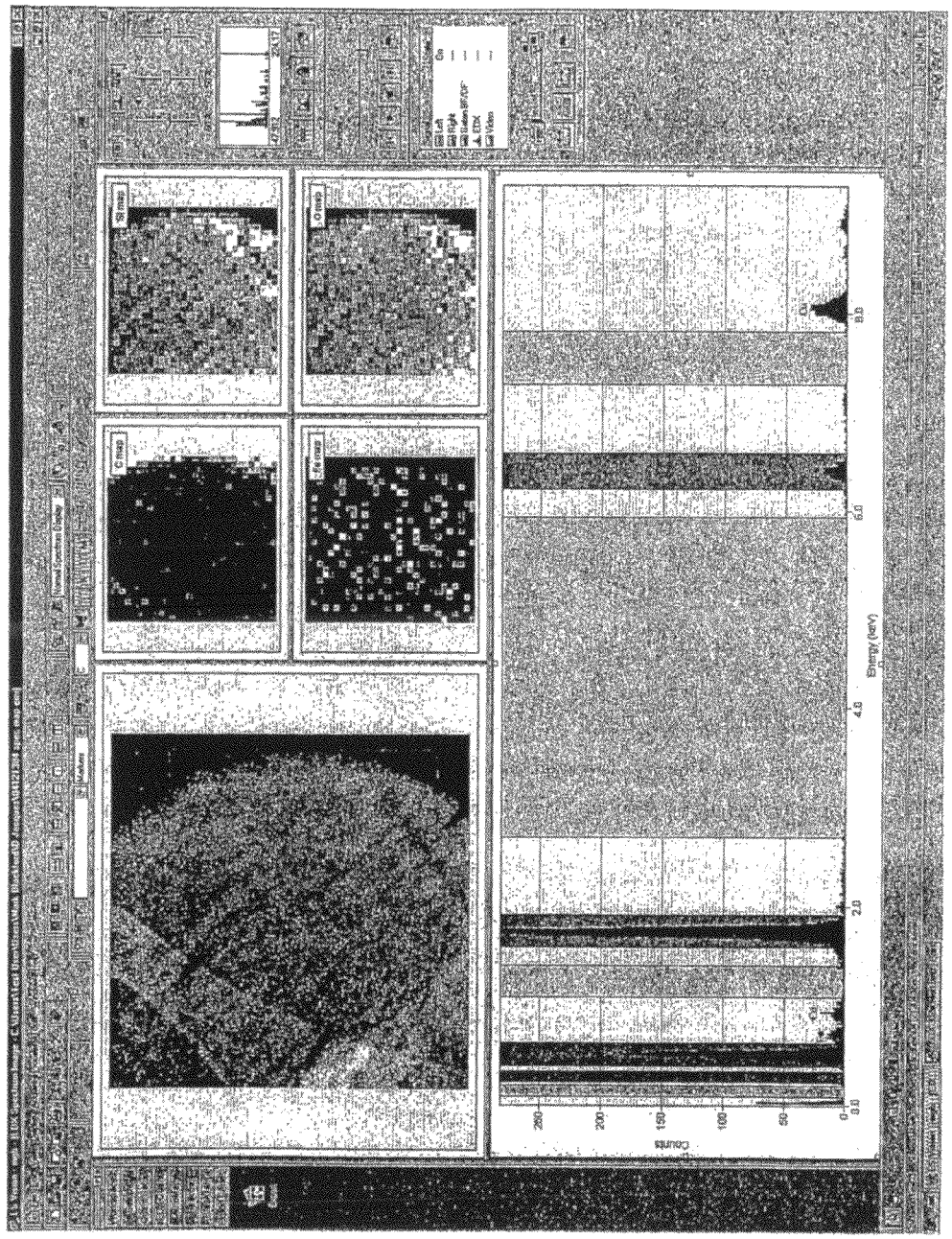
FIG. 22 is a STEM (scanning transmission electron micrograph) EDX spectrum image from a control specimen with no ferritin showing a distribution of C, Fe, Si and O in a slice of a particle.

FIG. 22 shows maps of C, Fe, Si and O distribution in a 50 pixel by 50 pixel area corresponding to the larger box on the STEM dark field imaging (DFI) image (upper left). The spectrum displayed in the lower panel clearly shows the Fe—K x-ray peak due to ferritin at the position of the small cross in the STEM DFI.

Figure 23:
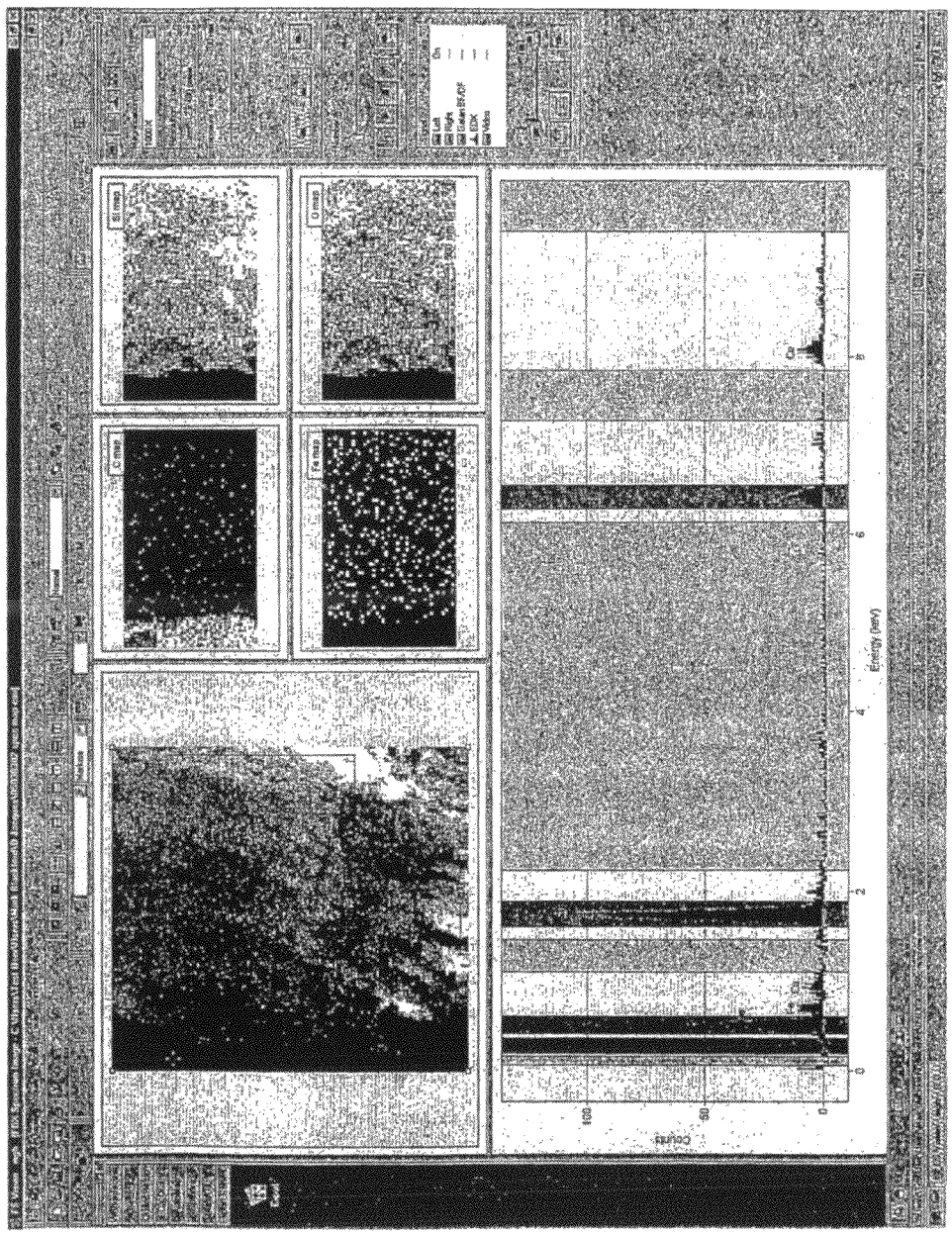
FIG. 23 is a STEM EDX spectrum image showing distribution of C, Fe, Si and O in a slice of a particle according to the invention.

FIG. 23 shows maps of C, Fe, Si and O distribution in a 75 pixel by 45 pixel area corresponding to the box on the STEM DFI image (upper left). The spectrum displayed in the lower panel clearly shows the Fe—K x-ray peak due to ferritin at the position of the small cross in the STEM DFI. The Fe distribution maps indicate ferritin is uniformly distributed throughout the analysed regions.

Figure 24:
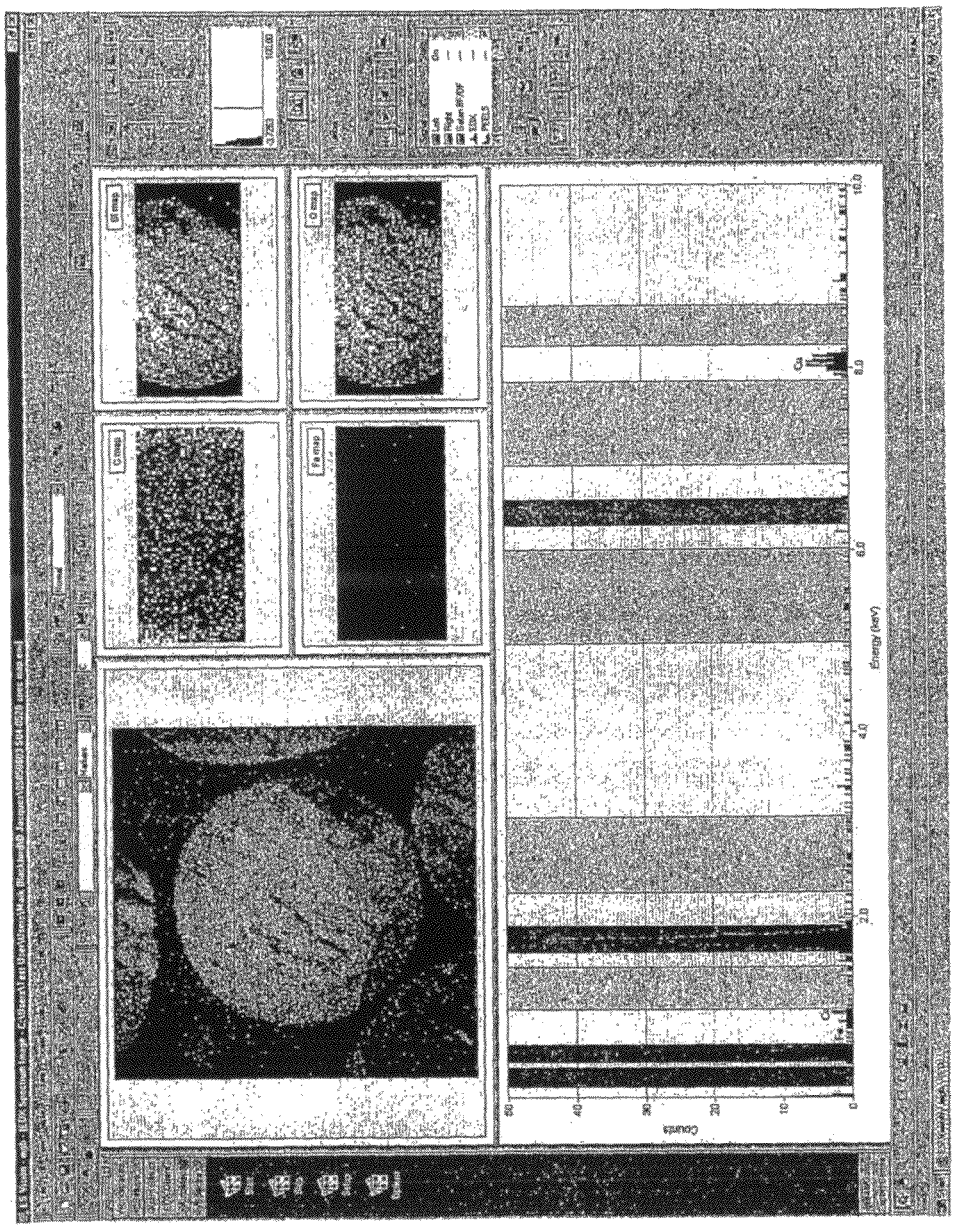
FIG. 24 is a STEM EDX spectrum image from a control specimen with no ferritin showing distribution of C, Fe, Si and O in a slice of particle.

FIG. 24 shows STEM EDX spectrum image from a control specimen with no encapsulated ferritin, showing distribution of C, Fe, Si and O in one slice of microsphere. As expected, no Fe was detected.

Example 6

Effect of Various Components used during Encapsulation on Activity of Alpha-chymotrypsin, Subtilisin and Alkaline Phosphatase Protein activity post-release is clearly an important issue for the use of the particles of the present invention. In an attempt to identify which components of the total assay could be responsible for any loss in activity, assays were performed using both alpha-chymotrypsin and subtilisin. The compositions of the various salt solutions used in these assays are given below. All solutions were made up to a volume of 50 ml with deionised water.

| Salt solution 1 | Salt solution 2 | Salt solution 4 |
|---|---|---|
| 0.1 g $KH_2PO_4$ | 0.1 g $KH_2PO_4$ | 0.1 g $KH_2PO_4$ |
| 6.46 g NaCl | 6.69 g NaCl | 7.02 g $CaCl_2$ |
| 0.233 g $CaCl_2$ | 1.3 g $CaCl_2$ | |
| 1.97 g $MgCl_2$ | | |

Figure 25:
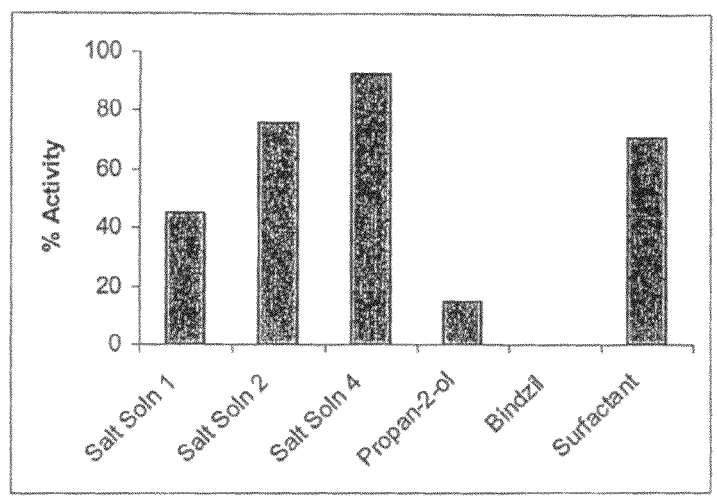
FIG. 25 is a graph showing the effect of components of the encapsulation process of the invention on activity of alpha-chymotrypsin.

FIG. 25 shows the effects of the various components of the encapsulation process on the activity of alpha-chymotrypsin. Addition to Bindzil resulted in complete denaturation of the enzyme. However, this was most likely due to the high pH (about 10) of the Bindzil. Aside from the Bindzil at pH 10, the most detrimental chemical appeared to be isopropanol, used for washing the particles. The salt solutions also seem to have a variable influence on the activity of the enzyme as well.

Figure 26:
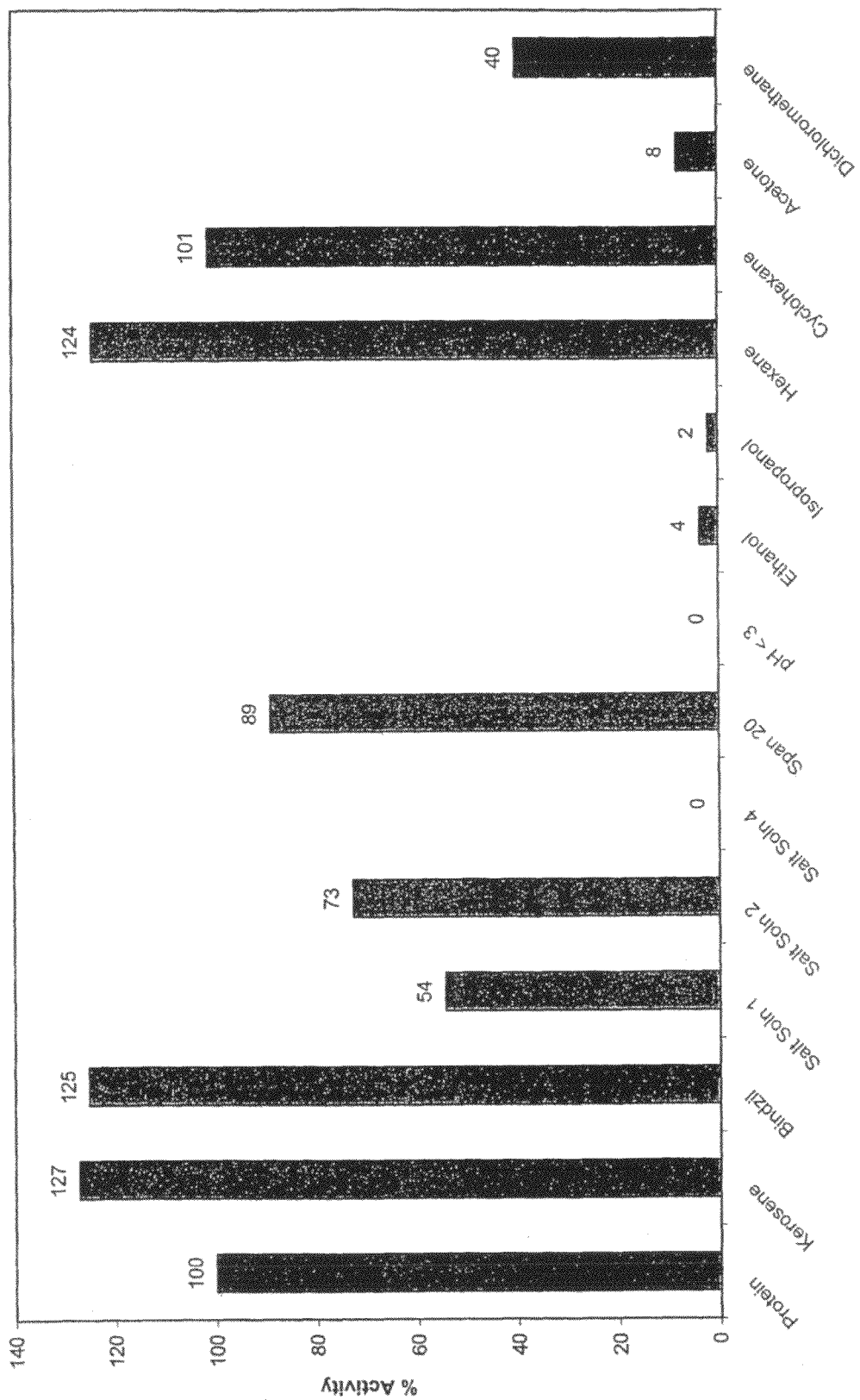
FIG. 26 is a graph showing the activity of subtilisin after treatment with various chemicals of the encapsulation process of the invention.

FIG. 26 shows the effects of the same components/chemicals, plus some additional washing solvents, on the activity of subtilisin. The two most detrimental chemicals for the activity of subtilisin appear to be acidic conditions (pH about 2), and salt solution 4. Acidic conditions (<pH 6) are known to be detrimental to subtilisin. Also salt solution 4, a concentrated solution of calcium salts proved to be detrimental. As seen above, two chemicals used occasionally for washing the particles, ethanol and isopropanol, both appear to be extremely detrimental for enzymatic activity. Hexane and cyclohexane were found to have no detrimental effect on the enzyme activity.

Figure 27:
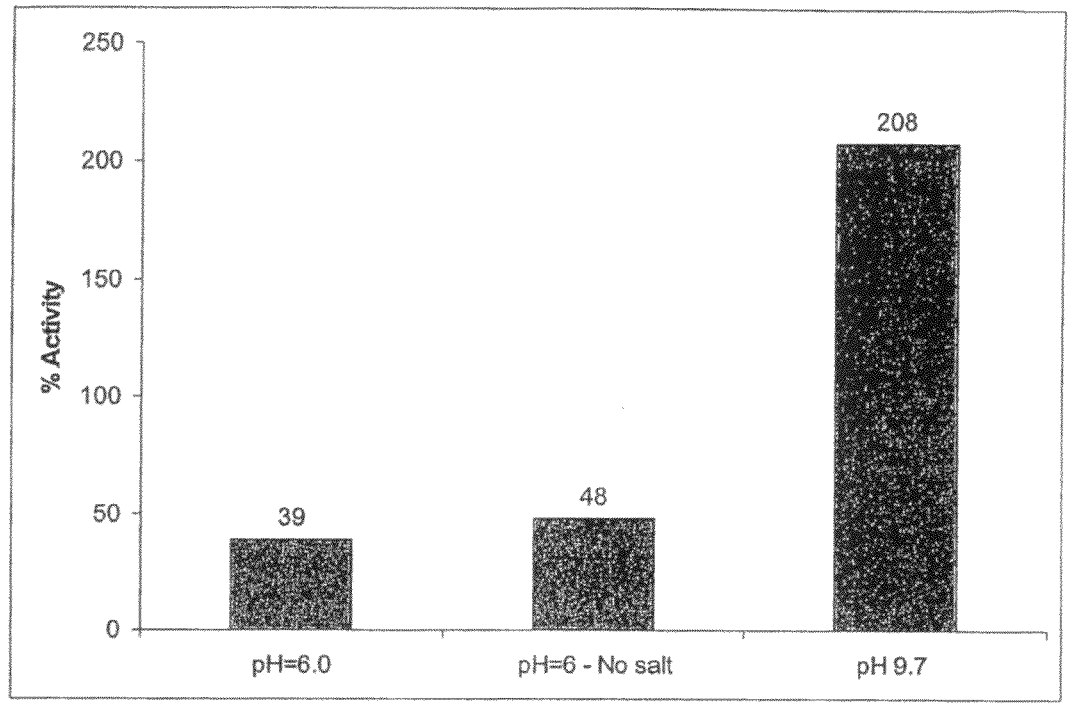
FIG. 27 is a graph showing the activity of alkaline phosphatase after encapsulation and at two weeks, using various encapsulation processes.

Alkaline phosphatase, with a pKa of 9.5, is significantly more stable than most enzymes at higher pH. This enzyme was used to test the effect on activity of encapsulating at pH about 10, and to relate this to the activity of enzymes submitted to the encapsulation procedure at pH 6. FIG. 27 shows the post-release activity of alkaline phosphatase following a) the encapsulation process at pH=6.0 as described in FIG. 17, and b) the same process, using no salt. This process leads to a similar loss of approximately 60% activity, with or without salt present. In contrast the process at pH 9.7 (as described in Example 1), being very close to the pKa of the enzyme, appears to increase its catalytic effect. This demonstrates that encapsulation at pH about 10 may be useful for systems capable of withstanding or even preferring a pH greater than about 9.

Figure 28:
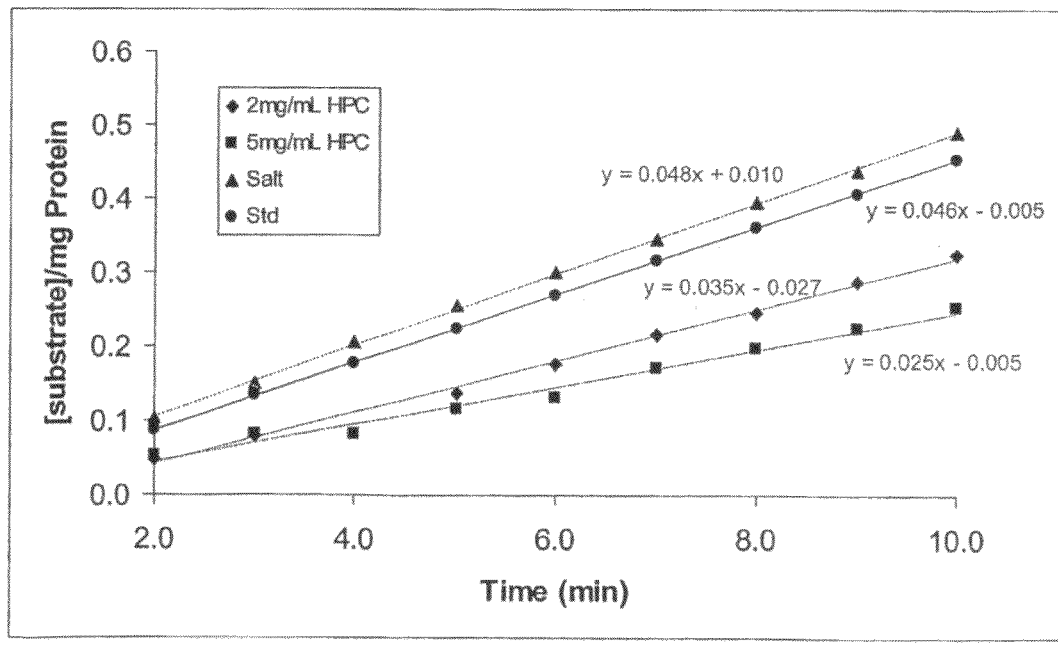
FIG. 28 is a graph showing the rates of encapsulated enzymatic activity for particles containing subtilisin made using a) HPC 2 mg/mL (♦), b) 5 mg/mL HPC (■), c) 1:1 mix of 30/360 and sodium silicate (▲), in which the standard is the enzyme in solution (●)
Figure 29:
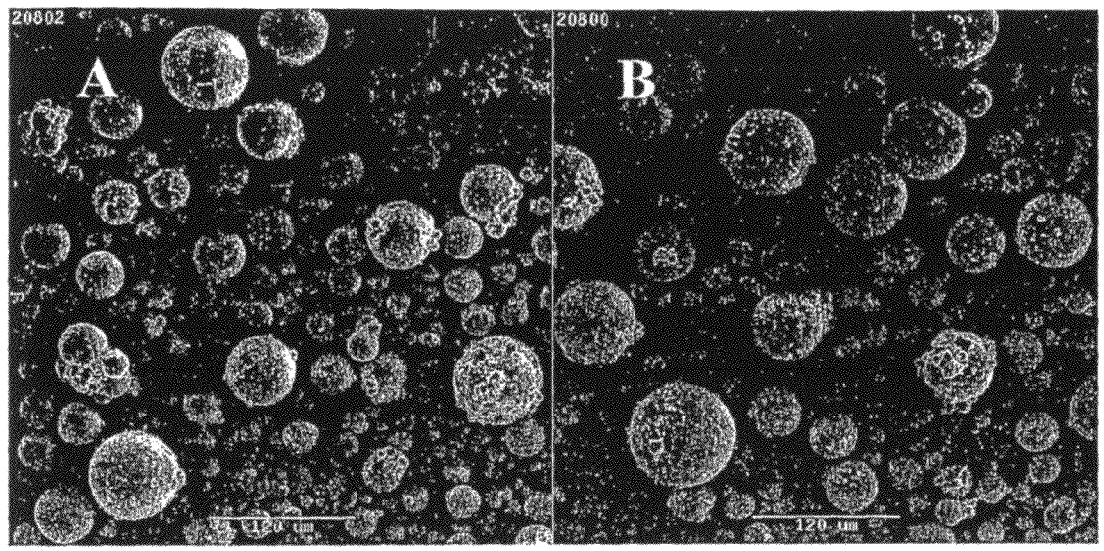
FIG. 29 is a scanning electron micrograph image showing particles according to the invention stored (A) at room temperature and (B) below 0° C.
Figure 30:
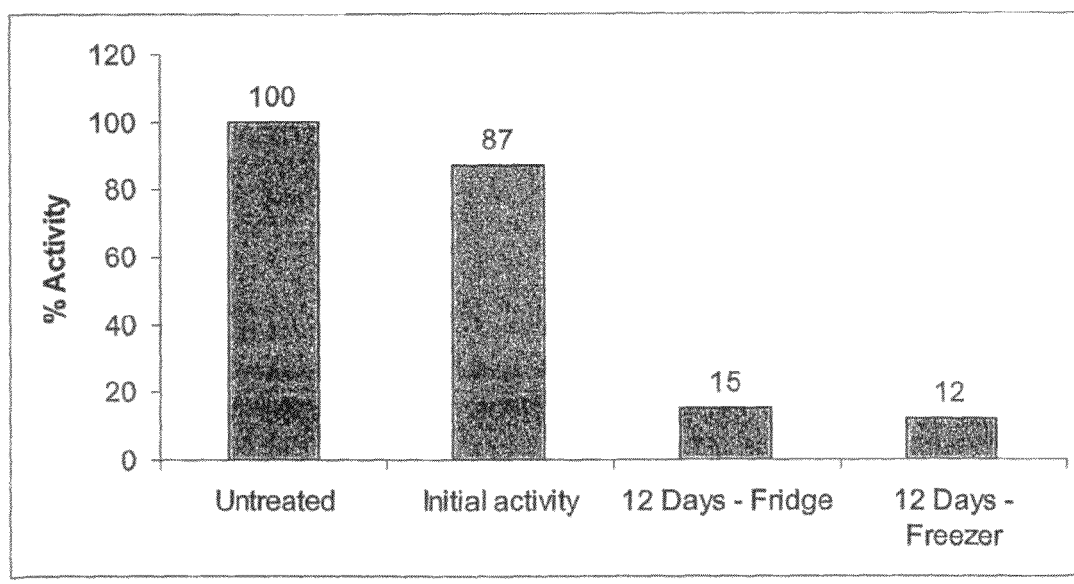
FIG. 30 is a graph showing the activity of subtilisin under various storage conditions.
Figure 31:
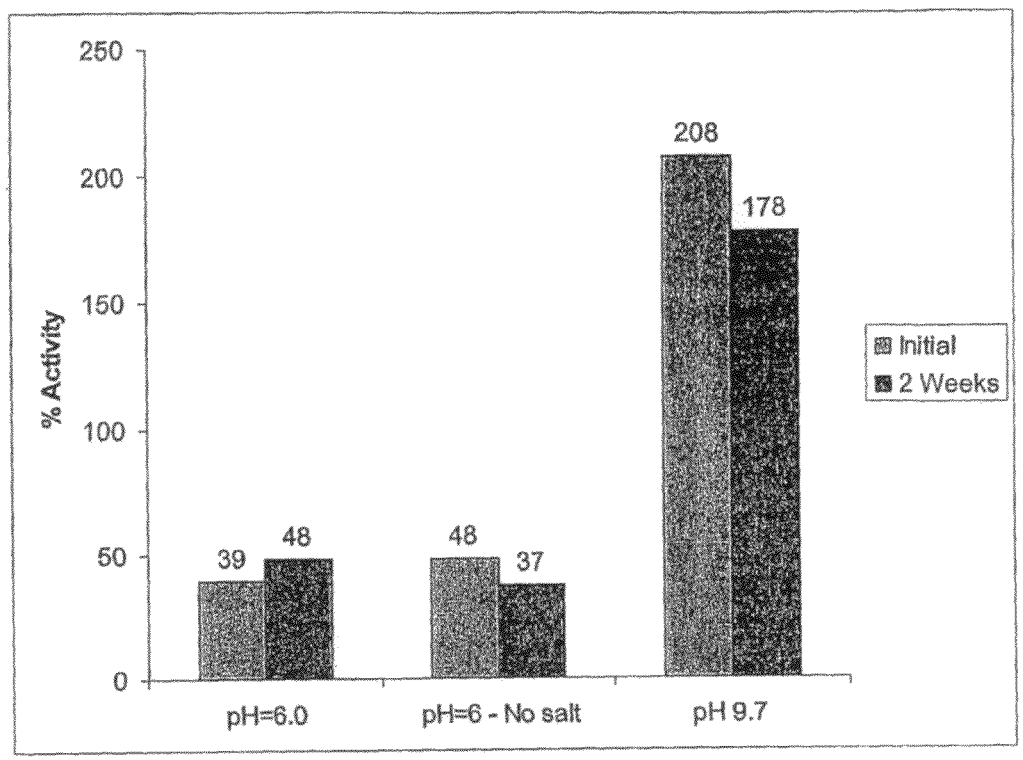
FIG. 31 is a graph showing the change in activity of encapsulated alkaline phosphatase after storage below 0° C. for two weeks.
Figure 32:
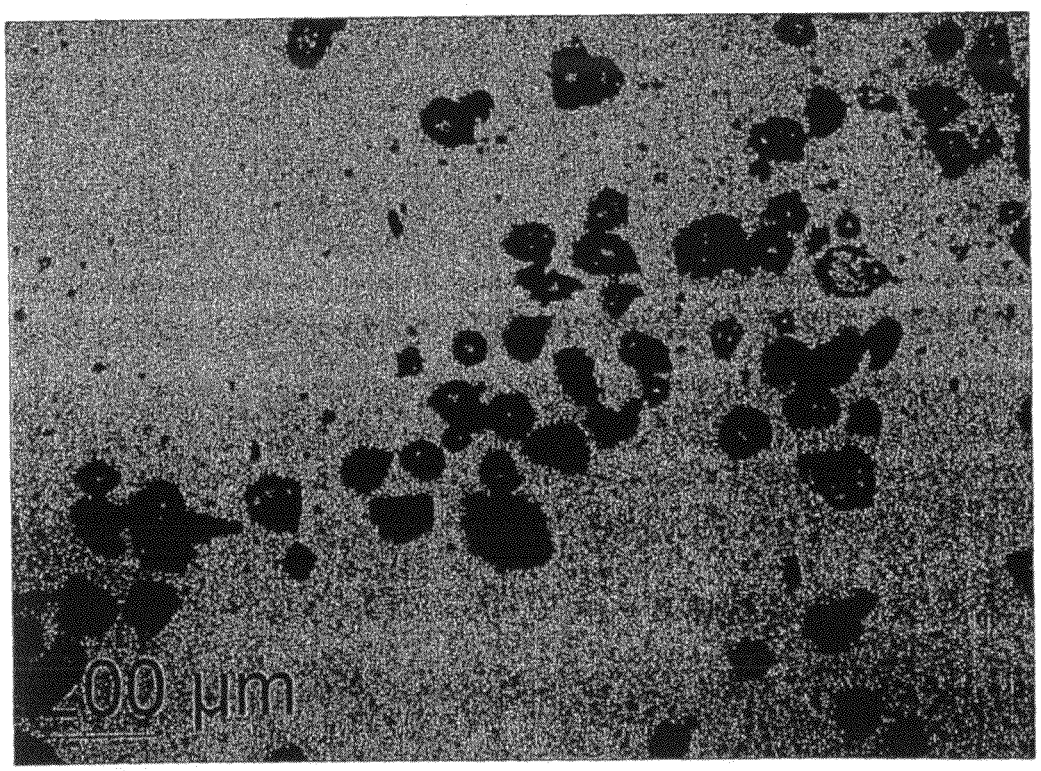
FIG. 32 is an optical micrograph of alumina particles made according to the present invention
Figure 33:
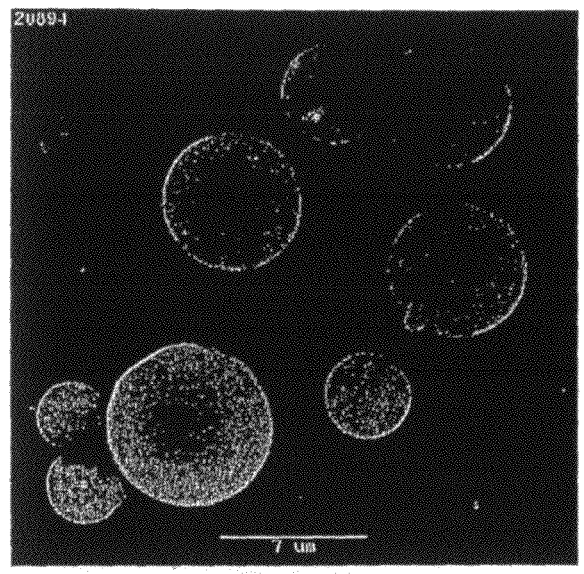
FIG. 33 is a scanning electron micrograph image of zirconotitanate microparticles according to the present invention.
Figure 34:
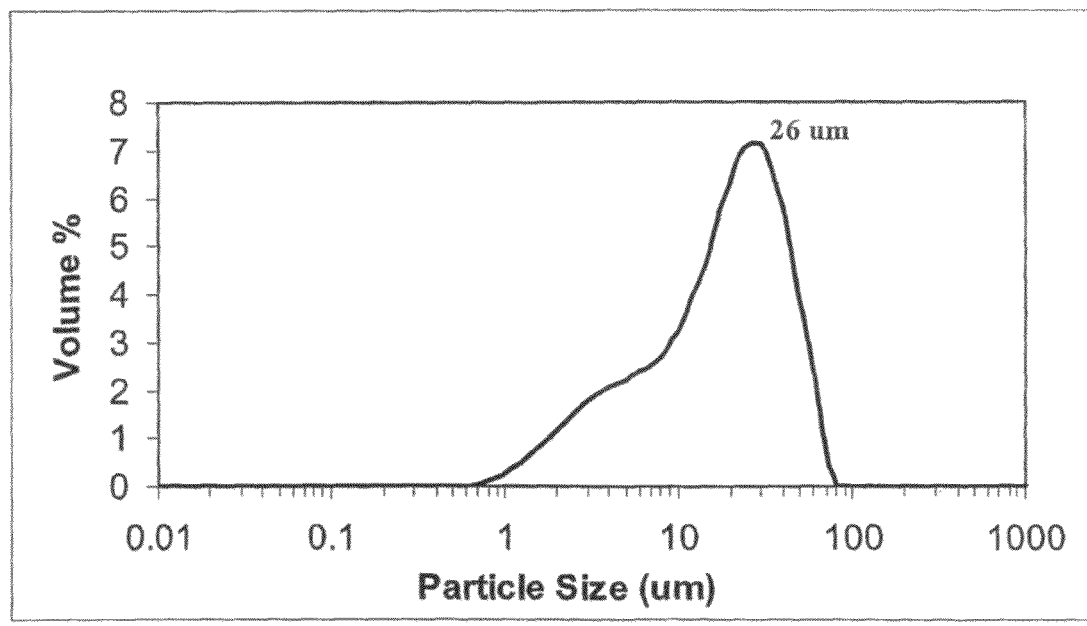
FIG. 34 is a graph showing the particle size distribution for zirconotitanate particles obtained using a Span20/kerosene emulsion according to the present invention.

Further kinetic studies of enzymes released from particles according to the present invention are described below. FIG. 28 shows the rate of enzymatic reaction of three samples, as compared to a standard (enzyme in solution). In this graph, the gradient of the lines represents the activity of the enzyme, described by the number of units of substrate formed, per unit of enzyme, per unit time. Curves a) and b) represent subtilisin encapsulated in microparticles, where the instead of salt solution, hydroxypropyl cellulose (HPC) was added at a concentration of 2 mg/mL of Bindzil, and 5 mg/mL of Bindzil respectively. Replacing the salt with HPC has reduced the rate of the reaction, indicating that the presence of HPC serves to decrease the activity of subtilisin. (See below for synthesis details). As the concentration of HPC is increased, the reaction rate is slowed. Curve c) represents subtilisin encapsulated in a 1:1 (w/w) mixture of Bindzil 30/360 and sodium silicate, as described below. It can be seen that these particles show a similar activity relative to the standard.

Synthesis Details:

Precursors for the samples containing HPC were prepared by dissolving HPC into Bindzil 30/360 at two different concentrations, corresponding to 2 mg and 5 mg of HPC respectively per mL of Bindzil 30/360. In the case of the third sample, the precursor consisted of a mixture of 0.625 mL Bindzil 30/360 and 1.875 mL of deionised silicate solution, prepared as described in Example 4.

For each sample, 9 g Span20 was dissolved in 60 ml of kerosene, 2.5 ml of the precursor solutions described above were added with stirring. The pH was reduced to 6.0 inside the emulsion by addition of 0.46 mL of 1 M HCl. A solution containing 8 mg of subtilisin in 200 µl of water was then added, followed by addition of 0.35 mL of salt solution 1 (described above). The particles were isolated using centrifugation and washed with kerosene and hexane before drying.

Example 7

Storage Stability of Encapsulated Subtilisin and Alkaline Phosphatase

The storage stability of enzymes encapsulated in microparticles is an important consideration. The majority of proteins require long term storage at temperatures below 0° C. The structural viability of microparticles formed using the process described below has been examined during a freeze-thaw process. It was initially suspected that the expansion of the water content of the particles during the freezing process may lead to an increased rate of broken or cracked particles, reducing their viability for long term storage. FIG. 29 shows the SEM micrographs of (a) a sample stored at room temperature, and (b) a sample stored at <0° C. There is no evidence in FIG. 29 for an increase in the extent of broken or cracked particles between the storage conditions.

Although the structural integrity of the overall microparticle is important, the viability of the protein stored within the matrix of the microparticles was also examined. FIG. 30 shows the enzymatic activity of subtilisin stored at about 4° C., and at less than 0° C., as compared to the activity of the sample immediately after particle synthesis. It can be seen that there was approximately an 80-90% reduction in enzymatic activity over the storage period shown. However, there was no significant difference seen between storage at 4° C. or below 0° C.

Subtilisin, a serine protease, is robust and stable in a wide variety of chemical environments. However, being a protease enzyme makes it self destructive, thereby reducing its storage stability over long periods. It is significant that the protein may be kept freeze-dried in the freezer for long periods of time, whereas the activity of the enzyme was clearly diminished inside microparticles under the same conditions. This suggests that the environment inside the microparticles may be essentially quasi-aqueous. This suggestion was tested by preparing two subtilisin doped samples as described below, and freeze-drying one. Both samples were then stored in a freezer. After two days storage, the activity of the freeze-dried sample was three times higher than the undried sample, and was essentially unchanged after 9 days storage. This confirms that although the material appears a dry solid, the amount of water present could be problematic in the case of protease enzymes, and samples should be freeze-dried before storage. Conversely, as can be seen from FIG. 31, the activity of alkaline phosphatase (synthesis details given in Example 1) was not significantly affected by storage over two weeks, generally showing only a small subsequent lose in activity in the time period shown.

Synthesis Details:

18 g of Span 20 was dissolved in 120 mL kerosene. 5 mL of Bindzil 30/360 was added with stirring. The pH was lowered to 6.0 by addition of 0.915 mL 1M HCl. A solution of 16 mg of subtilisin in 400 µl water was added to the emulsion, followed by 0.39 mL of salt solution 1. The particles were isolated using centrifugation and washed with kerosene and hexane before drying.

Example 8

Alternative Matrix for Protein Encapsulation

Two alternative ceramic matrices have been investigated. The first, alumina, was prepared from alumina sol as described below. Alumina sol was prepared by hydrolysis of aluminium sec-butoxide in water, using a water:alkoxide ratio of 10:1, and reaction temperature of 75° C. The mixture was stirred for 30 minutes and the temperature raised to 81° C. to remove the alcohol produced. Nitric acid was then added at a $H^+$:alkoxide molar ratio of 0.07:1 and the solution stirred for one hour at 81° C. The mixture was then sealed and stored at 80° C. to complete peptisation. Light scattering indicated that the mean colloid size was 9 nm. The sol was concentrated by rotary evaporation to a concentration of 10 wt % alumina.

9 g of Span20 was dissolved in 60 mL kerosene, 2 mL of 10 wt % alumina sol was added to the Span20/kerosene mixture, with stirring at 500 rpm. A 0.05 mL aliquot taken from a 50 mL aqueous solution containing 0.1 g $KH_2PO_4$, 6.69 g NaCl, and 1.3 g $CaCl_2$ was added. Stirring was continued for five hours, and then the mixture was centrifuged at 2000 rpm to remove the solid, which was washed once with kerosene, then twice with ethanol, before drying. An optical micrograph (FIG. 32) indicates that the particles were large (average particle size about 60 microns) and the sample contained a significant proportion of non-spherical fragments from shattering of the larger spheres on drying and handling. The alumina particles were also somewhat misshapen, possibly due to the soft nature of alumina gel. Due to the damage suffered by the alumina particles, a second ceramic, zirconotitanate, known to result in relatively hard gels, was investigated.

A zirconotitanate sol was prepared using a 1:1 (mol) mixture of zirconium tetrabutoxide (ZBT) and titanium tetrabutoxide (TBT). Acetic acid (5:1 (mol) acetic acid: (Ti+Zr)) was added to slow down the hydrolysis of ZBT and TBT, followed by addition of water (25:1 (mol) $H_2O$:(Ti+Zr)). PCS measurements indicate that the sol consisted of 28 nm colloidal particles. The pH of the sol was 3.0. 2.5 mL of the above sol was added to a solution of 9 g Span 20 in 60 mL of kerosene. After stirring for one hour, the solid was removed by centrifugation, and washed using kerosene and ethanol. Spherical microparticles were observed by optical microscopy. FIG. 33 shows a typical SEM image. Light scattering measurements indicate that the particles range from about 1-100 micron in size, with an average size about 26 micron (see FIG. 34). Surface area and porosity measurements indicate that the material is microporous, with two peaks in the pore size distribution at 1.1 and 2.0 nm.

Figure 35:
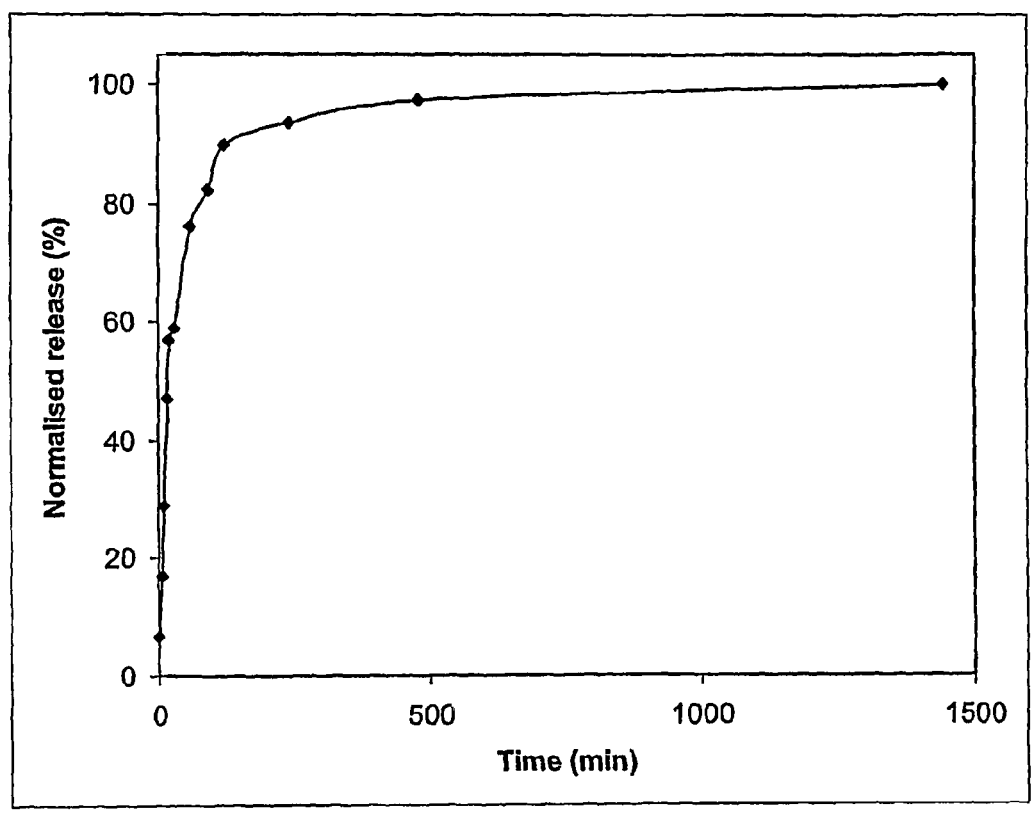
FIG. 35 is a graph showing the normalized release of bromelain from zirconotitanate particles according to the present invention.

As an example of encapsulating a biomolecule in the zirconotitanate particles, bromelain (a proteinase derived from pineapples) was chosen because of its relatively small size (~28 kDa) and stability in acidic conditions. The release curve is shown in FIG. 35.

Synthesis Details:

9 g Span 20 was dissolved in 60 ml kerosene. 8 mg of bromelaine was partially dissolved in 200 µl water. The sample was centrifuged to remove undissolved protein, before addition to 2.5 mL of the zirconotitanate sol, prepared as described above. The sol/protein mixture was dispersed with stirring into the surfactant solution, and stirred for 6 hours. The solid was removed by centrifugation, and was washed with kerosene once, and twice with hexane, using centrifugation to remove the supernatant after each wash.

ADVANTAGES OF THE INVENTION

By comparison with polymeric systems, use of a ceramic encapsulant as described in the present invention offers the following advantages:

Production uses relatively benign conditions for proteins and other biological entities, thus maintaining high protein activities upon release (as demonstrated in Example 6). There is only minor exposure to relatively unharmful, long-chain organics during synthesis and the encapsulating matrix is entirely inorganic. Synthesis of the particles and encapsulation of the biological entity may be conducted at ambient temperatures.

The release mechanism is by diffusion through internal pores of controllable size. Diffusion rates are less dependent on the local chemical environment (i.e. potentially less variability with different environment).

Metal oxides are intrinsically hydrophilic and thus should be more stable in blood. Novel biodistribution may be possible.

Gels produced from aqueous colloid provide an inherently quasi-aqueous environment and the resulting particles may contain ~10% wt water. This may provide the potential for enhanced storage stability for some biologicals, as demonstrated in Example 7.

Additionally, the ceramic system has intrinsic features which make it attractive for application to protein drug delivery, as follows:

The ceramic particles are chemically and biologically inert, and do not react with solvents/chemicals to which polymers are susceptible. They are stable in even strongly acid conditions (e.g. stomach).

They are thermally stable and non-flammable.

Silica and other light metal oxides are intrinsically biocompatible, and some even occur naturally in body.

The synthesis of the particles is 'biomolecule friendly' and the silica gel precursors are benign to proteins.

The ceramic particles have a hydrophilic surface, which enhances stability in blood. They may offer novel biodistribution characteristics.

The ceramic particles are mechanically strong, and are not readily damaged by external forces.

It is possible to exercise independent control over the size and release rate of the particles. These parameters may be introduced with good reproducibility.

All syntheses may be conducted at ambient temperature.

The same generic process for encapsulation may be used for all proteins.

The process uses relatively inexpensive ingredients which are commercially available in industrial quantities.

The process requires only low capital investment.

It may be possible to functionalise the particle surface. This might open the possibility for targeted delivery of the protein.

The process of the present invention was developed in order to extend the controlled release technology detailed in Barbé and Bartlett WO 01/62232 (2001) from release of small molecules such as drugs to release of larger biomolecules, such as proteins (including enzymes), polypeptides, and DNA/RNA fragments. The process is based on the use of a solvent/surfactant emulsion system to form spherical silica particles, but uses chemistry which is more suited to proteins and other biological entities. A suitable precursor material which may be used in the invention is a commercial silica colloid, or mixture of colloids, with optional addition of sodium silicate solution to further control the particle pore size. Use of aqueous based silica precursor contributes to overcoming two problems. Firstly, proteins are typically denatured by the alcohols produced in the hydrolysis of silicon alkoxides, which is avoided by use of the present system. Secondly, use of aqueous silica gel precursor results in a mesoporous product with pores in a suitable size range for release of proteins, which may range in size from 1-15 nm. Although aqueous based silica precursors are preferred because of their low cost and ease of preparation, they may be substituted if required (e.g. for the purpose of protection of the payload in base) with other aqueous based ceramic precursors such as titanates, zirconates or aluminates.

Possible applications for the technology described in the present invention include protein medical/drug delivery (protein drug delivery, skin graft, bone regeneration, gene therapy)

biotechnology applications such as controlled release of enzymes (biocatalysts), for example in detergents, starch hydrolysis/fructose production, fruit juice manufacture, brewing, textiles, animal feed, baking, pulp and paper production, leather industry, food production (eg cheese), specialised industrial use of enzymes e.g. in biosensors and other analytics, personal care products (eg toothpaste, contact lens cleaning), fine chemical production (eg chirally pure amino acids, rare sugars, semisynthetic penicillins), DNA-technology (genetic engineering).

cosmetics, cosmeceuticals food, nutraceuticals veterinary applications

The invention claimed is:

1. A process for releasably encapsulating a biological entity comprising:
    a) combining a solution of a surfactant in a non-polar solvent with (i) primary particles of a precursor material, said primary particles having a diameter of up to about 500 nm and (ii) the biological entity to form an emulsion comprising a polar phase dispersed in a non-polar phase, said polar phase comprising the biological entity; and
    b) aggregating the primary particles in the emulsion to form ceramic particles comprising the biological entity from the polar phase.

2. The process of claim 1 wherein the precursor material is a non-alcoholic and non-alcohol-producing precursor material.

3. The process of claim 1 wherein step a) comprises:
    c) combining the solution of the surfactant in the non-polar solvent with the precursor material to form a first emulsion, said first emulsion having a polar phase dispersed in a non-polar phase and said precursor material being located in the polar phase; and d) combining the first emulsion with the biological entity such that the polar phase comprises the biological entity.

4. The process of claim 3 comprising the step of adjusting the pH of the first emulsion to a pH at which the biological entity remains active, said step being performed before step d).

5. The process of claim 1 wherein step a) comprises:
e) combining the solution of the surfactant in the non-polar solvent with an aqueous acid to form a second emulsion, said second emulsion having a polar phase dispersed in a non-polar phase;
f) adding the precursor material to the second emulsion such that the precursor material is located in the polar phase; and
g) adding the biological entity such that the polar phase comprises the biological entity.

6. The process of claim 1 wherein step a) comprises:
h) combining the precursor material and the biological entity to form a polar mixture; and
i) combining the polar mixture with the solution of the surfactant to form the emulsion, said emulsion having a polar phase dispersed in a non-polar phase, such that the polar phase comprises the precursor material and the biological entity.

7. The process of claim 6 comprising adjusting the pH of the polar mixture to between about 7.5 and about 11, prior to step i).

8. The process of claim 1 wherein the emulsion is at a pH between about 1 and about 11.

9. The process of claim 1 wherein the primary particles have a diameter between about 5 and 100 nm.

10. The process of claim 1 wherein the precursor comprises colloidal silica.

11. The process of claim 1 wherein the biological entity is selected from the group consisting of proteins, polypeptides, and DNA/RNA fragments.

12. The process of claim 1 wherein the biological entity comprises an enzyme.

13. The process of claim 1 additionally comprising adding a gelation aid before step b).

14. The process of claim 13 wherein the gelation aid is selected from the group consisting of a salt and a water soluble polymer.

15. The process of claim 1 additionally comprising the step of at least partially separating the particles from the non-polar phase.

16. The process of claim 15 wherein the step of at least partially separating comprises the step of combining the emulsion comprising the particles with a precipitating solvent so as to precipitate the particles, said precipitating solvent being miscible with the non-polar solvent.

17. The process of claim 15 wherein the at least partially separating comprises the step of centrifuging the emulsion comprising the particles.

18. The process of claim 15 additionally comprising drying the particles.

19. The process of claim 1 comprising:
j) combining the solution of the surfactant in the non-polar solvent with colloidal silica to form a first emulsion, said first emulsion having a polar phase dispersed in the non-polar phase;
k) adjusting the pH of the first emulsion to a pH between about 1 and about 11;
l) combining the first emulsion with the biological entity such that the polar phase comprises the biological entity; and
m) forming particles comprising the biological entity from the polar phase.

20. The process of claim 1 comprising:
n) combining the solution of the surfactant in the non-polar solvent with an aqueous acid to form a second emulsion, said second emulsion having a polar phase dispersed in the non-polar phase;
o) adding colloidal silica to the second emulsion such that the pH of the second emulsion is between about 1 and about 11;
p) adding the biological entity to the second emulsion such that the polar phase comprises the biological entity; and
q) forming particles comprising the biological entity from the polar phase.

21. The process of claim 1 comprising:
r) combining the precursor material and the biological entity to form a polar mixture;
s) adjusting the pH of the polar mixture to between about 1 and about 11;
t) combining the polar mixture with the solution of the surfactant to form the emulsion having a polar phase dispersed in the non-polar phase, said polar phase comprising the polar mixture; and
u) forming particles comprising the biological entity from the polar phase.

* * * * *